(12) United States Patent
Utermohlen et al.

(10) Patent No.: US 7,964,380 B2
(45) Date of Patent: Jun. 21, 2011

(54) NANOPARTICLES FOR MANIPULATION OF BIOPOLYMERS AND METHODS OF THEREOF

(75) Inventors: Joseph G. Utermohlen, Tucson, AZ (US); Michael E. Hogan, Tucson, AZ (US); Paul Diggins, Tucson, AZ (US)

(73) Assignee: Argylia Technologies, Tucson, AZ (US)

(\*) Notice: Subject to any disclaimer, the term of this patent is extended or adjusted under 35 U.S.C. 154(b) by 765 days.

(21) Appl. No.: 11/338,124

(22) Filed: Jan. 23, 2006

(65) Prior Publication Data

US 2006/0177855 A1 Aug. 10, 2006

Related U.S. Application Data

(60) Provisional application No. 60/646,155, filed on Jan. 21, 2005, provisional application No. 60/701,630, filed on Jul. 22, 2005.

(51) Int. Cl.
- *C12N 11/02* (2006.01)
- *C12N 11/00* (2006.01)
- *C12N 11/16* (2006.01)
- *C12Q 1/68* (2006.01)

(52) U.S. Cl. ........................ 435/177; 435/174; 435/6
(58) Field of Classification Search .................. 435/177, 435/174, 6
See application file for complete search history.

(56) References Cited

U.S. PATENT DOCUMENTS

| | | | |
|---|---|---|---|
| 3,946,134 A | 3/1976 | Sherman | 428/403 |
| 4,102,977 A | 7/1978 | Sugahara et al. | 423/118 |
| 4,245,064 A | 1/1981 | Drobnik et al. | 525/329 |
| 4,540,486 A | 9/1985 | Ramsden | 210/198.2 |
| 4,677,027 A | 6/1987 | Porath et al. | 428/407 |
| 4,696,980 A | 9/1987 | Porath | 525/326.1 |
| 4,742,118 A | 5/1988 | Parekh | 525/127 |
| 4,897,467 A | 1/1990 | Porath | 530/415 |
| 5,037,795 A \* | 8/1991 | Wieserman et al. | 502/401 |
| 5,141,966 A | 8/1992 | Porath | 521/32 |
| 5,153,166 A | 10/1992 | Jain et al. | 502/402 |
| 5,185,313 A | 2/1993 | Porath | 502/402 |
| 5,582,988 A | 12/1996 | Backus et al. | 435/6 |
| 5,622,822 A | 4/1997 | Ekeze et al. | 435/6 |
| 5,652,141 A | 7/1997 | Henco et al. | 435/270 |
| 5,914,044 A | 6/1999 | Lindoy et al. | 210/670 |
| 5,922,537 A \* | 7/1999 | Ewart et al. | 435/6 |
| 5,942,463 A | 8/1999 | Oscarsson et al. | 502/402 |
| 6,150,103 A | 11/2000 | Ness et al. | 435/6 |
| 6,280,789 B1 | 8/2001 | Rey et al. | 427/2.27 |
| 6,329,058 B1 | 12/2001 | Arney et al. | 428/403 |
| 6,361,944 B1 \* | 3/2002 | Mirkin et al. | 435/6 |
| 6,395,029 B1 | 5/2002 | Levy | 623/11.11 |

(Continued)

FOREIGN PATENT DOCUMENTS

EP 1 036 082 5/2002

(Continued)

OTHER PUBLICATIONS

The defintion of "flocculent" provided by the online dictionary at Merriam-webster.com.\*

(Continued)

*Primary Examiner* — Robert T. Crow
(74) *Attorney, Agent, or Firm* — Donna E. Becker

(57) ABSTRACT

Matrices for manipulation of biopolymers, including the separation, purification, immobilization and archival storage of biopolymers is disclosed.

57 Claims, 9 Drawing Sheets

Silver stain 3-8% Tris-acetate polyacrylamide gel of serum proteins fractionated by Cibacron Blue coated nanoparticles, by the protein chromatography with nanoparticles as described in Example 18 using the chromatographic process described in Example 36.

U.S. PATENT DOCUMENTS

| | | | |
|---|---|---|---|
| 6,537,979 | B1 | 3/2003 | Kuo et al. ............... 514/54 |
| 6,552,114 | B2 | 4/2003 | Turner et al. ............ 524/445 |
| 6,565,873 | B1 | 5/2003 | Shefer et al. ............ 424/426 |
| 6,585,822 | B2* | 7/2003 | Berube et al. ........... 428/32.34 |
| 6,596,699 | B2 | 7/2003 | Zamora et al. .......... 514/44 |
| 6,602,718 | B1 | 8/2003 | Augello et al. .......... 436/176 |
| 6,718,742 | B1 | 4/2004 | Baker ....................... 54/28 |
| 2002/0034827 | A1* | 3/2002 | Singh et al. ............. 436/177 |
| 2002/0150669 | A1 | 10/2002 | Pui et al. .................. 427/2.1 |
| 2002/0160098 | A1 | 10/2002 | Zamora et al. .......... 427/2.11 |
| 2003/0018175 | A1 | 1/2003 | Andersen et al. ........ 530/395 |
| 2003/0077839 | A1* | 4/2003 | Takei ....................... 436/177 |
| 2003/0082237 | A1 | 5/2003 | Cha et al. ................. 424/490 |
| 2003/0096268 | A1* | 5/2003 | Weiner et al. ........... 435/6 |
| 2003/0119063 | A1 | 6/2003 | Pham ....................... 435/7.1 |
| 2003/0146161 | A1* | 8/2003 | Herman ................... 210/657 |
| 2003/0171552 | A1* | 9/2003 | Weidanz et al. ......... 530/388.22 |
| 2004/0126890 | A1 | 7/2004 | Gjerde et al. ............ 436/53 |

FOREIGN PATENT DOCUMENTS

| | | |
|---|---|---|
| WO | 99/29703 | 6/1999 |
| WO | 00/57982 | 10/2000 |
| WO | 02/48164 | 6/2002 |

OTHER PUBLICATIONS

Boussif, O., et al., "A versatile vector for gene and oligonucleotide transfer into cells in culture and in vivo: Polyethylenimine", *Proc. Natl. Acad. Sci. USA*, 92: 7297-7301 (1995).

Brus, C. et al., "Efficiency of polyethylenimines and polyethylenimine-graft-poly (ethylene glycol) block copolymers to protect oligonucleotides against enzymatic degradation", *European Journal of Pharmaceutics and Biopharmaceutics*, 57: 427-430, (2004).

Choosakoonkriang, S., et al., "Biophysical characterization of PEI/DNA complexes", *Journal of Pharmaceutical Sciences*, 92(8): 1710-1722 (2003).

Chrisey, Linda A., et al., "Covalent attachment of synthetic DNA to self-assembled monolayer films", *Nucleic Acids Research*, 24(15): 3031-3039 (1996).

Coletti-Previero, M.A., et al., "Alumina-phosphate complexes for immobilization of biomolecules", *Analytical Biochemistry*, 180: 1-10 (1989).

Liang, Li, et al., "Optimizing the delivery systems of chimeric RNA—DNA oligonucleotides: Beyond general oligonucleotide transfer", *Eur. J. Biochem*, 269: 5753-5857 (2002).

McNeff, C., et al., "Synthesis and use of quaternized polyethylenimine-coated zirconia for high-performance anion-exchange chromatography", *Analytical Chemistry*, 67(21): 3886-3892 (1995).

Sanchez-Cortes, S., et al., "Adsorption of polyethylenimine on silver nanoparticles and its interaction with a plasmid DNA: A surface-enhanced raman scattering study", *Biomacromolecules*, 3: 655-660 (2002).

Sandberg, L.M., et al., "Thiophilic interaction chromatography for supercoiled plasmid DNA purification", *Journal of Biotechology*, 109: 193-199 (2004).

Thomas, Mini, et al., "Conjugation to gold nanoparticles enhances polyethylenimine's transfer of plasmid DNA into mammalian cells", *Proc. Natl. Acad. Sci. USA*, 100(16): 9138-9143 (2003).

Tiyaboonchai, W., et al., "Formulation and characterization of DNA—polyethylenimine-dextran sulfate nanoparticles", *European Journal of Pharmaceutical Sciences*, 19: 191-202 (2003).

Cotton, F.A., et al., "Periodic table of the elements", *Advanced Inorganic Chemistry, Fifth Edition*, John Wiley & Sons, Inc. inside back cover (1988).

Circular Periodic Table of Elements from www.geocities.com/gemowery/CircularPeriodicTableofElements.html.

Lehmann, Urs, "Chromatographic separation as selection process for prebiotic evolution and the origin of the genetic code", *BioSystems*17:193-208 (1985).

PCT Written Opinion, International Application No. PCT/US2006/028635, 15 pages, (Jul. 28, 2008).

PCT International Search Report, International Application No. PCT/US2006/028635, 6 pages, (Jul. 28, 2008).

\* cited by examiner 558 bp amplicon 558 bp amplicon

Use of kaolin nanoparticle to concentrate whole blood DNA eluted from cellulose paper (Whatmann FTA paper).

Electrophoretic analysis of PCR products PCR analysis of whole blood DNA extracted with sodium dodecyl sulfate and ethanol induce adsorption.

Electrophoretic analysis of PCR products from whole blood extracts extracted with sodium lauroyl sarcosine and guanidine hydrochloride An ethidium bromide stained gel of 330 bp PCR products of the human GSTP1C allele from DNA samples isolated from buccal cells harvested by Fiztco cheek swab.

Silver stain 3-8% Tris-acetate gel polyacrylamide gel of proteins that bound to kaolin nanoparticle with the epoxy-silane-DTT-DVS thiophilic ligand.

Silver stain 3-8% Tris-acetate polyacrylamide gel of serum proteins fractionated by
Cibacron Blue coated nanoparticles, by the protein chromatography with
nanoparticles as described in Example 18 using the chromatographic process
described in Example 36.

NANOPARTICLES FOR MANIPULATION OF BIOPOLYMERS AND METHODS OF THEREOF

CROSS-REFERENCE TO RELATED APPLICATIONS

The present application relates to and claims priority to provisional applications, Ser. No. 60/646,155, filed Jan. 21, 2005 and Application Ser. No. 60/701,630, filed Jul. 22, 2005.

BACKGROUND OF THE INVENTION

DNA, RNA, immunoglobulins and proteins are classes of polymeric biomolecules ("biopolymers") of particular importance in modern biochemical and molecular biological methods and processes. Specifically, biopolymers play critical roles in various subcellular processes including the preservation and transmission of genetic information, the production of proteins, and the formation of enzymes.

Because of the importance of these biopolymers in various biological processes, a wide variety of techniques have been developed to physically bind these classes of molecules in order to achieve their immobilization, purification, concentration, archival storage, etc., i.e., in order to manipulate such molecules. For example, various column methods have been developed to bind a biopolymer to a matrix with affinity for that biopolymer, thereby allowing for its immobilization, its separation from contaminating cellular components, its concentration, etc. See, e.g., U.S. Pat. No. 5,652,141 for the purification of nucleic acids (i.e., DNA and RNA). Similarly, various bulk separation methods have been developed for the immobilization, separation, or concentration of biopolymers, e.g., the use of magnetic beads comprising a magnetic or paramagnetic particle and an attached ion exchange material capable of binding the biomolecule. See, e.g., U.S. Pat. No. 6,718,742.

Biopolymer immobilization, separation, concentration or purification is employed across a wide range of commercial applications, including, for example, forensics, pharmaceutical research and development, medical diagnostics and therapeutics, environmental analysis, such as water purification or water quality monitoring, nucleic acid purification, proteomics, and field collection of biological samples. Thus, a great need exists for efficient, simplified processing of clinical, environmental and forensic samples; especially those containing nanogram amounts of nucleic acid or protein.

There are generally three classes of current technology for nucleic acid extraction and purification from fluidized cellular or tissue suspensions: a) Organic Precipitation; b) Adsorption to Glass Column or Fiber Supports; and c) Adsorption to Magnetic Beads.

Organic precipitation is generally the method of choice for extraction of samples larger than about 1 ml, because it scales to large size well. It is based on the semi-selective precipitation of high molecular weight DNA and RNA, induced by organic solvents and chaotropes, followed by harvesting of the precipitate by high speed centrifugation. The primary precipitate, which is only semi-pure, is then dissolved and additionally purified by protease treatment and ordinarily, a second round of precipitation at −20° C., in an organic solvent.

One disadvantage of the precipitation method lies in the complexity and the need to have access to cryogenics and a high speed preparative centrifuge to affect precipitation. The methods are generally unsuited to routine automation. For this reason, the precipitation method is currently used mainly in low volume applications, as in a bench scale biochemistry laboratory, and especially for large volume samples (in excess of 5 mL) such as 8 mL blood samples or plant or animal tissue extracts.

Adsorption onto a glass column or fiber supports is based upon adsorption of nucleic acid to a column of porous glass beads or to filters made from glass fibers. It is performed by lysing a fluidized sample as would be done in the precipitation method, but instead of precipitation of the nucleic acid, the nucleic acid is induced to adsorb onto a treated glass surface: generally as a result of adding salts, chaotrope or alcohol to the fluid phase, to make the nucleic acid less soluble. Once adsorbed to the solid support (column or fiber), contaminants are flushed away by washing of the solid support with an appropriate wash solution, usually containing alcohol to retain tight nucleic acid adsorption. Finally, nucleic acid is released from the support by addition of an alcohol-free buffer, thereby eluting the nucleic acid into a small volume for subsequent genetic analysis.

This method is widely used as the basis for commercial products. One advantage of this method is that it is relatively simple, requires somewhat less laboratory infrastructure than the biochemical precipitation method and because it is relatively easy to automate, in a 96 well microplate format. Another disadvantage of the method is that, as for precipitation, it requires rather precise control of the lysis, washing and elution steps in order to obtain high yields and high purity. Moreover, as for the precipitation methods, it requires access to relatively sophisticated biochemical lab equipment: centrifuges, pressure filtration devices, etc. Yet another disadvantage is that it does not scale well to large sample size. Thus, the glass adsorption method is superior to the precipitation methods and is very well suited for samples less than about 1 ml, especially when standardized automation is a requirement for high throughput applications. A final disadvantage is one of cost. Since the adsorption methods must be used in the context of a column-based chromatographic separation or a filtration based separation, they are provided commercially as an integrated plastic device (spin columns, filter-bottom microplates, etc) which adds significant consumable cost to the overall process.

Adsorption onto magnetic beads entails using plastic coated micron-sized beads (that have a density near to one, and a size range from 1 to 50 microns) with iron, or an equivalent diamagnetic substance at their center. Because these beads have a density near to that of water, they cannot be easily manipulated by centrifugation. However, because they have an iron core, they can be drawn to the bottom or the side of a vessel by a magnet. For nucleic acid purification, such beads are coated with a neutral or cationic coating and, similar to the glass bead technology, nucleic acid is purified by adsorption to the bead surface: but followed by bead isolation in the presence of a nearby magnet, thereby drawing bead-bound nucleic acid to the bottom of a preparative tube.

In contrast to the precipitation or glass bead or filtration technology, an advantage of the magnetic bead technology is that it requires very little specialized laboratory equipment (other than the magnet) and because it is readily automated. It is considered superior to both the glass bead and the precipitation method in that the final nucleic acid product can be isolated as a very small volume pellet, which, subsequent to addition of a small amount of release buffer, can be harvested as a microliter-sized product which in volume terms, can be ¹⁄₁₀ that provided by release from glass columns or glass filters.

Disadvantages of the magnetic bead technology are as follows. Because it is not practical to apply a magnetic field which will "pull" beads of this kind more than about 1 cm, this technology does not scale well to the isolation of nucleic acid from samples larger than about 1 mL. Since magnetic attraction is proportional to the mass of the diamagnetic material, these non-porous magnetic beads are limited in to a size ranging from 1 to 50 microns (because of the magnetic core) which is why there is a severe limitation as to the surface area available per initial unit sample volume. Moreover, the beads themselves are relatively complicated to manufacture (they have a magnetic core and a surface coating) and are therefore costly. Thus, as is the case for the glass adsorption technology, the magnetic bead technology is relatively costly and best suited for small volume sample processing.

Although each of these conventional techniques are capable of manipulating biopolymers, they suffer various difficulties in terms of cost of operation, complexity of apparatus required, amount of biopolymer obtained, concentration of biopolymer obtained, etc. In light of the importance of biopolymers to modern biological research such as the development of new therapeutic treatments, drugs, etc., there is thus a need for alternate methods for manipulating such biopolymers that address these various deficiencies in current techniques.

In contrast to the conventional nucleic acid extraction and purification methodologies, the inventive method employs sub-micron or nanoparticles that are readily available in kilogram quantities. One of the preferred nanoparticle materials, kaolin, is commercially available at high purity and at very low cost, since these materials are already used industrially as fillers and bonding agents. The coupling process that we have devised can prepare surface modified particles (e.g., epoxy-silane coated kaolin) batch-wise in kilogram quantities, under conditions where the production cost for the final product will be dominated by QC-QA and packaging. Thus, the overall cost of producing the chromatographically-useful nanoparticles as a technology will be similar to that of the low-cost precipitation methods and approximately $\frac{1}{10}$ that of the glass column or glass filter or magnetic bead technologies.

Like the glass column/glass filter technology and the magnetic bead technology, the kaolin nanoparticle technology can be readily automated, in a 96 well or 384 well format, mediated by very low speed particle isolation by gravity or low speed plate-wise centrifugation. Like the magnetic bead technology, chromatography with the nanoparticles of this invention can be performed with little to no specialized equipment: only an inexpensive low speed blood centrifuge and a pipetter. However, unlike either the glass bead or magnetic bead technology, the extraction process with nanoparticles of this invention can be scaled from the microliter scale to the liter scale effortlessly, since nucleic acid isolation is based on the application of a moderate centrifugal force allowing samples to be purified, alternatively in an "Eppendorf" tube or a blood "stick tube" or even a 250 ml blood bottle, if necessary. Also, the cost of material and manufacture is very low, and the material can be used without the need for embedding it in an expensive custom chromatography or filtration part (or coupled to the use of expensive magnets). The overall cost to the customer can be much lower than the industry standard, with equal or greater quality.

The present invention provides a unique chromatographic matrix based on highly purified, nearly mono-dispersed, ceramic nanoparticles. These nanoparticles form stable colloidal suspensions in aqueous solution, but are dense enough that they readily sediment and form a compact pellet in response to standard low speed bench top centrifugation. Since the particles are sub-micron in diameter, they display a large surface area to volume ratio. For example, a milligram of kaolin nanoparticle of 200 nm dimension, suspended in one milliliter of aqueous solution displays a total surface area in the range of 200 cm$^2$ that represents approximately 10$^{12}$ dispersed nanoparticles The inter-particle spacing between this number of particles in a milliliter is about a micron, a distance that is less than the distance a 10,000 base pair long DNA molecule or a 1,000,000 D protein would travel by passive diffusion in about one minute. Thus, even at a very low particle-mass density, and in the absence of mixing or convective flow, a 0.1% suspension of nanoparticles are at a concentration such that a targeted biomolecule is never more than "a minute away" from binding to the nanoparticle. This suggests that, independent of sample concentration, batch chromatography with nanoparticles will be complete within minutes. In addition, due to the small size of these particles, this 0.1% suspension of kaolin nanoparticles will sediment to a pellet volume of only about one microliter. The expansive surface area of these ceramic nanoparticles has very useful characteristics as the basis for chromatography: an enormous binding capacity per unit mass and the ability to be modified via well-known surface chemistry.

For batch chromatography, the outer surface area is important because it defines the mass and the volume of sample that can be processed at one time. Since the surface area per unit mass increases as 1/diameter, to make the comparison to the inventive kaolin nanoparticles, having a surface to mass of 200 cm$^2$ per milligram, for a smooth, non-porous particle of a 30 micron size beads or glass (same approximate density as kaolin and a surface area to mass ratio of 2 cm$^2$/mg), would require 100 milligrams of beads to match the surface area of 1 mg of the kaolin nanoparticles. Assuming that each kind of matrix occupies about the same space per unit mass as a pellet, the surface area presented by 1 μL of a 200 nm-nanoparticle pellet is equivalent to that of a 100 μL pellet for the standard 30-micron bead. Thus, in this very realistic example, a biologically relevant sample would have been concentrated 1000-fold via nanoparticles, but only 10-fold by the 30 uM beads. Alternatively, in terms of binding capacity, a 100 μL pellet would have the same total binding capacity as 1 uL of the nanoparticles.

Rapid development of a broad-ranging nano-chromatography platform requires the ability to chemically modify the surface of this new ceramic matrix with biomolecule-specific ligands. For ceramic nanoparticles, surface chemistry is well studied and has already been optimized for related applications in the plastics and polymers industry. In the present invention these well-known ceramic surface chemistries are paired with biochemical chromatography, to develop a flexible repertoire of surface coatings for DNA, RNA, immunoglobulin and protein applications: all based on the same underlying ceramic nanoparticle matrix.

With regard to the immobilization and storage of biopolymers, the inventive nanoparticles can be used for the storage and retrieval of nucleic acid and proteins in the solid state. It is well known in the art that immobilization of biomolecules on a surface stabilizes the molecule against changes due to environmental or enzymatic degradation. There are several other known methods of nucleic acid storage, commercial and noncommercial, namely: a) cryogenics; b) unassisted air or freeze drying; and c) drying on treated paper filters. Since these nanoparticles present such a large surface area, the expectation is that the immobilization or adsorption of nucleic acids or proteins on specially modified surfaces of these nanoparticles would be a means to store these biomolecules for later analysis.

SUMMARY OF THE INVENTION

The present invention is directed to nanoparticles as solid, non-porous particles with a surface area to volume ratio (m$^2$/ cm³) greater than 10, in which surface area to volume is determined by the surface area m²/gram multiplied by particle density ($\rho$) gr/cm³ and a density (rho) greater than 2, and have sedimentation rates (V as cm/min) in water, with $V_{minimum}$ (referred to as "$V_{min}$") greater than 0.1 cm/min at 10,000 G and $V_{maximum}$ (referred to as "$V_{max}$") less than 2 cm/min at 500 G.

The present invention is directed to nanoparticles activated by a coating of a biopolymer specific agent for manipulations of biopolymers such as those discussed above, compositions comprising such activated nanoparticles, methods for their use, and kits comprising these activated nanoparticles for performing these methods.

The one aspect of the invention is to utilize the specific chemical properties of the nanoparticle surface for biomolecule manipulation. Thus, one aspect of the present invention is directed to activated nanoparticles.

Another aspect of the present invention is directed to compositions comprising such activated nanoparticles.

Another aspect of the present invention is directed to methods for the use of the activated nanoparticles of the present invention in the manipulation of biopolymers.

Another aspect of the present invention is directed to kits comprising the activated nanoparticles of the present invention.

Another aspect of the present invention is directed to the utilizing the surface chemistry of the nanoparticles for biochemical manipulations.

Another aspect of the present invention is directed to the surface modification of nanoparticles using an adaptation of passivation chemistry that relies on oxyanions and other anions to modify the particle surface for biochemical manipulations.

Another aspect of the present invention is directed to employing the nanoparticles for chromatography to isolate, concentrate, enrich, or purify biomolecules from liquid phase or crude solutions.

Another aspect of the present invention is directed to employing the alkyl-amine coated nanoparticles as a biochemical platform for polynucleotide hybridization.

Another aspect of the present invention is directed to employing the nanoparticles coated with mononucleotides as a biochemical platform for isolating polynucleotides.

Another aspect of the present invention is directed to employing the nanoparticles coated with end-linked polynucleotides as a biochemical platform for the isolation or detection of polynucleotide of a complementary sequence.

Another aspect of the present invention is directed to employing the nanoparticles with metal oxide/hydroxide surface and coated with polynucleotides as a biochemical platform for complementary polynucleotide hybridization.

Another aspect of the present invention is directed to employing the nanoparticles with metal oxide/hydroxide surface coated oxyanions for nucleic acid or protein chromatography based on apatite affinity of the oxyanion surface for the biomolecule.

Another aspect of the present invention is directed to employing the nanoparticles as a platform for enzymes, and enzyme reactions or for binding proteins such as immunoglobulins or lectins to bind to targeted molecules.

Another aspect of the present invention is directed to employing the nanoparticles as a platform for biochemical libraries for peptides, nucleic acids, or polysaccharides for sorting or determining structure or function of such bound molecules.

Another aspect of the present invention is directed to employing the nanoparticles as a solid phase platform for affinity chromatography applications.

Another aspect of the present invention is directed to employing the nanoparticles as a solid phase platform for adsorption chromatography applications.

Another aspect of the present invention is directed to employing the nanoparticles as a solid phase platform for hydrophobic chromatography applications.

Another aspect of the present invention is directed to employing the nanoparticles as a solid phase platform for electron donor-acceptor chromatography applications as an example thiophilic ligand affinity chromatography.

Another aspect of the present invention is directed to employing the nanoparticles as a solid phase platform for metal affinity chromatography based on nanoparticles coated with metal chelating ligands, with metal ion chelated in such ligands, for protein and nucleic acid chromatography.

Another aspect of the present invention is directed to employing the nanoparticles as a solid phase platform for dye-ligand mediated chromatography applications.

Another aspect of the present invention is directed to employing the nanoparticles as a solid phase platform for anion or cation affinity chromatography applications.

Another aspect of the present invention is directed to employing the nanoparticles as a solid phase platform for nucleic acid chromatography applications.

Another aspect of the present invention is directed to employing the nanoparticles as a solid phase platform for protein chromatography applications.

Another aspect of the present invention is directed to employing the nanoparticles as a solid phase platform for polysaccharide chromatography applications.

Another aspect of the present invention is directed to employing the nanoparticles as a solid phase platform for chromatography applications to isolate organelles, cells, viruses or other biomolecule complexes.

Another aspect of the present invention is directed to employing the nanoparticles as a solid phase platform for diagnostic assay applications.

Another aspect of the present invention is directed to employing the nanoparticles as a solid phase platform to label biomolecules such as proteins, nucleic acids, cells for detection applications.

Another aspect of the present invention is directed to employing the nanoparticles as a solid phase platform for diagnosing or detection of a biomolecule due to the binding activity of a nanoparticle bound protein such as an immunoglobulin or lectin that results in the flocculation or agglutination of the nanoparticles our from colloidal suspension to form an obvious aggregate.

Another aspect of the present invention is directed to employing the nanoparticles as a solid phase platform for enzyme linked immunosorbant assay applications.

Another aspect of the present invention is directed to employing the nanoparticles as a solid phase platform for the stabilization of proteins and nucleic acids for storage applications.

Another aspect of the present invention is directed to employing the nanoparticles as a solid phase platform for purifying or detection of specific biomolecules via electrophoresis of the nanoparticles.

Another aspect of the present invention is directed to employing the nanoparticles as a solid phase platform for most biochemical reactions that require a solid phase component.

Another aspect of the present invention is directed to employing the nanoparticles as a solid phase platform for continuous flow isolation process that has at least a liquid phase and a solid phase.

Another aspect of the present invention is directed to employing the nanoparticles as a solid phase platform for continuous flow isolation process that has two liquid phases plus this solid phase.

DETAILED DESCRIPTION OF FIGURES

Figure 1:
FIG. 1:
Different ratios of kaolin:PEI kaolin particle suspension were compared to determine optimal mixtures for elution of DNA from the PEI kaolin. (See Example 7).

FIG. 1:
Different ratios of washed kaolin (Example 1) to PEI kaolin (Example 3) nanoparticle suspension were compared to determine optimal mixtures for DNA elution of the pellets composed of these various mixtures, as described in Example 7. The elution buffer was 200 mM CAPS, Na, 50 mM Tris (pH 8.0 buffer), and 0.2% SDS, total pH was around 11. For all these mixtures, the concentration of PEI kaolin was kept at 5 mg per milliliter of 1 mL DNA extract. FIG. 1 displays the PCR product from amelogenin (558 bp amplicon) generated from human DNA eluted from these different sets of nanoparticle mixtures. The PCR products of the DNA eluted from these mixtures are displayed in lanes 1 through 3 and 5 through 9, with the MW control in lane 4 the 1 kb molecular wt marker (Invitrogen cat# 15615-016), and the positive PCR control in lane 10 the PCR product from the 10 ng human DNA. Lane 1 is the PCR product from DNA eluted PIE-kaolin nanoparticles that was not mixed with any washed kaolin particles. Lane 2 is the PCR product from DNA released when 0.55 mg of kaolin was added to the PEI kaolin. Lane 3 is the PCR product from DNA released when 1.25 mg of kaolin was added to the PEI kaolin. Lane 5 is the PCR product from DNA released when 3.3 mg mg of kaolin was added to the PEI kaolin. Lane 6 is the PCR product from DNA released when 5.0 mg of kaolin was added to the PEI kaolin. Lane 7 is the PCR product from DNA released when 7.5 mg of kaolin was added to the PEI kaolin. Lane 8 is the PCR product from DNA released when 20 mg of kaolin was added to the PEI kaolin. Lane 9 is the PCR product from DNA released when 45mg of kaolin was added to the PEI kaolin.

Figure 2:
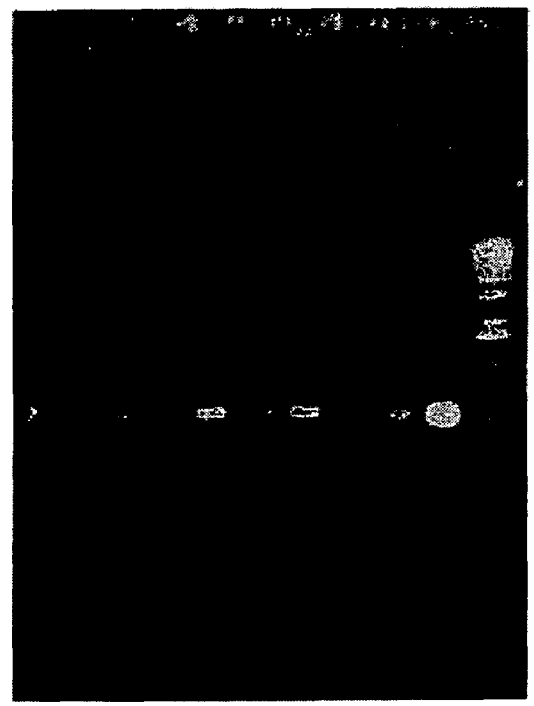
FIG. 2:
This is a gel analysis of samples as described in Example 7, an ethidium bromide agarose gel stained DNA, PCR products from reactions initiated with the DNA released from PEI kaolin nanoparticles. (See Example 7).

FIG. 2:
This is a gel analysis of samples as described in Example 7, an ethidium bromide agarose gel stained DNA, PCR products from reactions initiated with the DNA released from PEI kaolin nanoparticles. This experiment tested four different formulations of DNA release buffer, and between the DNA release from PEI kaolin nanoparticles whether or not these particles are mixed with kaolin nanoparticles during the DNA release treatment. The formulations were various combinations, all buffered with 0.2M concentration of the sodium salt of CAPS, with or without Tris buffer at 50 mM, and with or without SDS at 0.2% wt/vol. The mixtures of two nanoparticles, 5 mg of PEI kaolin to 5 mg of kaolin, were displayed in lanes 2, 4, 6, 8) versus; the release from 5 mg of PEI kaolin nanoparticles, only, are displayed in lanes 1, 3, 5, and 7. The two controls (See experiment 4) were an electrophoretic control, the 1 Kb molecular wt marker and the second was PCR reaction control, a reaction that had 10 ng of pure human DNA as the template. The results were that regardless of the release buffer, the PCR products generated from the PEI kaolin+kaolin mixtures were more efficient in releasing DNA. The results of the different release buffers were (lanes 1 and 2) 200 mM CAPS, (lanes 2 and 4), 200 mM CAPS, 0.2% SDS the buffer described in experiment 3, (lanes 5 and 6) 200 mM CAPS, 50 mM Tris (from 1M,pH 8.0 Tris solution), (lanes 7 and 8) 200 mM CAPS, 50 mM Tris-pH 8.0, 0.2% SDS. For all cases each of these buffers worked, though the 200 mM CAPS, 0.2% SDS, and 200 mM CAPS, 50 mM Tris-pH 8.0 worked best. For all the PCR reactions the final elution volume was 200 uL, and 2 ul was used as template for these 50 uL PCR reaction (See Experiment 4) and analysis of $\frac{1}{5}^{th}$ of the reaction volume by ethidium bromide stained agarose gels. The PCR reaction was of that described in Example 7.

Figure 3:
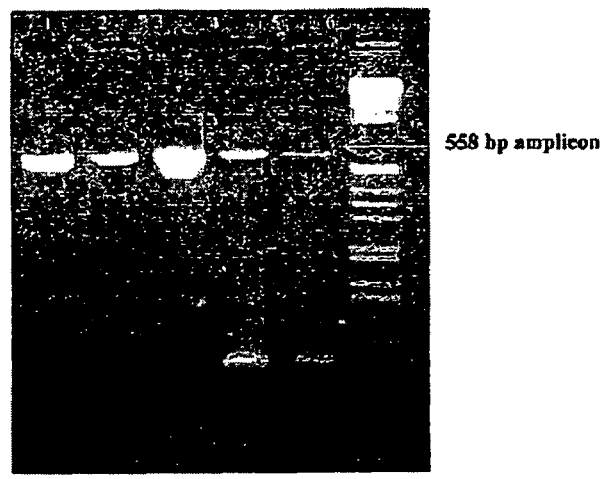
FIG. 3:
The PCR products from DNA purified from whole blood using a two tier purification process based on sequential use of PEI kaolin nanoparticles follwed by kaolin nanoparticles. (See Example 7).

FIG. 3:

FIG. 3 shows a gel of PCR products from DNA purified from whole blood using a two tier purification process based on sequential use of PEI kaolin nanoparticles followed by kaolin nanoparticles. These PCR products of 558 base pairs are from the amelogin gene (X/Y). For each lane, 10 μL of the 50 μL PCR reaction was analysed in the gel. Lanes 1 and 2 were the amplicons from DNA isolated by the two tiered process from whole human blood. The PCR reaction seen in lane 1 was initiated with 1 μL of 50 μL final DNA eluate, for the PCR reaction seen in lane 2, the reaction was initiated with 0.1 μL of the 50 μL eluate, same eluate used for PCR reaction seen in lane 1. Lanes 3, 4 and 5 were controls, the PCR products from reactions using known quantity of human genomic DNA (Roche Human Genomic DNA catalog # 1691112) as template for the reaction. The human DNA content added to these respective, 50 μL PCR reaction were 10 ng (lane 3), 1 ng (lane 4), and 0.1 ng (lane 5).

Figure 4:
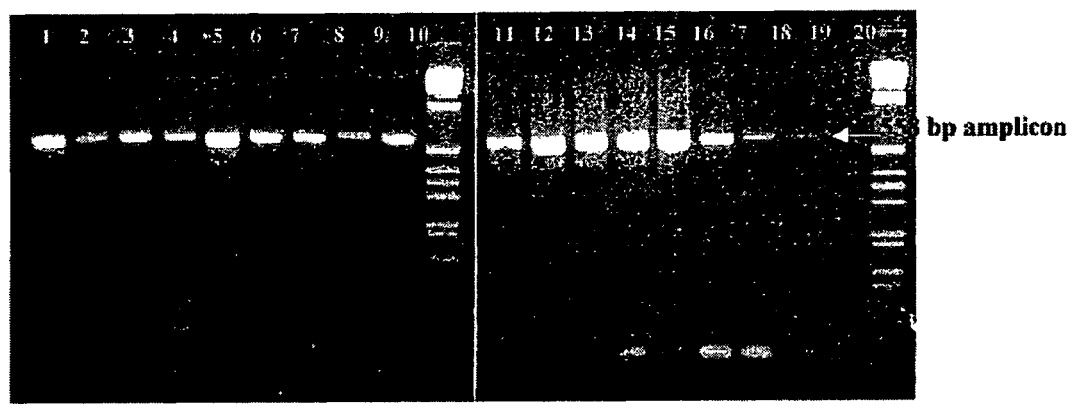
FIG. 4:
This figure displays the PCR results from adsorption concentration process using purified human DNA (For PCR conditions and control source of human DNA see Experiment 4). (See Example 8).

FIG. 4:

Conditions that support the adsorption of human DNA to washed kaolin nanoparticles in 66% solution of 2-propanol (See Example 8). FIG. 4 displays the PCR results from absorption concentration process using purified human DNA. Three quantities of human DNA dissolved in 0.5 mL volume were tested, these were 0.05 ug (lanes 1-4), 2 ug (lanes 5-8) and 5 ug (lanes 11-14). The solutions that these DNA samples were dissolved were 200 mM CAPS, 0.2% SDS, (lanes 1, 5, and 11), 200 mM CAPS, 1% SDS C (lanes 2, 6, and 12), 2× TE+1% SDS, pH 11.5 (lanes 3, 7, and 13), and 200 mM NaCl, 1% SDS (lanes 4, 8, and 14). The process was, as described in Example 8, was to each of these 0.5 mL human DNA solutions add 2 mg of kaolin nanoparticles and mix each to a confluent suspension. Then add 2 volumes (1 mL) of 2-propanol to each of the suspensions and incubate them at room temperature for 30 min. The DNA/particle complex were sedimented from each suspension by centrifugation (8000 G for 5min), then washed in 0.5 mL of 40% 2 propanol/water solution, followed by centrifugation, then air dried for 5 to 10 min. The DNA was eluted from the nanoparticles by resuspending the sedimented particles to a confluent suspension in $\frac{1}{10}$ dilution of TE and incubating these suspensions for 30 min at 55° C. These particles in the suspensions were sedimented to a tight pellet by centrifugation, and the DNA was in the eluate solution, and recovered by transferring to a new tube. The elution volume for all each of these extracts was 20 uL. For the PCR analysis (50 uL volume), the following volumes of the eluate were used as the DNA source; 4 ul of the eluate from each of the 0.05 ug samples, 0.1 uL equivalent volume (as 1 ul from a 1:10 dilution) of the eluate from each of the 2 ug samples, and 0.5 ul equivalent volume (as 1 ul of a 1:20 dilution) of the eluate from each of the 5 ug samples. As illustrated by the intensity of each band compared to each other and to the DNA standards, the yields of DNA can be deduced. The DNA standards were PCRs that were initiated with these quantities of control human DNA (as in Experiment 4), these were 10 ng in lanes 9 and 15, 1 ng in lane 16, 0.1 ng in lane 17, and 0.01 ng in lane 18.

FIG. 5:

The PCR products from DNA purified from whole blood using a two tier purification process based on sequential use of FTA paper storage followed by absorption to washed kaolin nanoparticles (See Example 7). The whole blood spotted (13 uL) was applied to a 6 mm diameter FTA paper disk and air dried. The dried sample was stored at room temperature for 24 days. For this process each sample consisted of paper eluent from 1 (lane 1), or 2 (lane 2), and 3 (lane 3) paper disks per sample. The elution process of the whole blood DNA was to soak the disks with some agitation with 10 mM Tris, pH 8.0, 0.1 mM EDTA, and 1% Triton X-100 solution, soak for 30 min, change solution and agitate and soake an additional 30 mi. This solution was removed and the disks were soaked in 10 mM Tris, 0.1 mM EDTA for 30 min, with occasional agitation, this solution was removed and this step was repeated again for an additional 30 min. This last solution was removed and these disks were soaked in 0.5 mL of elution buffer (10 mM Tris pH 11.5) inbuated for 45 min. After this incubation, the eluant solution was transfered to a fresh tube, and 10 uL of 50 mg/mL solution of washed kaolin in water was added, mixed to confluent suspension, then 1 mL of 2-propanol, this was incubated at room temperature for 1 hr. These particles were sedimented from this suspension, and washed with 70% Ethanol, centrifuged, and allowed to air dry for 10 min. To elute the DNA from the kaolin nanoparticles, 20 uL of a $\frac{1}{10}$ dilution of TE buffer was added to the pellets and resuspened and incubated for 1 hour at 55° C. The kaolin nanoparticles were resedimented from suspension and the DNA eluant was transfered to a new tube.

The PCR products in lane Tare from the reaction initiated with 2 uL of the single disk extract, for lane 2 are from the reaction initiated with 1 uL of the extract from two disks, and for lane 3 are from the reaction initiated with 0.5 uL volume equivalent (5 uL of $\frac{1}{10}$ dilution of the kaolin eluant) for the three disk extract. Lanes 4 through 8 were PCR products initiated with 10 ng, 10 ng, 0.1 ng and 0.01 ng, and the negative (no DNA) control, respectively. Lane 9 is the 1 kb ladder (Roche Human Genomic DNA catalog # 1691112). The results of this experiment indicates that an expected yield of DNA was obtained for each, though the observation was that some detergent remained with the kaolin nanoparticles throughout the isolation, thus the three disk extract contained more detergent than the two versus one. The results for single disk extraction was within the realm expected for DNA yields from 13 uL of whole blood as estimated by PCR.

FIG. 6:

Electrophoretic analysis with 2% SFR agarose gel of PCR products generated from the DNA extracted from whole blood extracted with SDS using phosphate/fluoride treated kaolin (Example 11) as described in Example 47. The PCR amplicon is a 558 bp fragment from human amylogenin gene. The extraction process as described in "Example 28" based on 2% sodium dodecyl sulfate (SDS) and extract DNA from the following sample volumes of whole blood (frozen then thawed) 0.05 ul, 0.5 uL, 1 uL, 5 uL, and 50 uL. The samples from 1 uL of whole blood used Savanase at the protease where the other samples used proteinase K.

Figure 6:
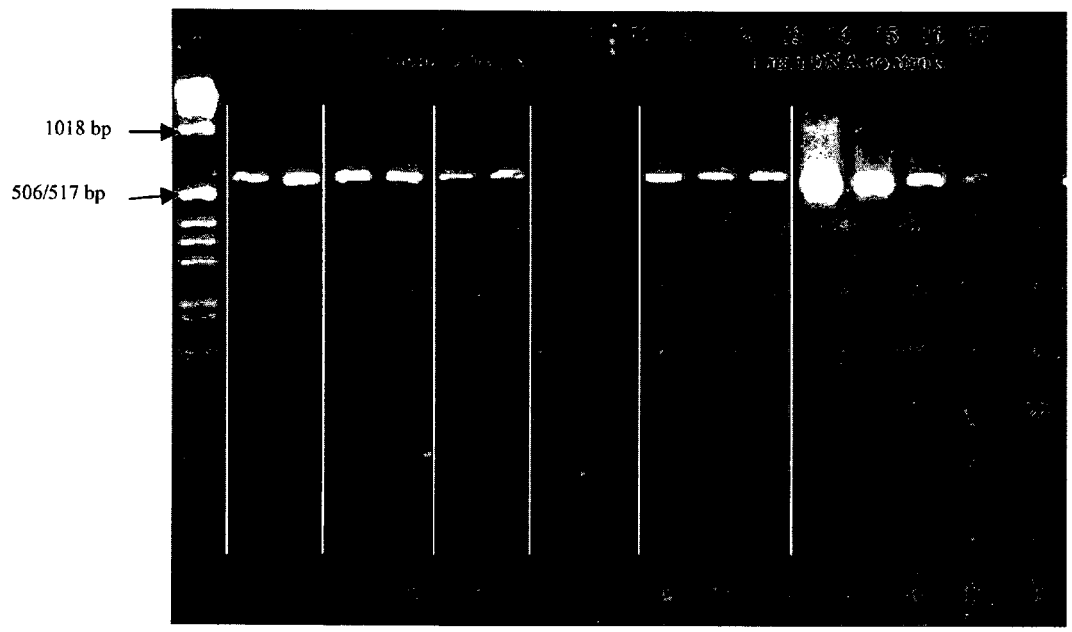
FIG. 6:
Electrophoretic analysis with 2% SFR agarose gel of PCR products generated from the DNA extracted from whole blood with SDS using phosphate/fluoride treated kaolin (Example 11). The PCR amplicon is a 558 by fragment from human amylogenin gene. (See Example 48).

As illustrated in FIG. 6, lanes 13 through 17 are the human DNA controls that contain a known quantity of DNA. The amounts were 10 ng (lane 13), 1 ng (lane 14), 0.1 ng (lane 15), and 0.01 ng (lane 16). The PCR product of the reaction displayed in lane 17 is the null control, that is the reaction that is done without any template DNA added. The PCR products from the blood extracts are displayed in lanes 2 through 12. Lanes 2 and 3 are the products from an extract of 50 uL of whole blood, in which 1 uL of the DNA eluate of 150 uL, was diluted 1:19, and 1 uL of that dilution was added to the PCR as the template source. Lanes 4 and 5 are the product from an extract of 5 uL of whole blood, in which 1 uL of the DNA eluate of 50 uL, was diluted 1:5, and 1 uL of that dilution was added to the PCR as the template source. Lanes 6 and 7 are the products from an extract of 0.5 uL of whole blood, in which 1 uL of the DNA eluate of 25 uL was added to the PCR as the template source. Lanes 8 and 9 are the products from an extract of 0.05 uL of whole blood, in which 8 uL of the DNA eluate of 25 uL was added to the PCR as the template source. Lanes 10, 11 and 12 are the product from an extract of 1 uL of whole blood, in which 1 uL of the DNA eluate of 25 uL, was diluted 1:1, and 1 uL of that dilution was added to the PCR as the template source.

Each lane represents one fifth of the PCR product, 5 uL from 25 uL PCR reaction. Lane 1 is 1 ug of the 1 kb dsDNA molecular size ladder. For all samples except extracts used for lanes 10 and 11, the DNA adsorption process was to use 1 volume of ethanol and to wash the particle in 50% ethanol with 100 mM NaCl. For the extract analyzed in lane 10, the process differed in the particle alcohol wash step, in which the solution was 66% ethanol with 100 mM NaCl. For the extract analyzed in lane 11, the process differed in which adsorption was with 1 volume of isopropanol the wash step was like the majority of the samples, 50% ethanol with 100 mM NaCl.

Figure 7:
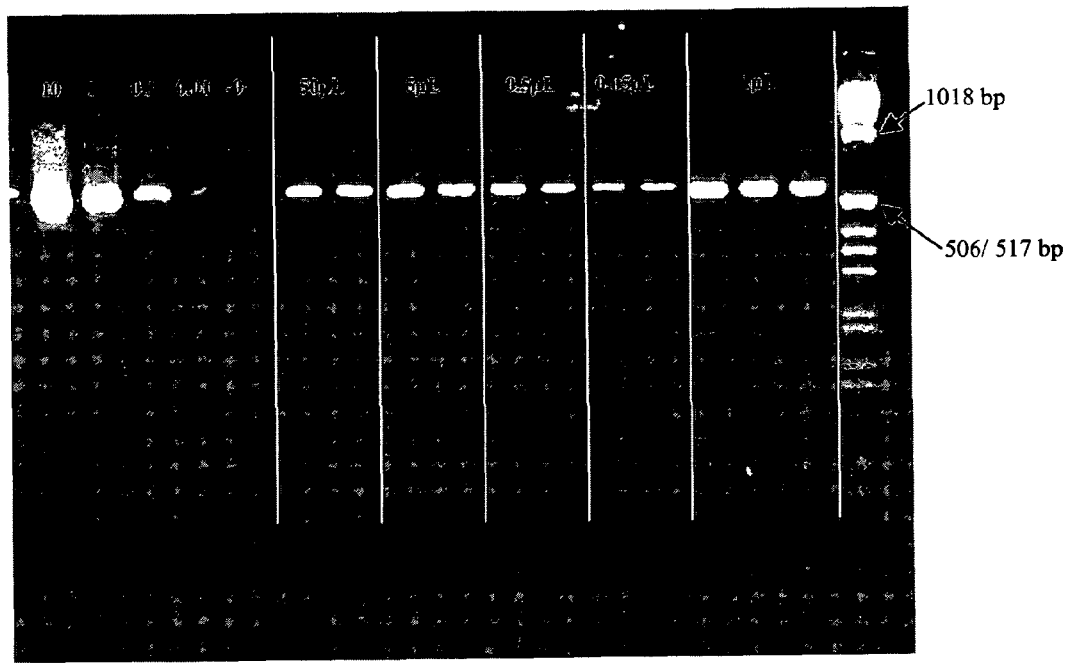
FIG. 7:
Electrophoretic analysis with 2% SFR agarose gel of PCR products generated from the DNA extracted from whole blood with sodium lauroyl sarcosine and guanidine hydrochloride using phosphate/fluoride treated kaolin (Example 11). The PCR amplicon is a 558 by fragment from human amylogenin gene. (See Example 47).

FIG. 7:

Electrophoretic analysis with 2% SFR agarose gel of PCR products generated from the DNA extracted from whole blood with sodium lauroyl sarcosine and guanidine hydrochloride using phosphate/fluoride treated kaolin (Example 11). The PCR amplicon is a 558 bp fragment from human amylogenin gene. The extraction process as described in "Example 29" based on 1% sodium lauryol sarcosine and 900 mM guanidine hydrochloride, was use to extract DNA from the following sample volumes of whole blood (frozen then thawed) 0.05 ul, 0.5 uL, 1 uL, 5 uL, and 50 uL. The samples from 1 uL of whole blood used Savanase at the protease where the other samples used proteinase K. As illustrated in FIG. 7, lanes 1 through 4 are the human DNA controls and contain a known amount of DNA. The amounts were 10 ng (lane 1), 1 ng (lane 2), 0.1 ng (lane 3), and 0.01 ng (lane 4). The PCR product of the reaction displayed in lane 5 is the null control, that is the reaction that is done without any template DNA added. The PCR products from the blood extracts are displayed in lanes 6 through 16. Lanes 6 and 7 are the product from an extract of 50 uL of whole blood, in which 1 uL of the DNA eluate of 150 uL, was diluted 1:19, and 1 uL of that dilution was added to the PCR as the template source. Lanes 8 and 9 are the product from an extract of 5 uL of whole blood, in which 1 uL of the DNA eluate of 50 uL, was diluted 1:5, and 1 uL of that dilution was added to the PCR as the template source. Lanes 10 and 11 are the PCR-product from an extract of 0.5 uL of whole blood, in which 1 uL of the DNA eluate of 25 uL was added to the PCR as the template source. Lanes 12 and 13 are the PCR-product from an extract of 0.05 uL of whole blood, in which 8 uL of the DNA eluate of 25 uL was added to the PCR as the template source. Lanes 14, 15 and 16 are the product from an extract of 1 uL of whole blood, in which 1 uL of the DNA eluate of 25 uL, was diluted 1:1, and 1 uL of that dilution was added to the PCR as the template source. Each lane represents one fifth of the PCR product, 5 uL from 25 uL PCR reaction. Lane 17 1 ug of the 1 kb dsDNA molecular size ladder. For all samples except extracts used for lanes 14 and 15, the DNA adsorption process was to use 1 volume of isopropanol and to wash the particle in 50% ethanol with 100 mM NaCL. For the extract analysed in lane 14, the process differed in the particle alcohol wash step, in which the solution was 66% ethanol with 100 mM NaCl. For the extract analyzed in lane 15, the process differed in which adsorption was with 1 volume of ethanol the wash step was like the majority of the samples, 50% ethanol with 100 mM NaCL.

Figure 8:
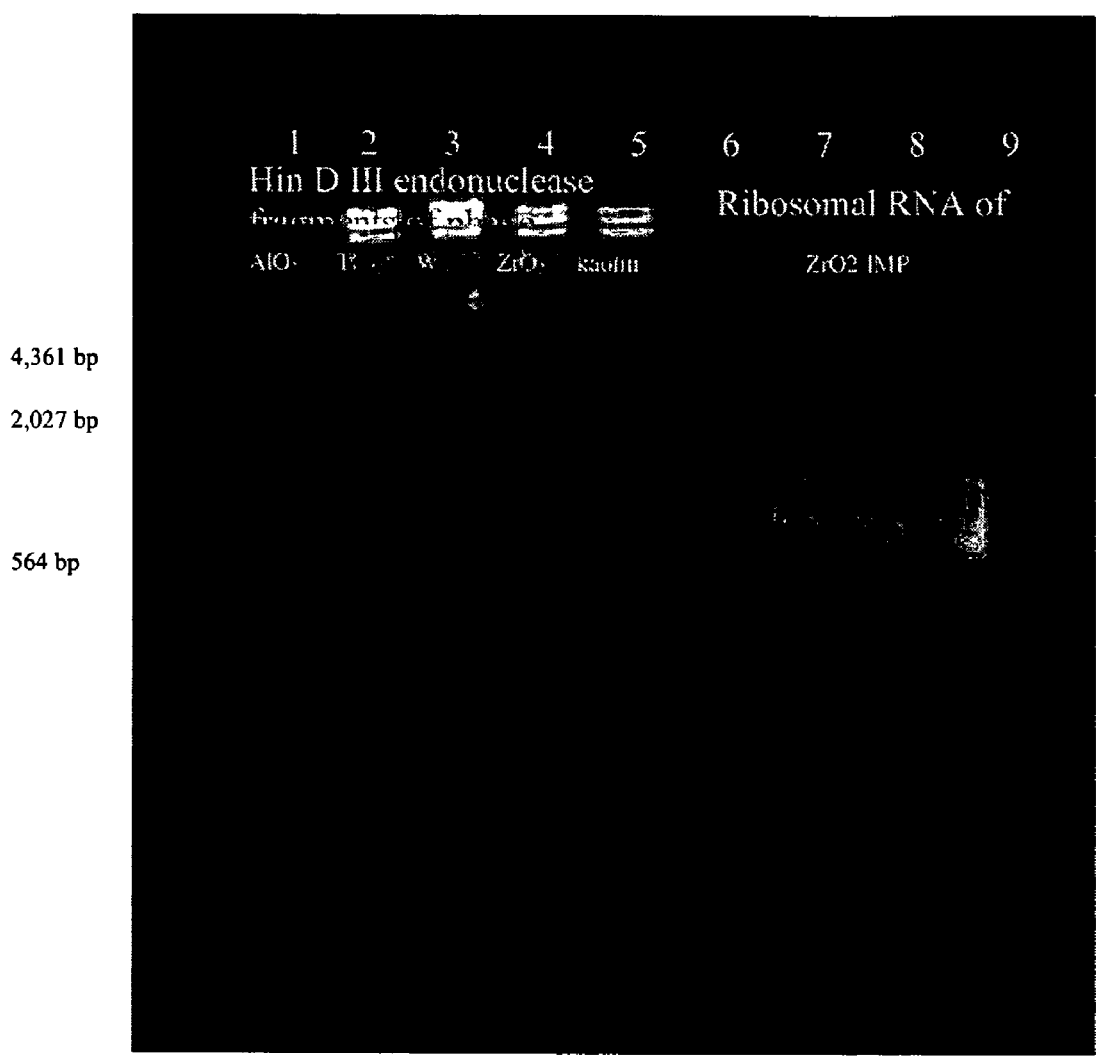
FIG. 8:
Electrophoretic analysis of DNA adsorption using borate treated metal oxides, of aluminum, zirconium, titanium, or tungsten and phosphate/fluoride treated kaolin (lanes 1-5, see Example 49) and the RNA adsorption to inosine monophosphate coated zirconium oxide (lanes 7-9, see Example 32).

FIG. 8:

Gel analysis of samples as described in Examples 49 and 32. FIG. 8 illustrated two Examples; Example 49 (lanes 1 through 5), the DNA adsorption using borate treated metal oxides, of aluminum zirconium, titanium, or tungsten and phosphate/fluoride treated kaolin, and Example 32 (lanes 7 through 9) the RNA adsorption to inosine monophosphate (IMP) coated zirconium oxide.

For Example 49, half of the DNA adsorbed to the particles was analyzed by agarose gel electrophoresis. The sample DNA, DNA fragments from lambda phage DNA digested with restriction endonuclease HinD III, were concentrated by the nanoparticle adsorption process as described in Example 26, though DNA in lanes 1 through 4 used different borate treated nanoparticles as the adsorption-platform. The DNA eluate displayed in lane 5 was the result of the process describe in Example 26 using phosphate treated kaolin (Example 11). The respective nanoparticle platforms were aluminum oxide lane 1 (~43 nm), titanium oxide lane 2 (~50), tungsten oxide lane 3 (~35 nm), zirconium oxide lane 4 (~25 nm), all compared to 200 nm phosphate treated kaolin.

For example 32, the process was to induce *E. coli* rRNA to adsorb to inosine monophosphate coated zirconium oxide (Example 23). The adsorption process to inosine monophosphate (IMP) coated zirconium oxide nanoparticle was to add 5 uL of a 2 ug solution of rRNA (*E. coli*) to 50 uL solution containing 0.1% sodium lauroyl sarcosine, 1.0M LiCl, 20 mM Tris-OH/Tris-HCl (pH 8), 2 mM EDTA for sample displayed in lane 7, for sample displayed in lane 8 the same as lane 7 sample only with the 20% formamide, for the sample displayed in lane 9 the same as in lane 7 only with the addition of guanidine hydrochloride (Gu-HCl) to 600 mM. To this was added 20 uL of IMP-$ZrO_2$ suspension (~1 mg). The suspension was incubated for 30 min, then centrifuged for 4 min at 2000 G the supernatants were removed from the pelleted particles. These particles were resuspended in 200 uL of 1× binding solution (0.1% sodium lauroyl sarcosine, 0.5M LiCl, 10 mM Tris-OH/Tris-HCl (pH 8), 1 mM EDTA. These suspension were then subjected of centrifugation for 2 min at 2000 G, the pellet was retained the supernatant were discarded. The pellets were resuspended in elution buffer of 50% formamide, 10 mM Borate buffer (pH~9.2), 10 mM Tris, 4 mM acetic acid, 20 mM NaCl, 2 mM phosphate buffer and were incubated in this for 30 min. Half of the eluates were analyzed by 1% agarose TBE gel.

FIG. 9:

Gel analysis of DNA isolated from a buccal cell sample collected by swabs. DNA isolated from buccal cell sample using Fitzco swab collection. Buccal cells were harvested from three human volunteers, A through C, two samples per subject. Half of the samples collected from each subject were extracted using Tween-20 as the detergent and the othe half were extracted using SDS as the detergent. The two extraction processes were as describe in Example 47 with proteinase K with the exception of substituting Tween-20 for half of the samples. The nanoparticle adsorption process was as described in Example 26 with the DNA eluted in a total volume of 25 μL. The PCR process analysed 0.5 μL of the DNA eluate from each sample using primers against the chromosomal allele GSTpi which yields a PCR amplicon product of 330 bp length. For the TBE, 2% SFR agarose gel, 5 uL of the PCR reaction was analysed per well. The products analysed in lanes 1 through 3 were extracted with Tween-20 detergent, and for lanes 4 through 6 were extracted with SDS.

Lanes 7 though 10 were the PCR products from the human DNA controls; lane 7 product from a PCR reaction started with 10 nanograms of DNA, lane 8 product from a PCR reaction started with 1 nanograms of DNA lane 9 product from a PCR reaction started with 0.1 nanograms of DNA, lane 10 product from a PCR reaction started with 0.01 nanograms of DNA PCR products analysed in lane 11 are the DNA null control, or reaction in which no DNA was added. Lane 12 is the molecular weight DNA ladder of 1 kb and smaller fragments. For this analysis only one quarter of the buccal sample was processed, the estimation, based on the human DNA controls was that the yield per sample (¼) was between 100 to 500 ng, or 400 to 2000 ng per total sample, a range typical for buccal cheek swabs.

FIG. 10:

Silver stain of 3-8% Tris-acetate gel polyacrylamide gel of proteins that bound to kaolin nanoparticle with the epoxy-silane-DTT-DVS thiophilic ligand. Two types of particles were tested, M-type and P-type on two sources of immuno-globulin, serum or saliva. The "M-type" particles were the epoxy-silane-DTT-DVS ligand terminated with mercaptoethanol and the "P-type" particles were the epoxy-silane-DTT-DVS ligand terminated with propylene glycol sample represents $1/60^{th}$ of the eluate from these thiophilic ligand coated particles (See Example 15). The process was that described in Example 44 for serum samples and Example 46 for saliva samples. Three concentrations of particles were used for the serum samples, 5 uL vs 10 uL or 20 uL of 50 mg/mL suspension of the nanoparticle suspension, added to 500 uL of diluted sample. For the salivary samples 20 uL of thiophilic ligand coated nanoparticle suspension was used per 0.5 mL mouth rinse of saline wash. The samples were "lane MW", the protein molecular weight standards, with size indicated with the arrows. For "lane 1", serum sample of 1 uL of serum in 0.5 mL of PBS and 5 ul of P-type particle slurry was used, for "lane 2", serum sample of 1 uL of serum in 0.5 mL of PBS and 10 ul of P-type particle slurry was used, and for "lane 3", serum sample of 1 uL of serum in 0.5 mL of PBS and 20 ul of P-type particle slurry was used. For "lane 4", serum sample of 1 uL of serum in 0.5 mL of PBS and 5 ul of M-type particle slurry was used, for "lane 5", serum sample of 1 uL of serum in 0.5 mL of PBS and 10 ul of M-type particle slurry was used, and for "lane 6", serum sample of 1 uL of serum in 0.5 mL of PBS and 20 ul of M-type particle slurry was used. For lanes 7 through 11, the sample was saliva with the process as describe in Example 45, for "lane 7", 0.5 mL of mouth-saline rinse-ate subject #1 and 20 ul of P-type particle were used., for "lane 8", 0.5 mL of mouth-saline rinse-ate subject #2 and 20 ul of P-type particle were used., and for "lane 9", 0.5 mL of mouth-saline rinse-ate from subject #3 and 20 ul of P-type particle were used. For "lane 10", 0.5 mL of mouth-saline rinse-ate subject #1 and 20 ul of M-type particle were used and for "lane 11", 0.5 mL of mouth-saline rinse-ate subject #2 and 20 ul of M-type particle were used.

FIG. 11:

Chromatography of Serum Proteins with Cibacron blue-amino-silane coated nanoparticles. The analysis of the results are displayed in the silver stain 3-8% Tris-acetate gel polyacrylamide gel. The serum proteins were fractionated with Cibacron Blue, amino-silane coated nanoparticles in PBS. The protein chromatography with nanoparticles described in Example 18 using the chromatographic process described in Example 36. The nanoparticles were used at two concentrations, for samples displayed in lanes 1 through 5, 5 uL of nanoparticle slurry was used for the protein chromatography as displayed in lanes 6 through 10, 20 uL of nanoparticle slurry was used for the protein chromatography. All the particles were first coated with amino-silane, Example 16 and Example 17. The Cibacron blue was bound to this amino-silane surface by the process in Example 18. The samples were isolated using the following coated nanoparticles; ~50 nm diameter titanium oxide (lanes 1 and 6), ~25 nm diameter zirconium oxide (lanes 2 and 7), ~200 nm diameter kaolin (lanes 3 and 8), ~35 nm diameter tungsten oxide (lanes 4 and 9), and ~45 nm diameter aluminum oxide (lanes 5 and 10). The sample displayed in lane "C" is unfractionated serum at the same concentration as the incoming material.

DETAILED DESCRIPTION OF THE INVENTION

The present invention is directed to nanoparticles activated by a biopolymer binding reagent for manipulation of biopolymers such as those discussed above, compositions comprising such activated nanoparticles, methods for their use, and kits comprising these activated nanoparticles for performing these methods. As will be discussed in detail below, these compositions, methods, and kits have a number of advantages over conventional compositions and techniques for manipulating biopolymers, including, for example, ease of use, simplicity of equipment required, cost, amount of material recoverable, and concentration of material of interest.

The term "biopolymers" is expressly intended to include both short and long biopolymers, including, but not limited to such polymeric molecules as DNA, RNA, proteins, immunoglobulins or carbohydrates. Thus, for example, the term includes both short (oligomeric) and long nucleic acid molecules, and similarly encompasses both small protein sequences (peptides) as well as longer polypeptides. The skilled artisan will understand that different biopolymers may require different activated nanoparticles, i.e., different nanoparticles as well as different chemical properties for such nanoparticles obtained by the use of an appropriate biopolymer binding agent. The selection by the skilled artisan of a particular activated nanoparticle for a particular biopolymer will be made based on an understanding of the present invention as illustrated throughout this application, as well as by the specific examples of the use of particular nanoparticles for particular applications given elsewhere herein.

The term "metals" are defined from the element group selected from the Transition Metals including the Lanthanide group. The semi-metals are from Group III and non-metal elements are from Group IV, Group V elements.

"Glasses" are defined as non-crystalline solids with an amorphous molecular arrangement or a non-structured molecular lattice.

The term "clay" is defined as naturally derived crystalline mineral mixtures with consisting of a crystalline molecular lattices held together with covalent, ionic, or coordinate bonds or a mixture thereof, one or a mixture of elements selected from Group I, Group II, Transition Metals Group III, Group IV, Group V, or Group VI, Group VII.

The term "crystal" is defined as a regular covalent arranged molecular array or structured molecular lattice comprising of Transition Metals or the elements from Group III, Group IV, Group V, and Group VI, either as pure elements or as mixtures thereof.

The term "ceramic" is defined as an inorganic crystalline molecular solid with non-metallic properties comprising of elements from the following Group I, Group II, Transition Metals Group III, Group IV, Group V, or Group VI, Group VII and mixtures including such elements.

As used herein, "activated" is intended to refer to nanoparticles that have been altered so as to enhance their ability to bind (reversibly or irreversibly) one or more classes of biopolymer, where "altered" is intended to encompass both chemical modifications such as cross-linking as well as electrostatic or other non-covalent changes or additions to the non-activated nanoparticles to render them activated. Thus, for example the present invention contemplates nanoparticles that have been activated so as to enhance their ability to reversibly bind DNA for purification and concentration procedures, as discussed elsewhere herein with regard to the "flocculation chromatography" aspect of the present invention.

The term "manipulation of biopolymers," as used herein, refers to any of the various actions that may be performed on a biopolymer bound to the activated nanoparticles of the present invention, with binding contemplated to include both reversible and essentially irreversible binding. Thus, for example, binding of a biopolymer to activated nanoparticles may be used as the basis of immobilizing a biopolymer, e.g., when the biopolymer is applied to a sheet of appropriate material coated with a layer of activated nanoparticles. The skilled artisan will understand that such immobilization has utility in, for example, screening or detection methods. Such immobilization may also be used for archival storage of biopolymer, e.g., for storage of stock DNA for later use, for storage of patient reference DNA for later analysis, etc. Other manipulations contemplated herein based on the binding properties of the activated nanoparticles of the invention include the separation, purification, or concentration of biopolymers, as discussed elsewhere herein.

As used herein, the term "nanoparticle," refers to a particle having an area to volume ratio of at least 6 mm$^2$/ml, and a sedimentation rate at one times gravitational force (1G) of at least about 6×10$^{-4}$ cm/hr and no more than about 0.25 cm/hr. Such nanoparticles have a large surface area per unit volume or unit mass, thus offering up a large surface area for activation by a biopolymer binding agent. Thus in light of this large surface area per unit volume or unit mass, the resulting activated nanoparticles of the invention are able to bind large amounts of biopolymer relative to the unit volume or unit mass of activated nanoparticles used, allowing for advantageous characteristics of these activated nanoparticles, including, e.g., the ability to recover greater amounts of biopolymer material with these activated nanoparticles. Other advantageous properties deriving from the use of the activated nanoparticles of the present invention are discussed elsewhere herein, e.g., the ability of such activated nanoparticles to exist in colloidal form (i.e., to remain suspended in aqueous phase for a long period of time without settling) and, upon binding biopolymers, to form flocculates capable of being concentrated by low-speed centrifugation or by settling under conditions of normal gravity (i.e., "flocculation chromatography"; see below).

The present invention contemplates nanoparticles comprising a variety of substances. In general any material that may be routinely obtained with a largest linear dimension of less than about 1 μm ("sub-micron") and which has the appropriate chemical properties for activation is contemplated as being within the scope of the nanoparticles of the present invention. Within this genus, the present invention contemplates as being particularly useful those nanoparticles comprising substances that are sufficiently robust, inert, and inexpensive. Thus the present invention contemplates nanoparticles as including, generally, metallic, semi-metallic, and non-metallic nanoparticles, including ceramics, clays, carbon-backboned or composites, and, within this genus, contemplates as being particularly useful nanoparticles composed of kaolin clays. One embodiment of the present invention is directed to clay nanoparticles, and in particular to smectic clay nanoparticles such as kaolin clay nanoparticles.

In one embodiment, the invention is solid-phase, non-porous particles for manipulating of biomolecules, comprising a surface area to volume ratio (m$^2$/cm$^3$) greater than 10, and a density (ρ) greater than 2, and having sedimentation rates in water, with $V_{min}$ greater than 0.1 cm/min at 10,000 G and $V_{max}$ less than 2 cm/min at 500 G at standard temperature and pressures. In another embodiment of the invention, the particles have a density greater than about 2 less than or equal to about 2.5, and effective spherical diameters as determined by two times Stokes radius in the range of 60 nm to 1000 nm. In yet another embodiment, particles have having a density greater than about 2.5 less than or equal to about 3 and effective spherical diameters as determined by two times Stokes radius in the range of 40 nm to 800 nm. In yet another embodiment, the particles have a density between about 3 to less than or equal to about 3.5 and effective spherical diameters as determined by two times Stokes radius between about 35 nm to 400 nm. In yet another embodiment, the particles have a density greater than about 3.5 to less than or equal to about 4, and effective spherical diameters as determined by two times Stokes radius between about 20 nm to about 700 nm. In yet another embodiment, the particles have a density greater than about 4 to less than or equal to about 4.5, and effective spherical diameters as determined by two times Stokes radius between about 30 nm to about 600 nm. In yet another embodiment, the particles have a density greater than about 4.5 to less than or equal to about 5, and effective spherical diameters as determined by two times Stokes radius between about 25 nm to about 550 nm. In yet another embodiment, the particles have a density greater than about 5 to less than or equal to about 5.5, and effective spherical diameters as determined by two times Stokes radius between about 25 nm to about 500 nm. In yet another embodiment, the particles have a density greater than about 5.5 to less than or equal to about 6, and effective spherical diameters as determined by two times Stokes radius between about 25 nm to about 450 nm. In yet another embodiment, the particles have a density greater than about 6 to less than or equal to about 6.5, and effective spherical diameters as determined by two times Stokes radius between about 20 nm to about 450 nm. In yet another embodiment, the particles have a density greater than about 6.5 to less than or equal to about 7, and effective spherical diameters as determined by two times Stokes radius between about 20 nm to about 400 nm. In yet another embodiment, the particles have a density greater than about 7 to less than or equal to about 7.5, and effective spherical diameters as determined by two times Stokes radius between about 20 nm to about 400 nm,. In yet another embodiment, the particles have a density greater than about 7.5 to less than or equal to about 14, and effective spherical diameters as determined by two times Stokes radius between about 15 nm to about 300 nm. In yet another embodiment, the particles have a density greater than about 14 to less than or equal to about 20, and effective spherical diameters as determined by two times Stokes radius between about 12 nm to about 240 nm.

In one embodiment, the invention comprises solid-phase particles for manipulating biomolecules using as a colloidal suspension in a liquid phase. The solid-phase particles are comprised of crystalline, amorphous or polymer structures, or mixtures thereof. The sedimentation rate of the solid-phase particles, in water or a similar liquid phase at one times gravitation force (1G) is less than about 0.25 cm per hour and greater than about 6×10$^{-5}$ cm per hour at one times gravitational force (1G). The solid-phase particles are chemically stable under the conditions necessary for particle modification or for biomolecule manipulations with the particles. The surface area to volume ratio of the solid-phase particles is greater than about 6 cm$^2$ per cubic centimeter and less than about 200 cm$^2$ per cubic centimeter. These solid-phase particles have little to no reactivity with the liquid-phase of the colloidal suspension.

In an embodiment of the invention the solid particles are composed of elements comprising of metals, semi-metals, or non metals and their corresponding oxides, carbides, hydroxides, nitrides, phosphates, alloys, ceramic mixtures, clays, glasses, crystals and or mixtures thereof.

In another embodiment, the solid-phase particles are made of linear or branched polymers with elements from Group III, Group IV, Group V, and Group VI including those composed of carbon, germanium, or silicon. The solid phase particles can be composed of naturally derived particles of aluminosilicate composition of the kaolinite or smectite clays such as kaolin or bentonite, respectively.

One of the embodiments of this invention is a method of manipulating biomolecules with solid-phase particles in colloidal suspension in which the concentration of solid-phase particles in colloidal suspension, as defined by the dry weight of particle per unit volume of suspension, would be a range of about 10% or less, in which most applications would be with colloidal suspensions at a particle concentration of about 5% or less, with the desired particle concentration be within a range between about 0.1% to 1%.

In another embodiment of the invention, the method for manipulating biomolecules comprises using solid-phase particles in colloidal suspension, the solid-phase particles are chemically coated with molecular layers to confer additional chemical properties. The chemical properties allow for the binding of other molecular layers. The chemical properties of a coating are such that these coating molecules have a unique affinity for a specific type or class of biomolecules. The affinity is determined by conditions such as range of ionic concentration, specific classes or types of ionic species, or specific range of pH, or in the absence of a molecule that would compete for the biomolecule binding. The release or disassociation of the targeted biomolecule is accomplished by methods known for the biomolecule and the binding ligand of the affinity coating, for example changes in specific ion concentration, either increase or decrease, from binding conditions, or by a change in pH, or by the addition of a competing molecule, or a combination thereof.

In another embodiment, the invention is a method of affinity chromatography performed with solid-phase particles in colloidal suspension that comprises the interaction of the solid-phase particles within a mixture of biomolecules under conditions that cause a specific biomolecule to absorb to the surface of the solid-phase particle. The methods of separating these solid-phase particles as described above subsequent to biomolecule binding, from the liquid phase and resulting in the isolation of the biomolecules from the suspension medium, to form a stable compacted slurry enriched for the biomolecule, comprise centrifugation in which the centrifugal field strength is at or less than 10,000 G and is applied for one hour or less, or filtration in which the filter's pores are of a dimension to exclude the solid phase manipulations though allow the liquid phase to pass through, upon such solid-phase particles, or by the method flocculation in which the particle-biomolecule complex forms aggregates that have a greater sedimentation rate and size that can no longer stay in suspension or if the aggregation is induced after biomolecule complexes are formed by the introduction of a flocculation agent that induced the particles to form aggregates with the biomolecule attached, or a mixture of these methods.

In another variation of the invention, the biomolecule or biomolecule set used in the affinity chromatography are nucleic acids and where the conditions of binding to the solid-phase particle result from either salt or organic solvent concentrations, or a combination of both in the fluid phase that are known to reduce the solubility of the nucleic acid in aqueous solution. The biomolecule or biomolecule grouping can also be a nucleic acid polymer of DNA or RNA, where binding results from addition of alcohol to the aqueous fluid phase of the suspension to produce an alcohol/water volume ratio greater than about 30%. The ions for nucleic acid precipitation can be from the cations from Group I or Group II elements such as, but not limited to, Li, Na, K, Cs, Mg, Ca, Sr, and Ba.

The biomolecule or biomolecule set in the affinity chromatography can be proteins where the conditions of binding are the result of either salt or organic solvent concentrations, or a mixture thereof, that are known to reduce the solubility of protein(s) in aqueous solution. The protein precipitation salts may have anions from, but not limited to, halogen ions, sulfates, or tricholoroacetates. The uncoated surface of the solid-phase particle can have an affinity for the targeted biomolecule by an ionic, hydrophobic, or electron-donor-acceptor interaction with examples being hydroxyapatite, aluminum oxide, or zirconium phosphate.

Another embodiment of the invention is a method of biochemical manipulation with solid-phase coated particles in colloidal suspension with the particle coatings comprised of organosilane, in which the coatings remain associated with the particle by covalent bonds, or by encapsulating the particle, or by some combination of encapsulation and covalent linkage. The coatings can be comprised of the polymerized monomers of trimethoxysilanes, or triethoxysilanes, or mixtures thereof. These trimethoxysilanes or triethoxysilanes include reactive moieties to confer desired surface chemistry to solid-phase particles or properties of affinity ligands. The reactive moieties can be utilized as linkers for further coupling sites of additional molecular coatings. These reactive moieties can be selected from silane groups such as from the amino-silanes", for example 3-aminopropyl-triethoxysilane, or from the "epoxy-silanes", for example of 3-glycidyloxypropyltriethoxysilane, or from the "alkyl-silanes", with the examples of octyltriethoxysilane, butyltriethoxysilane, ethyltriethoxysilane, or from the "mercapto-silanes" for example 3-mercaptopropyltriethoxysilane, or from other organaosilanes with reactive groups which contain reactive styrenes, acrylamides, or vinyls, as well as other reactive moieties that are linked to an organosilane monomers.

The molecular coatings for solid-phase particles in which the primary layer is amino-silane which can act as a cationic affinity layer for anionic biomolecules or as a linker to a second layer of molecular coating by amine-reactive chemistries such as anhydrides, divinyl sulfone, hydrazides, triazines, or by reductive amination with carboxylates, aldehydes and ketones, or the alkylation chemistry of haloalkyls or haloacetates, or by carbodiimide activated molecules such as hydroxyls, aldehydes or carboxylate, or by aldehyde mediated reactions by Mannich condensation.

Epoxy-silane layer of molecular coatings for solid-phase particles can be modified by acid mediated reduction to cis-diols followed by periodate oxidation to form silane bound aldehydes. The aldehydes can link to nucleic acids or proteins. The linkage of these biomolecules can be through reductive amination. The linkage to these biomolecules can also be through phosphates or amines by carbodiimide mediated reactions.

The second layer of molecular coatings for solid-phase particles can be linked with epoxy-silane layer by epoxy reactive groups such as amines, hydroxyls or thiols moieties. Through amine linkages the second layer can be selected from polyamines such as linear or branched polymers of polyethylenimine, polylysine, peptides, proteins, chitins, chitosans, or smaller molecules such as diaminoethane, diaminodipropylamine, spermidine, lysine, or any mixture of the above mentioned molecular species. One polyamine in particular, as an example, can be the polyethylenimine. The polymers can have molecular sizes ranging from 600 to 750,000 Daltons, in which the polyamine layer can be used as an affinity ligand for anionic molecules or as a molecular linker for other molecular coatings. Through hydroxyl linkages the second layer can be selected from polymers such as oligo- or polysaccharides, glycoproteins, glycolipids, or synthetic hydroxyl rich polymers such as polyalcohols, dextran sulfates, heparin, polyethylene glycol, to name a few. Through thiol linkages the second layer can be selected from cystein containing peptides or proteins, or to numerous types of mercaptans, to thiophosphorylated oligo- or polynucleotide polymers.

Molecular coatings for solid-phase particles in which linked to epoxy-silane layer by the linked polyamine molecular coatings are a third layer of molecular coatings by amine reactive groups or chemistries, such as anhydrides, divinyl sulfone, hydrazides, or triazines, or by reductive amination, or the halo-alkylation, or the by carbodiimide mediated reactions with hydroxyls, aldehydes or carboxylates, or by the aldehyde mediated reactions of Mannich condensation.

In molecular coatings for solid-phase particles, the primary amines of these coatings are further linked with bifunctional reagents of aldehyde group such as glutaraldehyde, to be a subsequent linker to bind an additional coating, a molecule that has a reactive amine, molecules such as amino acids, amino mercaptans, polypeptides, proteins, or amine modified oligo or poly nucleotides.

In another embodiment, the primary amines of the molecular coatings for solid-phase particles are further linked with a bifunctional reagents of divinyl sulfone, in which the divinyl sulfone will be a subsequent linker to bind an additional molecular coating, molecule that has a reactive amine or thiol group, molecules such as mercaptans, polypeptides, proteins, or thiol or amine modified nucleotide polymers.

In yet another embodiment, the molecular coatings for solid-phase particles can be divinyl sulfone containing ligands for performing the method of electron-donor-acceptor affinity chromatography for immunoglobulins and immunoglobulin related proteins, in which the ligand consists of divinyl sulfone linked to a mercaptan, such as 2-mercaptoethanol, mercaptopurine, mercaptopyrimidine, mercaptophenol, aminothiophenol, and other similar compounds. The method of affinity chromatography is performed with the matrix (coated solid-phase particle) in a colloidal suspension. The sources for the suspension extract are from serum, saliva, milk, colostrum, eggs, and other bodily fluids, tissue culture supernatants, or extracts from other animal, bacterial, yeast, or plant sources.

Another embodiment of the invention includes the reagents, analytical products and kits containing immunoglobulins isolated and enriched by the methods developed for disease diagnosis, disease management, or for the development or for the manufacture of pharmaceuticals, or for the manufacture of immunoglobulin based affinity ligands, immunoglobulin analytes, for the isolation or detection of chemical haptens or epitopes, or for the isolation of antigens molecules, cells, organelles, viruses, capture of antibodies bound to targeted biological entity by the use of solid-phase particles, or for the evaluation or diagnosis of infectious and non-infectious disease, or for the monitoring or evaluating the effectiveness of drugs or vaccines, or for the screening or detection of drugs, or as reagent incorporated components into kit or devices which utilize immunoglobulin binding.

In one embodiment, molecular coatings are linked through amine-containing coating of solid-phase particles based on triazene chemistry, in which triazene is used as a trifunctional linker to bind additional molecular coatings such as amino acids, proteins, enzymes, polyamines, polycyclic amines, amine modified oligo- or poly nucleotide polymers or in which the ligands contain a triazene ring(s) such as the dyes including Cibacron Blue F3GA or Procion Red HE-3B.

In another aspect of molecular coatings for solid-phase particles, an additional layer of molecular coating is linked between primary amine moieties bound to the particle with aldehyde containing molecular species, by reductive amination or by carbodiimide mediated chemistry. The aldehyde can be produced by oxidation of cis diols with periodate. The sources of the oxidized polysaccharide are from natural sources such as, but not limited to, agaroses, celluloses, chitins, dextrans, heparins, plant starches, glycogens, or synthetic derivatives thereof, or conjugates of polysaccharides with other biomolecules such as glycolipids, or glycoproteins, in which the glycoproteins can be selected from, but not limited to proteins such as enzymes, lectins, avidins, or immunoglobulins. The additional layer of molecular coating can be linked by Mannich condensation. Such molecular layers are selected from steroids, for example, digoxegenin, estrogen (and synthetic derivatives), or dyes such as thymol blue, phenol red, Coomasie blue.

In another embodiment, the invention is a method of affinity chromatography with coated particles in colloidal suspension in which these cationic amine containing coatings bind or have a strong affinity for anionic biomolecules such as nucleic acids, phosphorylated proteins, phosphorylated polysaccharides, phospholipids, heparin, or heparin analogue, dextran sulfate. The affinity ligand can bind to ribonucleotides or deoxyribonucleotides in the single-stranded, double-stranded, or as triple-stranded conformations or mixtures thereof. The nucleic acids used can be extracted from biological fluids in solutions comprising of a protease, chaotropic agents, non ionic detergents, and chelating agent such as EDTA. The chaotropic agents can be formamide, guanidinium salts, urea, or trichloroacetate salts, or mixtures thereof. The buffers can be chosen from the phosphate, acetate, Tris, MES, MOPS, HEPPS, HEPES, as chloride, or sodium salts, in which the pH is adjust to be with the range of pH 5 to pH 9 at concentrations within the range of 10 to 100 mM. The non-ionic detergents can be chosen from Triton X-100, Tween 20, NP-40 at concentrations within the range of approximately 0.1% wt to 2% by volume. The proteases can be subtilisins, proteinase K, chymotrypsin, trypsin, pepsin, papain, and bromelain. The biological samples can be isolated blood cells (buffy coat or gradient purified), whole blood, serum, saliva, sputum, vaginal/cervical scrapings or washes, mouth/throat swabs or washes, urine, lymph fluids, solid tissues, tissue biopsies, cell samples from tissue culture, microbial culture, yeast extracts, or plant extracts.

In another embodiment, the invention is a method of affinity chromatography with coated solid-phase particles in colloidal suspension with particles coated with affinity ligand of Cibacron Blue F3GA, in which the target biomolecule is albumin, and the method is either for the depletion or isolation, enrichment and concentration of albumin proteins from blood, serum, milk, eggs, or other bodily fluids, or the extracts derived from such fluids, thereof.

The epoxy-linked polyamine coating for solid-phase particles is further modified by alkylation reaction, i.e. haloalkylation, to form metal chelating ligands. The metal chelating ligand is formed from primary and secondary amines by the action of by chloroacetic acid or bromoacetic acid, whereas the metal ions for the affinity ligand are chosen from Transition Metals or Group II, Group III and Group IV metals with specific example of Al, Ca, Co, Cu, Fe, Ga, Mg, Mn, In, Ni, Ti, Zn. The metal chelated ligands are used to isolate, concentrate and enrich proteins or nucleic acids from biological sources, serum, blood, milk, saliva, vaginal/cervical swabs, or other bodily fluids, or from artificial sources; cell culture supernatants, yeast, plants, bacterial, or viruses.

In another embodiment of the invention, the biological extracts used in the method of affinity chromatography performed with coated particles in colloidal suspension are subjected to organic extraction prior to and subsequent to the addition of the particles and the nucleic acid-polyamine particle complexes are collected by sedimentation in which the particle-nucleic acid complexes are made to sediment through and organic solvent such as chloroform, fluorocarbons, mixed halogen carbon compounds such as bromofluorocarbons or chlorofluorocarbons. The polyamine coating of the coated particles in colloidal suspension can be polyethyelenimine. The conditions of release are accomplished by change in pH to alkaline conditions greater than pH 10, selected from a group of buffer agents but not limited to cycloaminopropylsulfonic acid, sodium carbonate, tri-basic phosphate, ethanol amine, or sodium hydroxide, at concentrations to shift the pH to be greater than 10. In another embodiment, the conditions of release of nucleic acid is accomplished by the addition of anionic detergents, selected from but not limited to alkali salts of dodecyl sulfate or sarkosyl, such as sodium salts, in which the detergents are in the range from about 0.01% (wt/vol) to saturation, in which most preferred concentration between about 0.1% (wt/vol) to 1.5% (wt/vol).

Another embodiment of the invention is a method of affinity chromatography performed with coated particles in colloidal suspension in which the polynucleotides, deoxyribonucleotides or ribonucleotides, are bound to the amine coated particle surface under conditions that favor denatured or single-stranded conformation. The binding of nucleic acid can be done in the presence of chaotropic compounds such as formamide, formaldehyde, urea, ethanol, guanidinium, or trichloroacetate salts and low salt buffers at concentrations that disrupt double and triple stranded annealing. The orientation of the single-stranded nucleic acids bound to the particle surface is such that these amine-bound, denatured nucleic acids are capable of annealing to form sequence specific duplexes or triplexes with a labeled or non labeled, target single-stranded or double-stranded nucleic acid polymers of RNA or DNA, or mixtures thereof.

The targeted nucleic acids can be either in solution phase or in solid-phase as bound to a particle in colloidal suspension, or in solid-phase as bound to a surface matrix that is not in suspension such as filters membranes or fibers, or solid-phase glass or plastic surface. The amine coated particles can be previously conjugated with a detectable label selected from one or a mixture and not limited chemical groups such as haptens or epitopes, biotin or biotin analogues, dyes, fluorescent dyes, fluorescent metal chelates, quantum dots, enzymes, peptides, binding proteins such as lectins, antibodies, or avidins. The multiple particles can also bind together to form complexes that are easily detectable or easily separated from the colloidal suspension with the biological source. The bound single-stranded polynucleotide is capable of annealing to double stranded target nucleic acids in a sequence specific manner in which the triple-strand is due to an annealing reaction of the single strand for purine-rich sequence of the double stranded target or the sequence specific triple stranded annealing is due to the particle bound single stranded DNA annealing to the complementary sequence of the double-stranded DNA target.

The particle-bound double-stranded nucleic acid can also anneal to the targeted single-stranded nucleic acids either in solution phase or in solid phase either on a colloidal suspended particle or in a solid phase not in suspension. The particle bound double-stranded nucleic acid can anneal the targeted single-stranded nucleic acid and by the formation of a sequence specific triple stranded structure either due to the annealing between the single stranded target to the purine-rich sequence of the double stranded nucleic acid or due to the annealing between the targeted single stranded DNA to the complementary sequence of the bound double-stranded DNA.

In a further embodiment of the invention, the ligand used in the method of affinity chromatography with solid-phase particles in suspension is single, a mixture, or a class of affinity ligands such as peptides, avidins, immunoglobulins or lectins or nucleic acids, in which these ligands are used for the isolation or detection of biomolecules, cells, or subcellular oraganelles, viruses, or microbes. The microbes used can be selected from but not limited to microbial species from the following genera such as *Bacillus, Chlamydia, Clostridium, Escherichia, Francisella, Giardia, Heliobacter, Microsporidium, Neisseria, Pneumococcus, Pneumocystis, Shigella* (and other pathogenic coliforms), *Staphlacoccus, Streptococcus, Treponema*. The coated particles in colloidal suspension may contain a complete or select portion of a combinatorial library with one biochemical sequence per particle in which the library can be composed of peptide, nucleotides, or oligosaccharides. The identity of the bound molecule or sequence can be determined by mass spectroscopy.

Another embodiment of the invention is a method of biochemical manipulation that uses solid-phase particles that has one or several enzymes bound to the coated surface for processing biological samples with a specific class of enzymes, or for detection chemistry use in diagnostic tests as an example. The method of detection chemistry is based on a set of enzymes that process a stable substrate to yield a detectable label, such as a set including phosphatases, oxidases, peroxidases, galactosidases, and amylases, or mixtures thereof, whereas the one of the enzymes generates a product from a stable substrate, and that product of the first enzyme is a substrate for a second enzyme that generates a product, with is reactive, or a substrate for a third enzyme, and the third enzyme utilizes this product of the second enzyme to produce a detectable label. The method of detection chemistry can be based on three enzymes only, in which the first enzyme can be an amylase, the second enzyme can be a glucose oxidase and the third enzyme can be a peroxidase, in which the detectable label producing cascade consists of soluble glucose polysaccharide that is the substrate for the amylase, which converts the starch to glucose, and the glucose, the substrate for glucose oxidase, causes the generation of peroxide, which is a key substrate peroxidase that will convert a dye to a detectable form, such as diaminobenzidine to an opaque, colored and water insoluble product. The final product can be a fluorescent dye. The enzyme containing particles can be conjugated to other binding ligands such as immunuglobulins, avidins, lectins, peptides, or oligonucleotides.

Manipulations of biomolecules using chemically coated solid-phase particles in colloidal suspension in which the enzymes are proteases selected from but not limited to proteinase K, substilisins, trypsin, chymotrypsin, bromelains, papains, and pepsins.

Thus one aspect of the present invention is directed to activated nanoparticles for the manipulation of biopolymers, i.e., for the purification, concentration, archival storage, etc. of biopolymers.

One of the preferred uses of this invention employs a cationic polymer, polyethylenimine (PEI), as a ligand coating to capture DNA or RNA. In the present invention, the PEI is linked to the surface of a sub-micron particle through covalent attachment via an activated surface film of epoxy-silane (3-glycidoxypropyl trimethoxy silane) using epoxy conjugation to the primary amines of the PEI, a well known conjugation chemistry to link any polyamine to a solid surface.

The surface bound PEI coating has a known affinity for DNA and RNA due to its complementary negative charge. In the present invention, once linked to the particle by complementary electrostatic attraction, DNA or RNA can be released from the PEI surface by increasing the pH above the collective pKa of the surface bound amines (See bibliography section called Patents) or by the addition of compounds such as ethanol amine, sodium dodecyl sulfate, or by 3-(cyclohexylamino)-1-propanesulfonic acid.

Procedures

DNA or RNA Sequence Specific Nucleic Acid Capture. For DNA/RNA sequence specific capture, many specific ligand surface coatings are known, such as amino phenylborate (to capture total RNA), polydT (to capture polyadenylated mRNA), or a specific gene sequence (as a bound single-stranded or double-stranded poly- or oligo-nucleotide bound to an amino-silane coated or PEI (low molecular weight) coated surface. These ligands have been described in the literature for having selective binding towards DNA or RNA on agarose bead substrates for chromatography, on magnetic beads for bulk purification, or on glass slides or beads in a microarray format. In one preferred implementation of the present invention, the surface coating for total RNA capture is PEI, which has been converted into the corresponding NHS ester then condensed with amino-phenylborate. Alternatively, for capture of polyadenylated RNA, the PEI surface coating is coupled to polydT via direct UV photochemical crosslinking or amino-silane coated surface binds polydT (or polydU or polyU). It is speculated that the cationic coatings on a sub-micron size clay particle will behave in a manner similar to the printed spot of probe bound to a glass slide. Thus for affinity to be sequence specific, the clay particles that have been coated with amino-silane or a low molecular weight polymer of PEI in which a poly- or oligonucleotide probe sequences have been bound previously via complementary ionic interactions to the coating on the sub-micron particle surface. It is speculated that these particle-probe complexes would have a specific affinity for target RNA or DNA sequence via duplex formation with the particle-bound single-stranded probes or by purine-type or R-type triple-strand formation with either double- or single-stranded particle-bound probes. All of these types of nucleic acid target capture have been found to occur routinely in microarray format using glass slides and we speculate will occur as well on the surface of a sub-micron size particle.

Protein Capture. For protein capture, it is anticipated that the majority of ligand surface chemistry routinely used in column chromatography can be readily adapted to this sub-micron particle format. Many specific ligand surface coatings are known; examples are butyl-(C4), octyl-(C8) alkanes, amino phenylborate, nitrile, metal chelating ligands, the EDAC ligands such as thiophilic types of mercaptopyrimidine or with a ligand of mercaptoethanol conjugated to vinyl sulfone, and the ligands used for hydrophobic interactive chromatography. These ligands have been described in patent and published literature for having selective binding towards specific classes of serum proteins such as albumin or immunoglobulins. In one preferred implementation of the present invention, the surface coating for protein capture is the conversion of amino-silane or PEI coating to the corresponding cyano or nitrile derivative or the conversion of the primary amines of these coatings (amino-silane or PEI) to thiophilic ligand (See U.S. Pat. Nos. 4,696,980, 4,897,467 and 5,141,966). The affinity ligands described in these patents all have very specific affinities for immunoglobulin proteins. It is anticipated that these ligands bound to the inventive nano particles will allow the isolation of such proteins from sera and other sources for batch wise purification of immunoglobulin proteins. Other ligands that are envisioned that can be employed using the nano particles batch wise purification of proteins, or nucleic acids, or polysaccharides. Some of these ligands will be proteins such as antibodies or lectins, unique or combinatorial libraries of peptides or oligonucleotides or polysaccharides (synthetic or natural), and affinity batch wise purification of enzymes and/or binding proteins, substrate analogues as ligands, an example would be the use of a heparin ligand bound to sub-micron particle to isolate DNA binding proteins. The above examples are not limiting and demonstrate the flexibility of this invention as a platform for affinity biochemistry One differentiating characteristic of the present invention is that the solid phase substrate for the affinity ligand coatings are particles or fibers in with surface area per gram dry weight of 5 $m^2$ per gram or greater. Another characteristic is that the intrinsic density or these particles be greater than 1. As the surface area increases, the expectation is that the capacity to bind DNA or RNA or protein (as examples) to the solid matrix will increase. For particles, a density greater than water ensures that these particles will settle and separate from the suspension when needed.

A preferred implementation of the present invention would be clays of kaolinite, smectic, and montmorillonite classification, although other clays such as, e.g., magnesium silicate clays such as bentonite, are also contemplated. The density and geometry of these clays facilitate the formation of a stable suspension; however since density is greater than 2, they can be harvested by low speed centrifugation. These clays, with a chemical coating, are a common component of commercial products: such as binders in plastics, glues, and paints. In the present invention, well-known chemistry for making coated clay particles is adapted to create affinity matrices and surfaces for purifying biopolymers, such as nucleic acids or proteins, from crude or refined samples. Thus, the present invention permits retrieval of biomolecules by low speed centrifugation to provide concentrated enriched pellets of the target biomolecule bound with extremely high recovery of the target biomolecule from the pellet being feasible.

As discussed above, the present invention contemplates the use of nanoparticles that have been "activated" by a biopolymer binding reagent. The present invention further contemplates a variety of biopolymer binding reagents for use in activation of nanoparticles to produce activated nanoparticles. In general such binding reagents will be at least bifunctional, i.e., will have at least one functionality directed to biopolymer binding and another functionality directed to activation of a nanoparticle of the present invention. Although these functionalities will often reside in different regions/moieties of the biopolymer binding reagent, the present invention expressly contemplates biopolymer binding reagents where these functionalities are co-resident in the same area of structure or moiety/moieties.

We describe here the use of chemically treated, non-porous sub-micron sized particles (nano-particles) for the capture, concentration, purification and storage of DNA and RNA. The method is based on the use of non-porous, sub-micron size, particulate materials with one preferred implementation being kaolinite clays, kaolin, and fibers with dimension equal to or less than 0.8 ☐m range.

Table 1 below is indicates the particle size range over a series of commercially available nanoparticles that fit within the specification of the invention. Based on density, surface area per volume and sedimentation rate predicted by the other two properties.

TABLE 1

| Material | Density $g/cm^3$ | $<D_1>$nm exp | $m^2/g$ | $m^2/cm^3$ | $V_{(2000g)}$ (cm/min) | $D_{min}$ (nm) | $D_{max}$ (nm) | $(A/V)_{min}$ $m^2/cm^3$ | $(A/V)_{max}$ $m^2/cm^3$ |
|---|---|---|---|---|---|---|---|---|---|
| $X_{ref}$ | 2.0 | 250 | 12 | 24 | 0.46 | 55 | 1,000 | 110 | 6 |
| Kaolin | 2.6 | 200 | 20 | 52 | 0.47 | 50 | 800 | 200 | 13 |
| AlO$_2$ | 2.7 | 43 | 37 | 100 | 0.02 | 40 | 800 | 100 | 12 |
| MgTiO | 3.9 | 50 | 30 | 120 | 0.05 | 35 | 600 | 170 | 10 |
| TiO$_2$ | 4.3 | 50 | 23 | 99 | 0.06 | 30 | 550 | 150 | 9 |
| ZrO$_2$ | 5.9 | 25 | 40 | 240 | 0.02 | 25 | 500 | 240 | 12 |
| WO$_3$ | 7.2 | 40 | 22 | 160 | 0.07 | 20 | 400 | 320 | 16 |
| W | 19.3 | 100 | 7.5 | 150 | 1.34 | 12 | 240 | 1250 | 60 |

In Table 1, the particles tested and described in the teaching section are highlighted. Xref refers to particles with the minimum density (2.0 gr/cm³) specified by the claims. Other materials are commercially available with the physical characteristics listed. Density g/cm³. The density of the particles tested or otherwise available. $<D_1>$nm. Average Particle Diameter of particles tested or otherwise available. m²/g. Surface Area to mass ratio for the material. m²/cm³. Surface area to volume ratio, obtained by multiplying (m²/g)×Density. $V_{(2000\,g)}$ (cm/min). Sedimentation velocity calculated for $<D_1>$nm from the Stokes equation, assuming 2000 g. $D_{min}$ (nm). The smallest average particle diameter which will generate a useful sedimentation velocity, as defined in our teaching as 0.1 cm/min at 10,000 g. $D_{max}$ (nm) The largest particle diameter which will generate a useful sedimentation velocity, defined as in the teaching as 2 cm/min at 500 g. Surface area to volume ratio, calculated for $D_{min}$. $(A/V)_{max}$. Surface area to volume ratio calculated for $D_{max}$.

For particulate applications, the dimensions can be defined as surface area per volume, as calculated from the surface to mass ratio multiplied by the particle density, properties that can be determined empirically for any type of solid, non porous particle. We are speaking of particulate structures whose surface area is equal to or greater than 10 m² per cubic centimeter. For the current invention, we have been working with kaolin clays with surface area dimensions of 20 m² per gram or approximately 52 m2 per cubic centimeter assuming a mean Stokes radius of 200 nm.

For the clay particles, the type of clay tested was kaolin, a kaolinite clay composed of repeating layers of $SiO_2$ with $AlO_3$. These clay particles are chemically modified to first coat the particle with epoxy silane (i.e. [3-Glycidyl-oxypropyl] trimethoxysilane, CAS 2530-83-8) followed by a condensation linkage between the epoxy moiety to a polyamine (polyethylenimine). A preferred implementation is a coating formed between the using kaolin particles, of 200 nm with branched polyethylenimine of of a molecular weight range from 800 daltons to 750,000 daltons all linked through epoxy silane.

Cationic nanoparticles have been made by linking to epoxy-silane coated kaolin with PEI molecules with molecular weights ranging from 800 to750K daltons another method is direct conjugation by silane chemistry directly to the clay surface with an aminosilane (i.e. 3-aminopropyltriethoxysilane, CAS 919-30-2) which results in a surface coated wtih primary alkyl-amines. The key to this invention is that near physiological pH, nucleic acid polymers (DNA and/or RNA) will adsorb electrostatically to the cationic surface coating until released either by raising the pH, and for the PEI surfaces the addition of alkyl sulphonic acids (i.e. sodium dodecyl sulfate). The adsorbed nucleic acid polymer is stabilized against subsequent damage by interaction with components of storage solutions (oxidation), air, subsequent to drying.

The cationic particle adsorbed nucleic acid, when desired, can be concentrated, enriched, and purified away from other cellular contaminants (which do not adsorb as tightly) by pelleted by centrifugation. The result is an enriched nucleic acid fraction that may be stored in the adsorbed state to cationic particle for long periods of time, and either in the hydrated or dry state. The adsorbed the nucleic acid remains, while bound, fully available for hybridization to a cognate nucleic acid strands. In the adsorbed state, the bound nucleic acid can be used directly for hybridization-based analysis or as the source for sequence amplification such as PCR or other thermal cycling or isothermal amplification methods.

The following is a disclosure of the properties and inventions related to the use of sub-micron particles as the solid phase for the manipulation of biomolecules acids based on the partitioning of these biomolecules to the surface of the non-porous nanoparticles in colloidal suspension. The common chemistries of partitioning a biomolecule from the solution phase to a solid phase adsorption, due to ionic affinity of the nanoparticle surface for the biomolecule, or the partitioning could be due to changes in solution conditions that induces the biomolecule to aggregate or adsorb to the solid phase surface; changes such as temperature, organic solvents, salts, pH, etc. For one trained in the art, these process of chromatography are generally applicable to the isolation of most biomolecules, such as nucleic acids, proteins, as well as for complex biological complexes such as cells, organelles, and viruses. In our examples we will show that those same generalizations of solid phase chemistry for biomolecule manipulation are directly applicable for nucleic acid, protein and as prophetic examples for microbial cells and viruses. Other applications dependant on surface adsorption are biomolecule dry state or wet state stabilization and storage Below will be a description of a family of related inventions based on colloidal state, solid phase chromatography based on nanoparticles.

Use of Cationic Nanoparticles for Purification of Nucleic Acid from Complex Mixtures Cationic coated nanoparticles such as PEI-epoxy-silane coated 200 nm kaolin particles adsorb DNA and RNA at acidic to neutral pH, 5.5 to 8.5, though when pH is shifted above 10.5 the DNA is released in an intact state though the RNA will be degraded. It has been found that SDS, sodium dodecyl sulfate, at concentrations as low as 0.1% cause the release of DNA or RNA from these PEI coated particles. From crude cellular samples such as buccal cell sample collected by mouth wash rinse, are lysed by and DNA was released by adding to the cells suspended in mouthwash a stock solution containing combination a non ionic detergent (i.e. Tween 20, Triton X-100) and chaotropic agent (formamide or guanidinium HCl), a chelating agent (EDTA) and a buffering agents such as MOPS. In this solution, PEI coated kaolin particles (200 nm size) will adsorb DNA and RNA. After a short incubation period, less than 30 min) the particles sedimented under low speed centrifugation at 500 G for 10 minutes.

The resulting cationic particle pellet contained the tissue nucleic acid in a highly enriched and concentrated form. This pellet was dispersed in simple buffers such as Tris-EDTA and washed to remove non adsorbed substances, and the particles are re-pelleted by centrifugation and not lose the majority of the adsorbed nucleic acid. Nucleic acid was released from the PEI-epoxy kaolin in the presence of SDS (0.1% or greater), in a CAPS/Tris buffers above pH 9.5 to 11, with the Na CAPS solutions as low as 25 mM with or without LiCl at 200 mM.

The utility of the inventive PEI coated nanoparticles includes, without limitation, that nucleic acids are adsorbed at pH conditions between about 5 to 9 in the presence of high concentration chaotropic agents Ike formamide at 40% v/v and can be further washed with such reagents at high salt, high concentration of formamide or guanidium and still retin the bound nucleic acid. As noted above, DNA bound to PEI epoxy kaolin remains adsorbed also in dilute buffers (e.g., Tris EDTA), water or in polar organic solvents (e.g., formamide). This permits removal of other contaminants which are not as tightly bound to the PEI. By shifting the pH about 9.5, the DNA will elute from the PEI coated kaolin. The nucleic acid released into solution is completely compatible with other genetic analysis, such as PCR. Once the DNA is released and harvested from the cationic particles, the pH of the buffer may be reversed to neutral by addition of weak acid.

Cationic Particles for Storage and Retrieval of Nucleic Acid

Another embodiment of the invention is based on stabilization of biopolymers, such as DNA or RNA, that occurs when they adsorb to cationic particles. It is known in the literature that when adsorbed to the surface of a non-porous substrate, single or double stranded nucleic acid become stabilized against degradation by endogenous or applied nucleases. It is also anticipated from the literature that when small particles are formed into a densely-packed solid phase, such as by centrifugation to form a pellet, the surface of any small particle embedded within the pellet, or anything adsorbed to the surface of that small particle will become much less available to damage that would result from surface interaction with the components of air or any solution that the pellet was suspended within. Cationic particles are sub-micron particles added to a solution of nucleic acid, either DNA or RNA, at near neutral pH which is followed by adsorption of the nucleic acid to the PEI surface coating. In a preferred implementation, the PEI surface coating is constructed to be in the 5 nm-10 nm thickness range, so that adsorbed nucleic acid strands (which are themselves about 1 nm thick) will be embedded inside the cationic PEI surface. Thus embedded, they are restricted from interaction with solution phase reactants, such as oxygen radicals or enzyme contaminants. Having been captured in that way, the resulting cationic particles-nucleic acid complex can be stored at room temperature or at 4° C. or frozen, indefinitely. At any later date, the complex can be sub-divided as needed by pipetting or other fluidic manipulations, followed by release of the stored nucleic acid into fluid solution by raising the pH to a value greater than 8: conditions where the PEI coating neutralizes and the DNA or RNA is released from electrostatic attraction to the sub-micron particle.

Cationic-Kaolin Complexes as Substrate for Nucleic Acid Hybridization

One aspect of the present invention is also based upon the fact that once adsorbed to alkyl amine coated kaolin, coated with either PEI or amino-silane, the nucleic acid can hybridize specifically to its cognate complementary polynucleotide sequence while still adsorbed to the nanoparticle coating. There are several enabling aspects of this new approach to nucleic acid hybridization including a) Enrichment of Dilute Targets; b) Target Structure Normalization; c) Induction, in Solution, of the Unwound Duplex and Triplex Form; and d) Enriched, Solid State PCR.

A. Enrichment of Dilute Targets

Since the surface area to volume ratio of a coated 200 nm Kaolin particle is about 40,000 mm$^2$/μL, and the surface binding capacity for nucleic acid is about 30-60 μg/μL as hybridization solid phase a lot of capacity can be obtained in very small volumes. These coated kaolin sub-micron particles are well behaved as a suspension at ambient gravity and will remain in the colloidal state for many hours. Such suspensions can be presented as a stable buffer solution at up to 10% by mass of the sub-micron particle, thus about 60 μg of nucleic acid will bind spontaneously to 1 μL of such sub-micron particles suspension, can be pelleted and be resuspended in as little as 10 μL of a useful neutral-pH binding buffer for hybridization analysis.

Thus, the 200 nm cationic-Kaolin sub-micron particle (either PEI or amino-silane coated) can be used to "pull", by adsorption, several micrograms of nucleic acid from a dilute solution as large as 10 mL, then after centrifugation, present that nucleic acid for hybridization as a stable 10 μL suspension with an apparent nucleic acid concentration that has increased by 10,000 fold. Since nucleic acid hybridization rates are linearly dependent on concentration, this aspect of the technology could increase the rate of modified solution phase hybridization up to 10,000 fold.

B. Target Structure Normalization

Many of the most advanced methods of applied genetics are based on hybridization of known nucleic acid probes to an unknown nucleic acid target. These technologies however experience significant skewing of the resulting data due to undesired folding of the nucleic acid target of interest, due to intramolecular associations to form generalized "stem-loop" nucleic acid folds. In the present invention, we describe the use of alkyl amine coated particles (PEI or amino-silane-Kaolin) as a method to eliminate such intramolecular folding in a modified solution phase hybridization reaction.

The invention is based on the observation that, on either PEI or alkyl amine coated particles, long target nucleic acids can be made to adsorb stably to the coated sub-micron particle under denaturing solution-state conditions which have eliminated intramolecular or intermolecular folding. Once adsorbed in an unfolded state, re-folding is prohibited once the kaolin-nucleic acid complex is returned to a non-denaturing solution to perform an ordinary hybridization reaction. Such slow reversibility is due to the fact that, although the surface bound target nucleic acid can bind to a cognate solution-phase nucleic acid strand, the numerous surface contacts with the alkyl amine coated surface on the Kaolin sub-micron particle "immortalize the unformed target state, thereby prohibiting its rearrangement into an intramolecular fold while bound to the surface, a secondary structure that would inhibit intermolecular duplex formation.

C. Induction, in Solution, of the Unwound Duplex and Triplex Form

It is known from the literature that, on a planar glass slide coated with a short chain amino-silane, adsorbed nucleic acid molecules appear to be organized as a monolayer, which cannot form an ordinary helical duplex. Instead, upon binding a cognate solution state strand, the resulting duplex product appears to be an unwound, or very shallowly wound duplex. Under those circumstances where this unwound duplex state is desirable, the present invention allows such unwound duplexes to be formed in an ordinary solution state hybridization reaction, because on the sub-micron particle surface, over domains longer than the duplex itself, the kaolin sub-micron particle presents a smooth, perfectly planar surface structure identical over 100 bp or more to that presented by a planar glass slide.

A useful secondary attribute of the unwound duplex state has been discussed in the literature, also on amino-silane coated glass slides. There, it has been shown by others that, in the adsorbed state, a surface bound single strand develops the capacity to bind a cognate solution-state duplex to form a sequence specific triple helix pairing. Similarly, the literature has suggested that the same coated glass slides can adsorb a duplex, which then develops the ability to bind a solution state single strand, to form what is presumably the same sort of triple stranded complex.

There are numerous potential benefits to be had in forming this alternative, triple helix method for nucleic acid hybridization. The present invention allows, for the first time, this alternative method of nucleic acid hybridization to be used in the solution state, to replace the current use of duplex formation as the basis for genetic analysis.

Enhanced Biochemical Amplification via Cationic-Kaolin Complexes

As discussed above, the nanoparticles of the present invention in suspension may be used in a variety of manipulations of biopolymers, e.g., immobilization, purification, concentration, archival storage, etc. A non-limiting series of examples of these various applications is given below.

The inventive technology may be scaled up to support routine automated 1000-sample-per-day throughput at one automated workstation by a single technician to produce PCR ready DNA.

A Nanoparticle Approach to the Capture and Purification of Dilute DNA

Based on the current unmet needs in the area of forensics and genetic epidemiology, a new technology has been conceived that allows the DNA complement of a large volume dilute solution to be captured, enriched and then concentrated into a microliter-scale pellet, where it can be released at a later date and used directly for genetic analysis. The technology is based on exploitation of the properties of dense nanometer scale particles as the substrate for nucleic acid specific affinity capture. Below, we describe in general terms, the concepts which drive the design process.

The Sedimentation Properties of Dense, Submicron Particles.

We have found that a general solution to the dilute DNA capture and purification problem is as follows. What is needed is a type of particulate material that offers a large surface area to bind biomolecules such as nucleic acid, via surface mediated affinity capture. Additionally, the material should have an extremely large surface area per unit mass to allow for high capture efficiency, but ideally, should not be porous, since porous particulate materials tend to be structurally unstable and binding and elution of the biomolecule from a porous matrix is not as rapid, kinetically, then from the outer surface of a particle.

But most importantly, a primary aspect of the present invention is that the particulate material should, at rest, remain as a stable suspension in a water solution for as long as is needed for the manipulation. However, in accordance with a particularly preferred embodiment, when necessary, these same particles in stable suspension could be harvested by low speed centrifugation within minutes (centrifugal fields at or less than 10,000 G) so that the particles suspended in a large volume could be transferred via centrifugal translation, to form a compact pellet.

Based upon the foregoing general criteria, we have conceived of a general solution to the above-described problem, based on the use of dense, nanometer scale particles. This general solution has been reduced to practice via a specific solution to the problem: the development of a series of coated nanoparticles composed of aluminosilicate or of metal oxides from 20 nm to 200 nm size.

Surface Modifications of Chromatographic Materials by Adaptation of Passivation Chemistry of Metals and Metal Oxides Other aspects of the present invention are methods for altering and improving the properties of the activated nanoparticles of the invention via adaptation of metal/metal oxide passivation chemistry. Passivation chemistry entails the use of usually oxyanions for modifying metallic surfaces for corrosion resistance referred to as passivation of metal and metal oxide surfaces. For many embodiment of this invention, the nanoparticle matrices consist of materials or contain exposed metal or metal oxide surfaces. For the present invention, the chemistry of passivation, the treating of the nanoparticles with oxyanions, enhances the chromatographic properties of these nanoparticle surfaces, such as improve the reversible binding (under neutral and mild conditions) of biomolecules absorbed to the matrix surface. For this invention, Passivation is directed, in particular, to chromatography matrices consisting of nanoparticles and nano-dimensional fibers however, it is obvious to one trained in the art, that the use of passivation chemistry to other chromatographic materials composed or consist of metals or metal oxides will improve, or specifically alter their chromatographic surface properties. The composition of these matrices may include: clays, for examples aluminum silicates, magnesium silicates or ferric silicates; metals or alloys that contain aluminum, iron, magnesium, zirconium, hafnium; tungsten, and, other metal elements and their respective oxide surfaces, either as natural or of synthetic origin. This includes other solid phase matrices that are coated with thin films comprising of metal or metal oxides.

The adapted passivation methods used for this invention include the binding of oxyanions to metal or metal oxide surfaces. Examples of oxyanions are silicates, borate, phosphate, sulfate, carbonate, arsenate, vanadates, permanganate, molybdate, tungstenate, and chromates. Other ions and compounds that passivate surfaces and are expected to be useful for this invention include, e.g., fluoride ions and chelating compounds based on carboxylic acid moieties, such as EDTA, EGTA, citrate, oxalate, acetate, and formate. Amine or thiol based chelating agents may also behave as surface passivation agents for this invention. Examples of amine compounds include diamines, formamide, lysine, and imadizoles, including histidine. Examples of thiols include mercaptans or alkyl thiols such as cysteine. Also useful as passivation agents are phosphate and sulfate derivatives as seen with alkyl sulphones such as sodium dodecyl sulfate or with polysaccharides such as heparin or dextran sulfate. Examples of alkyl phosphones include phosphate detergents as well as phospholipids, phosphorylated polysaccharide, and phosphorylated proteins. These lists are not intended as limiting; oxyanion or oxyanion-like molecules generally are expected to exhibit passivation activity, e.g., to act as blocking agents to hinder the association of nucleic acids from directly binding to metal or metal oxide surface.

The following non limiting examples exemplify the alternative embodiments of the present invention.

EXAMPLE 1

Process to Make Washed Kaolin Nanoparticles

Washed kaolin nanoparticles were prepared for use in adsorption chromatography by first suspending the kaolin (CAS# 1332-58-7) nanoparticles, (Englehard, ASP ULTRAFINE), in N,N,dimethyl formamide (DMF, CAS#68-12-2) at a ratio of 0.5 to 1 g particles (dry weight) to 9 mL DMF. This colloidal suspension was incubated for a minimum of 16 hrs. The nanoparticles were washed by a sedimentation-resuspension process by (1) sedimenting the nanoparticles out of suspension by centrifugation at 4000 G for 15 min; resuspending the particles by adding 1 mL of liquid phase (for this process it was water) per 5 grams (dry weight) of particle-sediment and mixing to form a thick slurry; followed by adding 9 mL of liquid phase (water) per gram (dry weight) to the slurry and mixed to form a confluent nanoparticle suspension. For the washed kaolin particles, per 10 mL of this nanoparticle suspension was added and mixed 1 mL of 5 M sodium chloride solution followed by a 12 to 16 hours incubation at room temperature. These particles were then again washed by the sedimentation-resuspension process, using water as the liquid phase, which was repeated three more times. The final concentration of particles in suspension was adjusted to 50 mg (dry weight) per milliliter in water. This was the suspension used for all of the adsorption experiments described in later experiments.

EXAMPLE 2

Process to Produce Epoxy Silane Coated Kaolin Nanoparticles in DMF Suspensions

For both the epoxy silane coated kaolin nanoparticles were produced by the following methods in kaolin nanoparticles (Englehardt, ASP Ultrafine) suspended in DMF at a concentration of 100 mg per milliliter and incubated for minimum of 16 hrs at room temperature. The nanoparticles were sedimented from suspension by centrifugation at 4000 G for 30 min, resuspended in DMF at ratio of 1 g to 8 ml DMF. For PEI coated particles, to the 8 mL of the DMF suspension was added 2 mL of a 10% solution 3-glycidoxytrimethoxysilane (epoxy-silane) in DMF and mixed then incubated for minimum of 16 hrs. These epoxy-silane particles were washed by sedimentation-resuspension process (see Experiment 1), using DMF as the liquid phase, and this process was repeated twice, though the final concentration of epoxy-silane coated particles was 125 mg/mL (dry weight of kaolin particles).

EXAMPLE 3

Process to Produce PEI-Epoxy Silane Coated Kaolin Nanoparticles in DMF Suspensions 2 mL of a 10% water solution of polyethylenimine of either a branched polymer of 750,000 MW (CAS#25987-06-8) or 25,000 MW (CAS#9002-98-6) was added to 8 mL of epoxy coated kaolin nanoparticles (Experiment 2) and mixed and incubated for a minimum of 16 hrs. The PEI-epoxy coated particles were then washed three times by the sedimentation-resuspension using water as the liquid phase. The final particle concentration for these suspensions of these polyethylenimine-epoxy silane coated kaolin particles was 50 mg (dry weight of kaolin nanoparticles) of particles per mL.

EXAMPLE 4

Process to Produce Amino Silane Coated Kaolin Nanoparticles in DMF Suspensions

The DMF washed kaolin nanoparticles suspension (from Example 1) was suspended in DMF solution at a ratio of 1 g (dry weight) per 8 ml DMF. To 8mL of the above suspension, 2 mL of a 10% solution 3-aminopropyltriethoxysilane (amino-silane) dissolved in DMF was added, mixed and incubated for minimum of 16 hrs. These amino-silane particles were washed by the sedimentation-resuspension process (see Example 1), the first wash using DMF as the liquid phase, followed by two additional washes with water. The final particle concentration for the amino-silane coated kaolin nanoparticles was 125 mg (dry weight of kaolin nanoparticles) of particle per nL of water suspension.

EXAMPLE 5

Buccal Cell DNA Isolation Collected and Suspended in Mouthwash

Experiment for isolating DNA from Buccal samples collected by mouthwash aspirates: The buccal sample was collected by rinsing 20 mL of mouthwash (SCOPE, Proctor and Gamble, Cincinnati, Ohio), in the mouth for 1 min. For these samples, the total volume yield of mouthwash aspirate was 40 mL that was divided into 1 mL aliquots. The DNA extraction from these 1 mL of buccal-mouthwash aspirate was to add 0.1 mL of a buffer solution composed of 500 mM MES (CAS#4432-31-9), 250 mM EDTA (CAS#60-00-4) disodium salt, 0.1 mL of 10% solution of NP-40 (CAS#9030-19-5) and 0.8 ml of formamide (CAS#75-12-7). These solutions were mixed followed by 15 min. incubation at 55° C. The extraction mix was centrifuged at 10,000 rpm (~8,000 G) for 10 min and the supernatant was retained and transferred to a new 2 ml micro-centrifuge tube. To this DNA sample was added 50 μL of a 50 mg/mL suspension of PEI-epoxysilane coated kaolin (See Experiment 2, PEI-epoxy-silane kaolin nanoparticles), that was mixed to a confluent suspension, that was then incubated for 15 min at room temperature. After this incubation, to the DNA sample- PEI kaolin nanoparticle suspension was added 50 μL of suspension at 50 mg/mL of DMF washed kaolin particle (See experiment 1). These particles were mixed to confluent suspension. The suspensions of these two types of nanoparticles were co-sedimented by centrifugation at 4,000 G for 2 minutes at room temperature. The supernatant was discarded and the pelleted nanoparticles and tube were rinsed with 500 µL of a 1/10th dilution of the MES/EDTA solution (50 mM MES; 25 mM EDTA, see above). The pelleted nanoparticles and suspension were subjected to centrifugation at 4,000 G for 2 minutes and the rinse supernatant was discarded. To the particle sediment was added 200 µL of DNA release buffer consisting of 200 mM CAPS, sodium salt (CAS #1135-40-6) with 0.2% of SDS (CAS#151-21-3). The particle pellet was disaggregated and mixed to confluent suspension and incubated at 55° C. for a minimum of 30 minutes. Once the particles were in complete suspension, the PEI coated particles were removed from DNA eluate by sedimentation at 10,000 G for 5 min and the supernatant was transferred to a new microfuge tube. The DNA was further purified from the 200 µL of DNA eluate by adsorption onto washed kaolin particles (See experiment 1) by adding 20 µL of a 50 mg/mL suspension of washed kaolin, that was mixed to a confluent suspension, then adding two volumes (440 µL) of 2-propanol, which was mixed and incubated for minimum of 30 min at room temperature. These nanoparticles with absorbed DNA were sedimented from suspension by centrifugation at 8,000 G for 5 min and the 2-propanol containing supernatant was discarded. The nanoparticle pellet and tube were rinsed with 500 µL of 40% 2-propanol/water solution, and incubated for minimum of 10 minutes at room temperature, then re-sedimented by centrifugation at 4000 G for 1 minute and the supernatant was discarded. The nanoparticle sediment was air dried for 15 min or until smell of alcohol was not noticeable. The DNA was eluted from these nanoparticle sediments by adding 200 µL of a 1/10th dilution of Tris-EDTA buffer (1 mM Tris, 0.1 mM EDTA, pH 7.5). The nanoparticle sediment was completely resuspended to a confluent suspension by periodic mixing (pipeting) and incubation at 55 ° C. for minimum of 30 minutes. The particles were removed from the DNA eluate by centrifugation at 10,000 rpm for 5 minutes and resulting DNA solution was transferred to a new tube. This DNA solution was the source for further analysis by PCR.

EXAMPLE 6

PCR Analysis of Human DNA Isolated by the Invention

PCR was the process to compare and evaluate the DNA capture process either with PEI kaolin and/or by adsorption to washed kaolin nanoparticles and the adsorption of human DNA on kaolin particles. These PCR analyses were based on a nuclear chromosome encoded gene, amelogenin, encoded on both the X and Y chromosome. The primers used were of these two sequence, for SEQ ID NO. 1 the sequence was 5'-AGA TGA AGA ATG TGT GTG ATG GAT GTA -3', and for SEQ ID NO. 2 the sequence was 5'- GGG CTC GTA ACC ATA GGA AGG GTA - 3' each derived from the amelogenin sequence in GenBank with accession number AY040206. The PCR product from these two primers yield a 558 base pair long fragment. The volume of these PCR tests were 50 µL volume and were composed of 1× Roche PCR Buffer, 1.5 mM MgCl$_2$, 0.4 µM primers, 0.2 mM dNTP's, 0.16 mg/ml BSA, and 0.4 µL of Fast Start Taq at 5 U/µL. The conditions for these PCR tests were for the first step to be at 94° C. for 4 minutes, followed by 35 cycles composed of with these three steps, 94° C. for 1 min followed by 65° C. for 1 min then followed by 72° C. for 1 min. After these 35 cycles, the reactions were incubated at 72 degrees ° C. for 7 min followed by a holding step at 15° C. until the reactions were stopped. All of PCR results were evaluated by electrophoresis of 1/5th of the reaction volume in agarose gels using Tris-Borate-EDTA buffer system. The molecular size controls were the DNA ladder of the 1 Kb ladder from Invitrogen (1 Kb marker cat # 15615-016). The PCR controls were a negative control, a reaction with no added DNA template, and the four positive controls with a fixed and known amount of human DNA (Roche Human Genomic DNA catalog # 1691112) as PCR templates, at these concentrations, 10 ng, 1 ng, 0.1 ng and 0.01 ng per 50 µL PCR reaction.

EXAMPLE 7

Further Examples of PEI Kaolin Nanoparticles with or without Kaolin Particles

FIG. 1 illustrates how mixtures of nanoparticle behave when mixed. In this example PEI coated kaolin nanoparticles were mixed with different amount of washed kaolin. As indicated in the FIG. 1, there is an optimal ratio of kaolin (Example 1) to PEI coated kaolin (Example 3) to be effective in DNA elution. The most optimal ratio being a 1:1 ratio (by weight of washed kaolin to PEI-kaolin.

FIG. 2 illustrates how four different formulations affected the release of DNA from PEI coated particles and the efficiency of DNA release from PEI kaolin nanoparticles to determine whether or not these particles mix with kaolin nanoparticles during the DNA release treatment. The formulations were various combinations, all buffered with 0.2 M concentration of the sodium salt of CAPS, with or without Tris buffer at 50 mM, and with or without SDS at 0.2% wt/vol. The mixtures of two nanoparticles, 5 mg of PEI kaolin to 5 mg of kaolin, were displayed in lanes 2, 4, 6, 8) versus; the release from 5 mg of PEI kaolin nanoparticles, only, were displayed in lanes 1, 3, 5, and 7. The two controls (See Example 6) were an electrophoretic control, the 1 Kb molecular wt marker and the second was PCR reaction control, a reaction that had 10 ng of pure human DNA as the template. Regardless of the release buffer, the PCR products generated from the PEI kaolin +kaolin mixtures were more efficient in releasing DNA. The results of the different release buffers were (lanes 1 and 2) 200 mM CAPS, (lanes 2 and 4), 200 mM CAPS, 0.2% SDS the buffer described in experiment 3, (lanes 5 and 6) 200 mM CAPS, 50 mM Tris (from 1M, pH 8.0 Tris solution), (lanes 7 and 8) 200 mM CAPS, 50 mM Tris-pH 8.0, 0.2% SDS. For all cases each of these buffers worked, though the 200 mM CAPS, 0.2% SDS, and 200 mM CAPS, 50 mM Tris-pH 8.0 worked best. For all the PCR reactions the final elution volume was 200 µL, and 2 µL was used as template for these 50 µL PCR reaction (See Experiment 4) and analysis of 1/5th of the reaction volume by ethidium bromide stained agarose gels. The PCR reaction was of that described in Example 6.

FIG. 3 illustrates a gel of PCR products from DNA purified from whole blood using a two tier purification process based on sequential use of PEI kaolin nanoparticles followed by kaolin nanoparticles. These PCR products of 558 base pairs are from the amelogin gene (X/Y). For each lane, 10 µL of the 50 µL PCR reaction was analysed in the gel. Lanes 1 and 2 were the amplicons from DNA isolated by the two tiered process from whole human blood. The PCR reaction seen in lane 1, was initiated with 1 µL of 50 µL final DNA eluate, for the PCR reaction seen in lane 2, the reaction was initiated with 0.1 µL of the 50 µL eluate, same eluate used for PCR reaction seen in lane 1. Lanes 3, 4 and 5 were controls, the PCR products from reactions using known quantity of human genomic DNA (Roche Human Genomic DNA catalog # 1691112) as template for the reaction. The human DNA content added to these respective, 50 μL PCR reaction were 10 ng (lane 3), 1 ng (lane 4), and 0.1 ng (lane 5).

EXAMPLE 8

Conditions that Support the Adsorption of Human DNA to Washed Kaolin Nanoparticles in 66% Solution of 2-Propanol FIG. 4 is a gel displaying PCR results from adsorption concentration process using purified human DNA (For PCR conditions and control source of human DNA see Experiment 4). Three amounts of human DNA in 0.5 mL volume were tested, these were 0.05 μg (lanes 1-4), 2 μg (lanes 5-8) and 5 μg (lanes 11-14). The solutions that were used to dissolve the DNA were 200 mM CAPS, 0.2% SDS, (lanes 1, 5, and 11), 200 mM CAPS, 1% SDS C (lanes 2, 6, and 12), 2× TE +1% SDS, pH 11.5 (lanes 3, 7, and 13), and 200 mM NaCl, 1% SDS (lanes 4, 8, and 14). The process was as described in Experiment 3. To each of the 0.5 mL human DNA solutions, 2 mg of kaolin nanoparticles were added and mixed to a confluent suspension. Then 2 volumes (1 mL) of 2-propanol was added to each of the suspensions and incubated them at room temperature for 30 min. The DNA/particle complex were sedimented from each suspension by centrifugation (8000 G for 5 min), then washed in 0.5 mL of 40% 2 propanol/water solution, followed by centrifugation, then air dried for 5 to 10 min. The DNA was eluted from the nanoparticles by resuspending the sedimented particles to a confluent suspension in 1/10 dilution of TE and incubating these suspensions for 30 min at 55° C. These particles in the suspensions were sedimented to a tight pellet by centrifugation, and the DNA was in the eluate solution, and recovered by transferring to a new tube. The elution volume for all each of these extracts was 20 μL. For the PCR analysis (50 μL volume), the following volumes of the eluates were used as the DNA source; 4 μL of the eluate from each of the 0.05 μg samples, 0.1 μL equivalent volume (as 1 μL from a 1:10 dilution) of the eluate from each of the 2 μg samples, and 0.5 μL equivalent volume (as 1 μL of a 1:20 dilution) of the eluate from each of the 5 μg samples. As illustrated by the intensity of each band compared to each other and to the DNA standards, the yields of DNA were deduced. The DNA standards were PCRs that were initiated with these quantities of control human DNA (as in Experiment 4), these were 10 ng in lanes 9 and 15, 1 ng in lane 16, 0.1 ng in lane 17, and 0.01 ng in lane 18. By comparison of band intensity the yield from each of the adsorption samples was estimated. The overall result was that each of these solutions did cause the adsorption of DNA onto the particles in the presence of 2-propanol at 66%. At the highest concentration (5 ug in 500 μL) all solutions worked well. However, for the lower concentrations, the PCR reactions indicate a difference in efficiency for DNA binding, however this may be an artifact due to SDS carry over into the PCR. At the highest concentration all reactions were approximately in the same range.

EXAMPLE 9

Use of Kaolin Nanoparticle to Concentrate Whole Blood DNA Eluted from Cellulose Paper (Whatmann FTA Paper)

Figure 5:
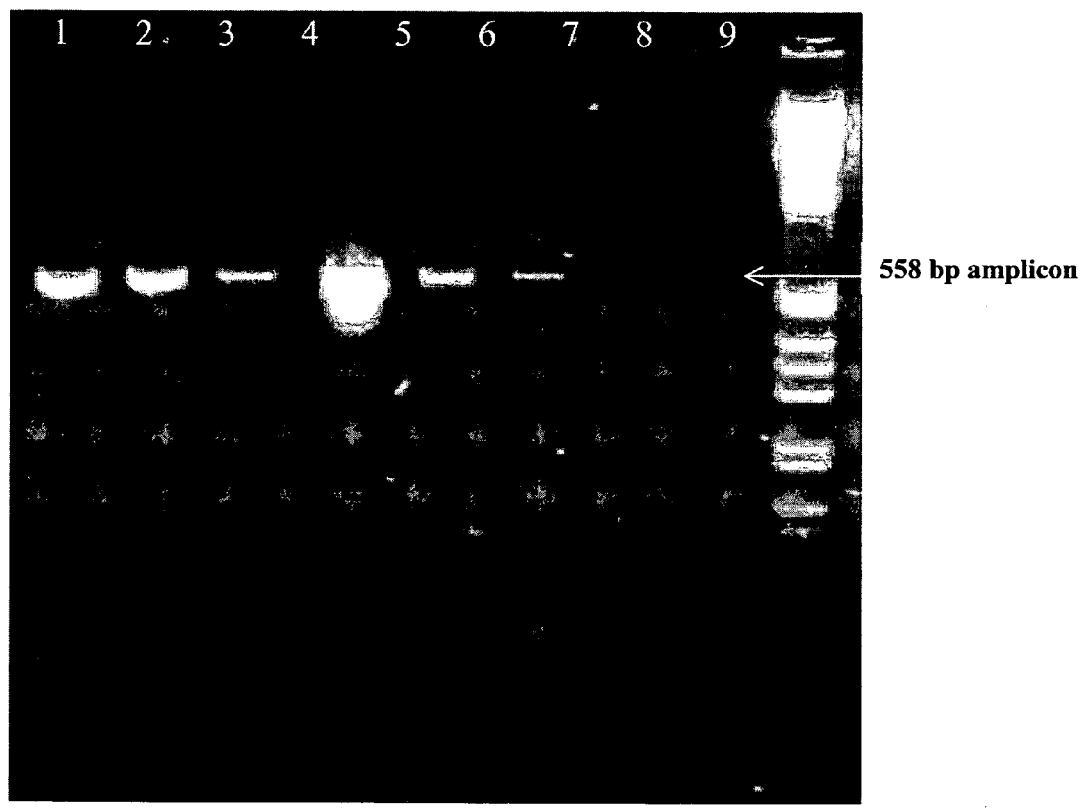
FIG. 5:
The PCR products from DNA purified from whole blood using a two tier purification process based on sequential use of FTA paper storage followed by absorption to washed kaolin nanoparticles. (See Example 9).

Illustrated in FIG. 5 are the PCR products from DNA purified from whole blood using a two tier purification process based on sequential use of FTA paper storage followed by adsorption to washed kaolin nanoparticles. The whole blood spotted (13 μL) was applied to a 6 mm diameter FTA paper disk and air dried. The dried sample was stored at room temperature for 24 days. For this process each sample consisted of paper eluent from 1 (lane 1), or 2 (lane 2), and 3 (lane 3) paper disks per sample. The desorption process of the whole blood DNA was to soak the disks with some agitation with 10 mM Tris, pH 8.0, 0.1 mM EDTA, and 1% Triton X −100 solution, soak for 30 min, change solution and agitate and soake an additional 30 minutes. This solution was removed and the disks were soaked in 10 mM Tris, 0.1 mM EDTA for 30 min, with occasional agitation, this solution was removed and this step was repeated again for an additional 30 min. This last solution was removed and these disks were soaked in 0.5 mL of elution buffer (10 mM Tris pH 11.5) incubated for 45 min. After this incubation, the eluant solution was transferred to a fresh tube, and 10 μL of 50 mg/mL solution of washed kaolin in water was added, mixed to confluent suspension, then 1 mL of 2-propanol, this was incubated at room temperature for 1 hr. These particles were sedimented from this suspension, and washed with 70% Ethanol, centrifuged, and allowed to air dry for 10 min. To elute the DNA from the kaolin nanoparticles, 20 μL of a 1/10 dilution of TE buffer was added to the pellets and resuspened and incubated for 1 hour at 55° C. The kaolin nanoparticles were resedimented from suspension and the DNA eluate was transfered to a new tube.

With reference to FIG. 5, the PCR products obtained from Example 6 in lane 1 were from the reaction initiated with 2 μL of the single disk extract, for lane 2 were from the reaction initiated with 1 μL of the extract from two disks, and for lane 3 were from the reaction initiated with 0.5 μL volume equivalent (5 μL of 1/10 dilution of the kaolin eluate) for the three disk extract. Lanes 4 through 8 were PCR products initiated with 10 ng, 1 ng, 0.1 ng and 0.01 ng, and the negative (no DNA) control, respectively. Lane 9 was the 1 kb ladder (Roche Human Genomic DNA catalog # 1691112). The results of this experiment indicate that an expected yield of DNA was obtained for each, though the observation was that some detergent remained with the kaolin nanoparticles throughout the isolation, thus the three disk extract contained more detergent than the two versus one. The results for single disk extraction was within the realm expected for DNA yields from 13 μL whole blood as estimated by PCR.

EXAMPLE 10

Process to Produce Washed Kaolin Nanoparticles of Tighter Specifications

The washed kaolin nanoparticles were prepared for use in absorption chromatography by first suspending the kaolin nanoparticles, Englehardt, ASP G90 (size specification of 200 nm±20 nm, in N,N,dimethyl formamide (DMF) at a ratio of 0.5 to 1 gram of particles (dry weight) to 9 mL of DMF. This colloidal suspension was incubated for a minimum of 16 hrs. The nanoparticles were washed by a sedimentation-resuspension process by (1) sedimenting the nanoparticles out of suspension by centrifugation at 4000 G for 15 min; resuspending the particles by adding 1 mL of liquid phase (for this process it was water) per 5 grams (dry weight) of particle-sediment and mixing to form a thick slurry; followed by adding 9 mL of liquid phase (water) per gram (dry weight) to the slurry and mixed to form a confluent nanoparticle suspension. For the washed kaolin particles, per 10 mL of this nanoparticle suspension was added and mixed 1 mL of 5 M sodium chloride solution followed by a 12 to 16 hours incubation at room temperature. These particles were then again washed by the sedimentation-resuspension process, using water as the liquid phase, which was repeated three more times. The final concentration of particles in suspension was adjusted to 50 mg (dry weight) per milliliter in water. This was the suspension used for all of the absorption experiments describe in. later experiments

EXAMPLE 11

Process to Produce Phosphate Treated Kaolin Nanoparticles

The acid washed kaolin nanoparticles were prepared first suspending the kaolin (CAS# 1332-58-7) nanoparticles, Englehardt, ASP G90 in de-ionized water at a wt to volume of 1 to 3. This colloidal suspension was incubated for a minimum of 16 hrs. The nanoparticles were washed by a sedimentation-resuspension process by (1) sedimenting the nanoparticles out of suspension by centrifugation at 4000 G for 10 min resuspending the kaolin in water at same ration and repeating this process until the supernatant were clear with no sign of opalescence. This final kaolin pellet was resuspended 1 to 3 with water and an equal volume of 10% sulfuric acid is added to the suspension. This sulfuric acid/kaolin slurry was mixed and incubated at room temperature from 1 to 2 hours, then washed with distilled water by the sedimentation-resuspension process until the pH of the supernatant was the same as the distilled water. To this suspension, at a 1 to 10 ratio was added $1/50^{th}$ volume of 500 mM NaF, and incubated mixed and the subjected to one round of sedimentation-resuspension with distilled water, with the pellet being resuspended in 100 mM NaH2PO4 at a ratio of 1 to 10 and kept mixing for at least 16 hours. This suspension was subjected to three rounds of the sedimentation-resuspension with 1 mM NaH2PO4. The particles were stored in this condition until ready for dilution in 1 mM NaH2PO4 and 10 mM NaF.

EXAMPLE 12

Process to Produce Epoxy-Silane Coated Kaolin Nanoparticles

Epoxy coated nanoparticles were produced by first treating the nanoparticles, processed by Example 11 by resuspending these particles in 50 mM HCl at a particle to solution ratio of 1 to 5 and mixing this suspension for 1 hour at room temperature, this followed by several of sedimentation-resuspension in water, until the supernatant is the same pH of the distilled water. The pellet is then resuspended in a DMF at a particle to DMF ratio of 1 to 1 followed by 9 volumes of Isopropanol and mixed. To this suspension is added 0.2 volumes of 3-glycidoxytrimethoxysilane (epoxy-silane) and this suspension was under constant mixing for a minimum of 16 hrs. These epoxy-silane particles were sedimented at 4000G for 10 min, resuspended in 0.1 M solution of NaCl/50% Isopropanol, and washed twice more by sedimentation-resuspension with 100 mM NaCl, if the particles were to be used within hours. If the particles were to be stored, the particles were sedimented and resuspended in Isopropanol and stored at −20° C.

EXAMPLE 13

Process to Produce PEI-Epoxy-Silane Coated Nanoparticles

The nanoparticles coated with epoxy-silane (Example 12) were suspended in 100 mM NaCl at a wt to volume ratio of particle to solution in the range of 1 to 8. To each 8 mL of epoxy coated kaolin nanoparticles (Example 2) suspension was to add and mix 2 mL of a 10% water solution of branched polymer of polyethylenimine, of 750,000 MW (CAS#25987-06-8), 25,000 MW (CAS#9002-98-6), or 800 MW, and this mixture was incubated with constant mixing at room temperature for a minimum of 16 hrs. The PEI-epoxy coated particles were then washed three times by the sedimentation-resuspension using water as the liquid phase. Storage conditions for these particle suspensions was at a concentration of 10 to 50 mg per milliliter in water.

EXAMPLE 14

Process to Make Cibacron Blue-PEI-Epoxy-Silane Coated Nanoparticles

The process for producing Cibacron blue coated particles was to resuspend the PEI-epoxy-silane coated particles from Experiment 13 in 100 mM NaCl and add $1/10^{th}$ volume of Cibacron blue (as a 3% wt/volume water solution) to this suspension and mix this suspension for at least 16 hrs at room temperature. The excess dye was removed by at least 3 rounds of sedimentation-resuspension in 100 mM NaCl until blue dye was no longer detected in supernatant, followed by at least 3 rounds sedimentation-resuspension in water or until blue dye was no longer detected in supernatant, at least 3 rounds. The particles were then suspended in water at final particle density of 50 mg/mL.

EXAMPLE 15

Process to Make Epoxy-DTT-DVS Ligand Coating (a Thiophilic-Like Ligand) for Protein Chromatography The process for producing epoxy-DTT-DVS ligand coating consisted of suspending the particles from Example 12 in 100 mM borate buffer with 100 mM NaH$_2$PO4 (pH~8), at a concentration of 1 to 10 wt particle to suspension volume, then adding 1 volume of 1M DTT and mixing this for 16 hr at room temperature. The particles are then washed three rounds in 100 mM NaCl. The particles were resuspended in 100 mM borate buffer (pH~9) at a particle concentration of 1:10. To this suspension is added $1/10$ volume of divinyl sulfone, mixed and incubated for 4 hours at room temperature. These particles are subjected to 3 rounds of sedimentation-resuspension with 100 mM borate buffer. The particles are resuspended in either 100 mM borate buffer at 1:10 ratio and mercaptoethanol (MCE) is added to a 100 mM concentration or particles were resuspended in phosphate buffer (pH~9) and propylene glycol was added to a 100 mM. These particles were incubated for ~16 hrs, with constant mixing (rotational mixing) at room temperature. Both types of particles were washed by sedimentation-resuspension process with 50 volumes of 100 mM NaCl. This process was repeated 3 times. The final solutions were suspended in 660 mM Na$_2$SO$_4$150 mM NaPO4 buffer (pH~7.0, as measured with pH indicator strips).

EXAMPLE 16

Process to Produce Amino-Silane Coated Kaolin

The process for producing amino-silane coated particles was similar to Example 12 with the exception of the substituting 3-aminopropyltriethoxysilane (amino-silane) for 3-glycidoxytrimethoxysilane (epoxy-silane) at the same volume to suspension ratio. All other steps remain the same except the final suspension is stored in water or in 10 mM NaCl.

EXAMPLE 17

Process to Produce Amino-Silane Coated Metal Oxide Nanoparticles

The process for producing amino-silane coated metal oxide particles was to resuspend the metal oxide nanoparticles at a 1 to 10 ratio (wt to volume) in 50 mM HCl and incubated at room temperature from 1 hour under constant mixing. These particles were washed with distilled water by the sedimentation-resuspension process until the pH of the supernatant was the same as the distilled water. The process to coat these particles with amino-silane was then similar to silanization steps of Example 3 with the exception of the substituting 3-aminopropyltriethoxysilane (amino-silane) for 3-glycidoxytrimethoxysilane (epoxy-silane) at the same volume to suspension ratio. All other steps remain the same except the final suspension is stored in water or in 10 mM NaCl.

EXPERIMENT 18

Process to Make Cibacron Blue-Amino-Silane Coated Particles from Amino Silane Coated Nanoparticles The process for producing Cibacron blue coated particles was to resuspend the amino-silane coated particles from Examples 16 or 17 in 100 mM NaCl at a 1 to 10 ratio of wt of particle per milliliter of suspension, and add $1/10^{th}$ volume of Cibacron blue (3% wt/volume water solution) to this suspension and continually mix for at least 16 hrs at room temperature. The excess dye was removed by at least 3 rounds of sedimentation-resuspension in 100 mM NaCl until blue dye was no longer detected in supernatant, followed by at least 3 rounds sedimentation-resuspension in water or until blue dye was no longer detected in supernatant, at least 3 rounds. The particles were then suspended in water at final particle density of 50 mg/mL.

EXAMPLE 19

Process to Make Borate Treated Kaolin Nanoparticles

The acid washed kaolin nanoparticles were prepared first suspending the kaolin (CAS# 1332-58-7) nanoparticles, Englehardt, ASP G90 in deionized water at a wt to volume of 1 to 3. This colloidal suspension was incubated for a minimum of 16 hrs. The nanoparticles were washed by a sedimentation-resuspension process; sedimenting the nanoparticles out of suspension by centrifugation at 4000 G for 10 min resuspending the kaolin in water at the same ratio and repeating this process until the supernatant were clear with no sign of opalescence. This final kaolin pellet was resuspended 1 to 3 with water and an equal volume of 10% sulfuric acid is added to the suspension. This sulfuric/kaolin slurry was mixed and incubated at room temperature from 1 to 2 hours, then washed with distilled water by the sedimentation-resuspension process until the pH of the supernatant was the same as the distilled water. To this suspension, at a 1 to 10 ratio was added $1/50^{th}$ volume of 500 mM NaF, and incubated mixed and the subjected to one round of sedimentation-resuspension with distilled water, with the pellet being resuspended in 100 mM borate buffer (1:1 100 mM boric acid to 100 mM sodium tetraborate) a ratio of 1 to 10 and mix for at least 16 hours. This suspension was subjected to three rounds of the sedimentation-resuspension with 10 mM borate buffer. The particles were stored in this condition until ready for dilution in 10 mM borate buffer.

EXAMPLE 20

Process to Make Borate Treated Aluminum Oxide

The process was to resuspend aluminum oxide at a 1 to 10 ratio (wt to volume) in 50 mM HCl and incubated at room temperature from 1 hour under constant mixing. These particles were washed with distilled water by the sedimentation-resuspension process until the pH of the supernatant was the same as the distilled water. The nanoparticle pellet was resuspended in 100 mM borate buffer (1:1 100 mM boric acid to 100 mM sodium tetraborate) a ratio of 1 to 10 and mix for at least 16 hours. This suspension was subjected to three rounds of the sedimentation-resuspension with 10 mM borate buffer. The particles were stored in this condition until ready for dilution in 10 mM borate buffer.

EXAMPLE 21

Process to Make Borate Treated Titanium Oxide

The process was to resuspend titanium oxide at a 1 to 10 ratio (wt to volume) in 50 mM HCl and incubated at room temperature from 1 hour under constant mixing. These particles were washed with distilled water by the sedimentation-resuspension process until the pH of the supernatant was the same as the distilled water. The nanoparticle pellet was resuspended in 100 mM borate buffer (1:1 100 mM boric acid to 100 mM sodium tetraborate) a ratio of 1 to 10 and mix for at least 16 hours. This suspension was subjected to three rounds of the sedimentation-resuspension with 10 mM borate buffer. The particles were stored in this condition until ready for dilution in 10 mM borate buffer.

EXAMPLE 22

Process to Make Borate Treated Tungsten Oxide

The process was to resuspend tungsten oxide at a 1 to 10 ratio (wt to volume) in 50 mM HCl and incubated at room temperature from 1 hour under constant mixing. These particles were washed with distilled water by the sedimentation-resuspension process until the pH of the supernatant was the same as the distilled water. The nanoparticle pellet was resuspended in 100 mM borate buffer (1:1 100 mM boric acid to 100 mM sodium tetraborate) a ratio of 1 to 10 and mix for at least 16 hours. This suspension was subjected to three rounds of the sedimentation-resuspension with 10 mM borate buffer. The particles were stored in this condition until ready for dilution in 10 mM borate buffer.

EXAMPLE 23

Process to Make Borate Treated Zirconium Oxide

The process was to resuspend zirconium oxide at a 1 to 10 ratio (wt to volume) in 50 mM HCl and incubated at room temperature from 1 hour under constant mixing. These particles were washed with distilled water by the sedimentation-resuspension process until the pH of the supernatant was the same as the distilled water. The nanoparticle pellet was resuspended in 100 mM borate buffer (1:1 100 mM boric acid to 100 mM sodium tetraborate) a ratio of 1 to 10 and mix for at least 16 hours. This suspension was subjected to three rounds of the sedimentation-resuspension with 10 mM borate buffer. The particles were stored in this condition until ready for dilution in 10 mM borate buffer.

EXAMPLE 24

Process to Make Inosine Monophosphate Coated Zirconium Oxide

The process was to resuspend zirconium oxide at a 1 to 10 ratio (wt to volume) in 50 mM HCl and incubated at room temperature from 1 hour under constant mixing. These particles were washed with distilled water by the sedimentation-resuspension process until the pH of the supernatant was the same as the distilled water. The nanoparticle pellet was resuspended in 100 mM NaCl and inosine monophospate was added to a final concentration of 2 mg per mL. This suspension was subjected to three rounds of the sedimentation-resuspension with 10 ug/mL of inosine monophosphate in 100 mM NaCl. The particles were stored in this condition until ready for dilution in 10 ug/mL of inosine monophosphate.

EXAMPLE 25

Process to Adsorb DNA on Nanoparticles Using Alcohols

The process is to add LiCl or NaCl to a 0.5 M concentration to the DNA containing solution, then add at nanoparticles in suspension to a wt to volume ration ranging from 0.001 to 1%. To this DNA sample-nanoparticle suspension is added two volumes of either Ethanol or Isopropanol, mixed and incubated for 10 to 30 min at room temperature. The particles are pelleted by centrifugation at forces ranging from 500 to 10,000 G. The supernatant is removed, the particles are washed in an alcohol solution to that can be 40% to 100 Ethanol or Isopropanol with or without NaCl or LiCl at 100 mM to 200 mM concentration. The particles are resedimented under centrifugal conditions as mentioned above, air-dried. The DNA can be eluted in a particle to volume ration that can be ranging from 1:10 to as much as 1:20000, typically from 1 to 200 to 1-1500. The temperature of elution can range from room temperature to 55° C.

EXAMPLE 26

Standard Process to Purify DNA by Alcohol Induced Partitioning Using Kaolin Particles for Adsorption Chromatography To 500 µL DNA sample in which LiCl has been added to 0.5 M and to at least 1 mM EDTA, 10 µL of phosphate-treated kaolin (example B) at concentration of 12.5 mg/mL is added, mixed by pipeting/vortex-mixing. To this DNA preparation with kaolin is added 510 µL of Isopropanol, mixed by vortex incubated at room temperature for 10 minutes suspension is mixed again incubated for an additional 20 minutes for a total of 30 minutes. The suspension is centrifuged for 4 minutes at 2000 G, the supernatant carefully removed from the pellet. 500 µL of 50% Ethanol-100 mM NaCl is added to the tube, the pellet and tube are washed by vigorous but brief vortex-mixing, and the sample is centrifuged for 2 minutes at 2000 G. The supernatant is carefully removed from the pellet, and the pellet is allowed to air dry for 10 min. The DNA is eluted from the kaolin nanoparticles by adding at least 10 µl, to 150 µl, of an elution buffer consisting of 2 mM phosphate buffer, 10 mM Tris, 4 mM acetic acid, 0.1 mM EDTA, and 20 mM NaCl. This is allowed to incubate for at least 5 minutes then mixed to resuspend the kaolin particles and incubate this suspension between 10 min to an hour. The particles are sedimented from the eluate and the eluate is transferred to a new tube, the spent pellet is discarded.

EXAMPLE 27

Protocol for DNA Extraction from Buccal Cell Sample Isolated from Mouthwash Rinses The buccal cell sample is a 10 ml, 15%wt alcohol content mouthwash (with content) that is rinsed in the mouth for 45 seconds and deposited into 50 mL conical centrifuge tube (the subject is recommended to refrain from eating or drinking and hour before the sample is retrieved. The buccal cells are pelleted by a 1500×g centrifugation for 15 minutes, the pellet is retained and the supernatant is discarded. To the pellet is added 240 µl of 30 mM NaOH and this is vortex-mix to resuspend the pellet, and lyse the cells, and this processed is done with periodic mixing at room temperature for up to 30 minutes. The pellet will disperse and be free of particulates and have a "smooth" and lump-free appearance. Once the pellet is completely disaggregated, 67.5 µL of 0.1 N HCl is added to reach a final pH in the range from 7.5 to 8.5. To this cell lysate is added 92.5 µl PBS, pH 7.4 followed by vortex-mixing for a total sample volume of 400 µl Add 20 µl Proteinase K (Invitrogen cat# 25530-049 20 mg/ml stock) and incubate for 55° C. for 20 minutes and then proceeding to the procedure of Examples "25" or "26".

EXAMPLE 28

Protocol for DNA Extraction with SDS in Stain Removal Buffer from Whole Blood

The extraction process based on disrupting blood cell samples from 50 µL or less in 500 µL of extraction buffer. The extraction buffer consist of 100 mM NaCl, 10 mM EDTA, 10 mM Tris (pH =8.0), 2% SDS, and 20 mM DTT. This extraction buffer with the blood sample was incubated for 5 min at 55° C. To digest the sample with a protease, 10 µL (200 ug) of Proteinase K (20 mg/mL stock solution) or 5 µL of Savanase (17.5U/mL) was added, mixed in the extract and incubated at 55° C. for overnight (∥16 hr). This extract was then centrifuged for 5 min at 10,000 G, the supernatant transferred to a new tube and the pellet discarded. The supernatant (protease digests) was incubated for at least 2 min at 55° C. and then 25 uL of 10 M LiCl is added and mixed. These LiCl augmented supernatants were then processed as in Example 26, though with the exceptions of substituting Ethanol for Isopropanol at the step to cause DNA to adsorb to nanoparticles.

EXAMPLE 29

Protocol for DNA Extraction with Sodium Lauroyl Sarcosine and Guanidine Hydrochloride from Whole Blood The DNA extraction process based on disrupting the cells in blood for samples that are 50 µL whole blood in an extraction volume of 500 µL of extraction buffer. Thawed whole blood was added directly to extraction solution consisting of 100 mM NaCl, 10 mM EDTA, 10 mM Tris (pH =8.0), 1% sodium lauroyl sarcosine, 900 mM, guanonidine hydrochloride, and 20 mM DTT. To this extraction mixture was added either 10 µL (200 ug) of Proteinase K (20 mg/mL stock solution) or 5 µL of Savanase (17.5U/mL) was added, mixed in the extract and incubated at 55° C. for overnight (~16 hr). This extract was then centrifuged for 5 min at 10,000 G, the supernatant transferred to a new tube and the pellet discarded. The supernatant (protease digests) was incubated for at least 2 min at 55° C. and then 25 uL of 10 M LiCl is added and mixed. These LiCl augmented supernatants were then processed as in Example 26.

EXAMPLE 30

Alternative Method to Extract the Buccal Cell DNA from Mouth Wash Aspirates

The buccal sample was collected by rinsing 10 mL of mouthwash in the mouth for 1 min. To this mouthwash buccal cell suspension was added an $\frac{1}{10}^{th}$ volume of 0.1 extraction buffer consisting of 500 mM MES, 250 mM EDTA, disodium salt, 0.1 mL of 10% solution of NP-40 and 0.8 ml of Formamide. These solutions were mixed followed by 15 min incubation at 55° C. Debris was removed from the extract by 1500 G centrifugation for 10 min, the supernatant was transferred to a new tube and the pellet was discarded. To the extract was added 0.5 mg of PEI-epoxysilane coated kaolin (Example 15) mixed to even suspension and incubated for 15 min at room temperature. After this incubation PEI kaolin nanoparticle are sedimented out of 2,000 G for 5 minutes centrifugation at room temperature. The pellet was rinsed with solution that was 200 mM LiCl/0.1% Igepal CA 630/10 mM Tris/1mM EDTA. The nanoparticles were subjected to centrifugation at 2,000 G for 2 minutes and the rinse-supernatant was discarded. The DNA was eluted from these particles by resuspending the pellets in 200 uL of DNA release buffer consisting of 200 mM CAPS sodium salt/200 mM LiCl/0.2% of SDS and incubating these pellets at room temperature or at 55° C. for a minimum of 30 minutes. The eluates are collected by pelleting the PEI coated nanoparticles by sedimentation at 10,000 G for 5 min. The DNA eluate (supernatant) is transferred to a new microfuge tube. The DNA was further purified from this eluate by process outline in Example 25 or Example 26.

EXAMPLE 31

Process to Purify Nucleic Acids Using Phosphate or Borate Treated Kaolin Particles or Borate Treated Metal Oxides Particles for Adsorption Chromatography based on Cetytrimethylammonium Bromide To 500 µL DNA sample that contains 20 mM Tris (pH from 7 to 8), 2 mM EDTA and 700 mM NaCl, add 5 to 50 µL of 10% cetyltrimethylammonium bromide (CTAB) and mix. To this DNA preparation add 10 µL of phosphate-treated kaolin (Example 11), borate treated kaolin (Example 19) or the borate treated metal oxides (Examples at "20", "21", "22", "23") at a concentration of 12.5 mg/mL and mixed by pipeting/vortex-mixing. Dilute this DNA preparation by adding 500 to 700 µL of water, mixed by vortex incubate from 4° C. to room temperature for 10 to 30 with occasional mixing. The suspension is centrifuged for 4 minutes at 2000 G, the supernatant care-fully removed from the pellet. To this pellet is added 500 µL of 50% Ethanol-500 mM LiCl and the pellet is fully resuspended in this solution. This suspension is centrifuged for 2 minutes at 2000 G. The pellet is resuspended in a 500 µL solution of 700 mM LiCl/10 mM Tris (pH 8)/1 mM EDTA/10 mM borate buffer (pH 8). To this particle eluate is added 500 µL of Ethanol and the suspension is incubated for 30 min, then centrifuged for 4 minutes at 2000 G. The pellet is washed in 50% Ethanol-100 mM NaCl and centrifuge for 2 minutes at 2000 G, the supernatant is carefully removed from the pellet, and the pellet is allowed to air dry for 10 min. The DNA is eluted from the nanoparticles by adding at least 10 µL to 150 µL of an elution buffer consisting of 2 mM phosphate buffer, 10 mM Tris, 4 mM acetic acid, 0.1 mM EDTA, and 20 mM NaCl. This is allowed to incubate for at least 5 minutes then mixed to resuspend the particles and incubate this suspension between 10 min to an hour. The particles are sedimented from the eluate and the eluate is transferred to a new tube, the spent pellet is discarded.

EXAMPLE 32

Process to Purify rRNA Using Inosine Monophosphate Coated Zirconium Oxide Particles E.coli rRNA adsorption to inosine monophosphate coated zirconium oxide as was demonstrated in FIG. 8 using the inosine monophosphate (IMP) coated zirconium oxide nanoparticle were made according to "Example 24". The adsorption process used for this example was to add 5 uL of a 2 ug solution of rRNA (E.coli) to 50 uL solution containing 0.1% sodium lauroyl sarcosine, 1.0 M LiCl, 20 mM Tris-OH/Tris-HCl (pH 8), 2 mM EDTA for sample displayed in lane 7, for sample displayed in lane 8 he same as lane 7 sample only with the 20% formamide, for the sample displayed in lane 9 the same as in lane 7 only with the addition of guanidine hydrochloride (Gu-HCl) to 600 mM. To this was added 20 uL of IMP-ZrO$_2$ suspension (~1 mg). The suspension was incubated for 30 min, then centrifuged for 4 min at 2000 G, the supernatants were removed from the pelleted particles. These particles were resuspended in 200 uL of 1 × binding solution (0.1% sodium lauroyl sarcosine, 0.5 M LiCl, 10 mM Tris-OH/Tris-HCl (pH 8), 1 mM EDTA). These suspension were then subjected of centrifugation for 2 min at 2000 G, the pellet was retained the supernatant were discarded. The pellets were then resuspended in elution buffer that was 50% formamide, 10 mM Borate buffer (pH~9.2), 10 mM Tris, 4 mM acetic acid, 20 mM NaCl, 2 mM phosphate buffer and were incubated in this for 30 min. Half of the eluates were analyzed by 1% agarose TBE gel.

EXAMPLE 33

Process to Purify Nucleic Acids Using Phosphate or Borate Treated Kaolin Particles or Borate Treated Metal Oxides Particles for Adsorption Chromatography based on High Concentration of LiCl to Fractionate High Molecular Weight Single Stranded RNA from the Rest of Cellular Nucleic Acids To 500 µL DNA sample that contains 20 mM Tris (pH from 7 to 8), 2 mM EDTA add 10 µL of phosphate-treated kaolin (Example 11), borate treated kaolin (Example 19) or the borate treated metal oxides (Examples at "20", "21", "22", "23") at a concentration of 12.5 mg/mL and mixed by pipeting/vortex-mixing. Dilute this nucleic acid preparation by adding 125 µL of 10 M LiCl and mix. Place at 4° C. to room temperature for 10 to 30 with occasional mixing. The suspension is centrifuged for 4 minutes at 2000 G, the supernatant carefully removed from the pellet and retained since this contains the DNA and small nuclear/cytoplasmic RNA. This supernatant fraction can be process by Example Q to desalt and concentrate this subset of nucleic acids. To the pellet add 500 µL of 2 M LiCl, and fully resuspended the pellet in this solution. Centrifuge this suspension for 2 minutes at 2000 G. The pellet is washed in 50% Ethanol and centrifuge for 2 minutes at 2000 G, the supernatant is carefully removed from the pellet, and the pellet is allowed to air dry for 10 min. The RNA is eluted from the nanoparticles by adding at least 10 µL to 150 µL of an elution buffer consisting of 2 mM phosphate buffer, 10 mM Tris, 4 mM acetic acid, 0.1 mM EDTA, and 20 mM NaCl (with or without 0.1% detergent). This is allowed to incubate for at least 5 minutes then mixed to resuspend the nanoparticles and incubate this suspension between 10 min to an hour. The particles are sedimented from the eluate and the eluate is transferred to a new tube, the spent pellet is discarded.

EXAMPLE 34

Process to Purify Nucleic Acids using Phosphate Treated Kaolin Particles or Borate Treated Metal Oxides Particles for Adsorption Chromatography based on Divalent Cations To 500 µL DNA sample that contains 20 mM Tris (pH from 7 to 8), 2 mM EDTA add 10 µL of phosphate-treated (Example 11), borate treated kaolin (Example 19) or the borate treated metal oxides (Examples at "20", "21", "22", "23") at a concentration of 12.5 mg/mL and mixed by pipeting/vortex-mixing. Dilute this nucleic acid preparation by adding 125 µL of 500 mM $MnCl_2$ and mix. Place at 4° C. to room temperature for 10 to 30 with occasional mixing. The suspension is centrifuged for 4 minutes at 2000 G. The pellet is washed in 500 mL of 100 mM $MnCl_2$ and centrifuge for 2 minutes at 2000 G and the supernatant is discarded. To the pellet is added 10 µL 500 EDTA and 10 µL of 1 M Tris, pH 8.0 and incubated for 5 min. The pellet is resuspended in this solution of Tris/EDTA solution followed by the addition of 500 µL of 500 mM LiCl, and the pellet is fully resuspended in this solution. The sample is then processed as in Example 26.

EXAMPLE 35

Process to Purify Nucleic Acids using Phosphate Treated or Borate Treated Kaolin Particles or Borate Treated Metal Oxides Particles for Adsorption Chromatography based on Polyethylene Glycol To 500 µL DNA sample that contains 20 mM Tris (pH from 7 to 8), 2 mM EDTA, 700 mM NaCl, add 10 µL of phosphate-treated kaolin (Example 11), borate treated kaolin (Example 19) or the borate treated metal oxides (Examples at "20", "21", "22", "23") at a concentration of 12.5 mg/mL and mixed by pipeting/vortex-mixing. Dilute this nucleic acid preparation by adding 1 volume of 20% wt to volume of polyethylene glycol (PEG), MW 6000 to 8000, diluted in 700 mM NaCl and mix. Place at 4° C. to room temperature for 10 to 60 min with occasional mixing. The suspension is centrifuged for 4 minutes at 2000 G. The pellet is washed in 500 mL of 10% PEG/500 mM NaCl and centrifuge for 2 minutes at 2000 G and the supernatant is discarded. The sample is then processed as in Example 26.

EXAMPLE 36

PCR Process to Evaluate DNA Extracts

PCR was the process to compare and evaluate DNA extraction process was based on a nuclear chromosome encoded gene, amelogenin, encoded on both the X and Y chromosome. The primer sequences were for SEQ ID NO. 1 was 5'- AGA TGA AGA ATG TGT GTG ATG GAT GTA -3', and for SEQ ID NO. 2 the sequence was 5' - GGG CTC GTA ACC ATA GGA AGG GTA - 3' primer sequences based on the amylogenin sequence in GenBank with accession number AY040206. The PCR product is a 558 base pair long fragment. The most commonly used PCR reaction was either 25 µL or 50 µL volume, composed of 1× Roche PCR Buffer, 1.5 mM to 2 mM MgC12, 0.4 uM primers, 0.2 mM dNTP's, 0.16 mg/ml BSA, and 0.4 µl of Fast Start Taq at 5 U/µl. The PCR conditions were for the first step to be at 94 degrees C. for 4 minutes, followed by 35 cycles composed of these three steps of 94° C. for 1 min followed by 65° C. for 1 min, followed by 72° C. for 1 min. After these 35 cycles, the reactions were incubated at 72 degrees ° C. for 7 min followed by a holding step at 15° C. until the reaction were stopped. All of PCR results were evaluated by agarose or SFR gel electrophoresis of ⅕ of the reaction volume in agarose gels using Tris-Borate-EDTA buffer. The molecular size controls were the DNA ladder of the 1 Kb ladder from Invitrogen (1 Kb marker cat# 15615-016). The semi-quantitative controls for the amylogenin allele controls were a null or DNA negative control; a reaction that did not contain any DNA; and four human DNA positive controls with a fixed and known amount of human DNA (Roche Human Genomic DNA catalog # 1691112) as PCR templates. The human DNA content for these controls were 10 ng, 1 ng, 0.1 ng and 0.01 ng human DNA per PCR reaction.

EXAMPLE 37

A Process to Isolate Serum Protein using Cibacron Blue Nanoparticles

The serum was diluted 10 µL of serum was diluted with 40 µL of water. To this solution was added 0.125 to 1 mg of nanoparticles coated with Cibacron blue (See examples "16" or "20") and incubate for 10 min at room temperature. The "blue nanoparticles were subjected to centrifugation at 2000 G for 5 min, washed with PBS, then re-pelleted and eluted in protein loading buffer for Tris-acetate gels and processed for electrophoretic analysis. The particles were pelleted from the eluate by 10 min centrifugation at 10,000 G. The protein eluate was transferred to a new tube.

EXAMPLE 38

A Process to Isolate Serum Protein using Cibacron Blue Nanoparticles in Water

The process as described in Example 37 was followed, except that the PBS wash was not used.

EXAMPLE 39

A Process to Isolate Serum Protein using Cibacron Blue Nanoparticles in PBS

The process as described in Example 37 was followed, except that the serum was diluted in phosphate buffered saline at pH of 7.4.

EXAMPLE 40

A Process to Isolate Serum Protein using Cibacron Blue Nanoparticles in Tris Buffer The process as described in Example 37 was followed, except that the serum was diluted in 30 mM Tris, at a pH of about 8.2.

EXAMPLE 41

A Process to Isolate Serum Protein using Cibacron Blue Nanoparticles in MES/Tris pH~5.9

The process of Example 37 was followed, except that the serum was diluted in 30 mM MES/Tris pH about 5.9.

EXAMPLE 42

A Process to Isolate Serum Protein using Cibacron Blue Nanoparticles in 30 mM Tris+100 mM NaCl pH =~8.3

The process of Example 37 was followed, except that the serum was diluted in 30 mM Tris+100 mM NaCl, pH of about 8.3.

EXAMPLE 43

A Process to Isolate Serum Immunoglobulin Proteins using Thiophilic Ligand, Epoxy Silane-DTT-DVS Ligand Serum was diluted 1:2 with 10 mM Tris-pH 7/1M NaSO4 (1.5 × T-particle Binding Buffer) concentrate or added at of less than 20 µL per 500 µL to 1× T-particle Binding Buffer) followed by the addition of nanoparticles coated with epoxy-silane-DTT-DVS ligand (or T-particles) as describe in Example 15 were added at a concentration that ranged from 0.1 to 5 mg per milliliter of diluted serum. These were allowed to bind for 15 min at room temperature. The T particles were sedimented at 2000 G for 4 min and the pellet was retained. The pellet was resuspended in 1 × T-particle Binding Buffer and then centrifuged for 2 min at 2000 G. The supernatant was discarded and the pellet was resuspended in 10 to 50 µL of PBS and incubated for 15 min. The particles were pelleted from the eluate by 10 min centrifugation at 10,000 G. The protein eluate was transferred to a new tube and analyzed

EXAMPLE 44

A Process to Isolate Serum Immunoglobulin Proteins using Thiophilic Ligand, Epoxy Silane-DTT-DVS Ligand The same process as in Example 43 was followed, except that the proteins were eluted from the pellet in protein electrophoresis loading buffer and heated per instructions for the Invitrogen protein loading buffers. The particles were pelleted from the eluate by 10 min centrifugation at 10,000 G. The protein eluate was transferred to a new tube and loaded on a gel for analysis.

EXAMPLE 45

A Process to Isolate Salivary Immunoglobulin Proteins using Thiophilic Ligand, Epoxy Silane-DTT-DVS Ligand Salivary immunoglobulin was collected 10 ml of saline solution that was the collected by rinsing in the mouth for 60 seconds and deposited this rinse-ate into 50 mL conical centrifuge tube (the subject is recommended to refrain from eating or drinking and hour before the sample is retrieved). The cells and other debris were removed by centrifugation at 1500 × g for 15 minutes, the supernatant is retained by transferring to a new tube. The pellet was discarded. To the supernatant were added T-particles at a concentration that ranged from 0.1 to 5 mg per milliliter and this suspension was thoroughly mixed. To this suspension was added 2 volumes of 10 mM Tris-pH 7/1M NaSO4 (1.5 × T-particle Binding Buffer). The suspension was incubated for 15 min to 30 min at room temperature. The T particles were sedimented at 2000 G for 4 min and the pellet was retained. The pellet was resuspended in 1 × T-particle Binding Buffer and then centrifuged for 2 min at 2000 G. The supernatant was discarded and the pellet was resuspended in 10 to 50 µL of PBS and incubated for 15 min. The particles were pelleted from the eluate by 10 min centrifugation at 10,000 G. The protein eluate was transferred to a new tube and analyzed.

EXAMPLE 46

A Process to Isolate Salivary Immunoglobulin Proteins using Thiophilic Ligand, Epoxy Silane-DTT-DVS Ligand Salivary immunoglobulin was processed as in Example 45 with the exception that the proteins were eluted from the T particles in protein gel sample buffer.

EXAMPLE 47

PCR Analysis of Whole Blood Extracts Extracted with Sodium Lauryol Sarcosine and Guanidine Hydrochloride.

Electrophoretic analysis with 2% SFR agarose gel of PCR products generated from the DNA extracted from whole blood using phosphate/fluoride treated kaolin (Example 11). The PCR amplicon is a 558 by fragment from human amylogenin gene. The extraction process as described in "Example T" based on 1% sodium lauryol sarcosine and 900 mM guanidine hydrochloride, was use to extract DNA from the following sample volumes of whole blood (frozen then thawed) 0.05 µl, 0.5µL, 1 µL, 5 µL, and 50 µL. The samples from 1 µL of whole blood used Savanase at the protease where the other samples used Proteinase K. As illustrated in FIG. 7, lanes 1 through 4 are the human DNA controls and contain a known amount of DNA. The amounts were 10 ng (lane 1), 1 ng (lane 2), 0.1 ng (lane 3), and 0.01 ng (lane 4). The PCR product of the reaction displayed in lane 5 is the null control, that is the reaction that is done without any template DNA added. The PCR products from the blood extracts are displayed in lanes 6 through 16. Lanes 6 and 7 are the product from an extract of 50 µL of whole blood, in which 1 µL of the DNA eluate of 150 ∞L, was diluted 1:19, and 1 µL of that dilution was added to the PCR as the template source. Lanes 8 and 9 are the product from an extract of 5 µL of whole blood, in which 1 µL of the DNA eluate of 50 L, was diluted 1:5, and 1 μL of that dilution was added to the PCR as the template source. Lanes 10 and 11 are the product from an extract of 0.5 μL of whole blood, in which 1 μL of the DNA eluate of 25 μL was added to the PCR as the template source. Lanes 12 and 13 are the products from an extract of 0.05 μL of whole blood, in which 8 μL of the DNA eluate of 25 μL was added to the PCR as the template source. Lanes 14, 15 and 16 are the product from an extract of 1 μL of whole blood, in which 1 μL of the DNA eluate of 25 μL, was diluted 1:1, and 1 μL of that dilution was added to the PCR as the template source. Each lane represents one fifth of the PCR product, 5 μL from 25 μL PCR reaction. Lane 17 1 μg of the 1 kb dsDNA molecular size ladder. For all samples except extracts used for lanes 14 and 15, the DNA adsorption process was to use 1 volume of isopropanol and to wash the particle in 50% ethanol with 100 mM NaCl. For the extract analysed in lane 14, the process differed in the particle alcohol wash step, in which the solution was 66% ethanol with 100 mM NaCl. For the extract analysed in lane 15, the process differed in which adsorption was with 1 volume of ethanol the wash step was like the majority of the samples, 50% ethanol with 100 mM NaCl.

EXAMPLE 48

PCR Analysis of Whole Blood Extracts Extracted with Sodium Dodecyl Sulfate (SDS)

Electrophoretic analysis with 2% SFR agarose gel of PCR products generated from the DNA extracted from whole blood using phosphate/fluoride treated kaolin (Example 11). The PCR amplicon is a 558 by fragment from human amylogenin gene. The extraction process as described in "Example 28" based on 2% sodium dodecyl sulfate (SDS) and extract DNA from the following sample volumes of whole blood (frozen then thawed) 0.05 μL, 0.5 μL, 1 μL, 5 μL, and 50 μL. The samples from 1 μL of whole blood used Savanase at the protease where the other samples used Proteinase K.

As illustrated in FIG. 6, lanes 13 through 17 are the human DNA controls that contain a known quantity of DNA. The amounts were 10 ng (lanel 3), 1 ng (lane 14), 0.1ng (lane 15), and 0.01ng (lane 16). The PCR product of the reaction displayed in lane 17 is the null control, that is the reaction that is done without any template DNA added. The PCR products from the blood extracts are displayed in lanes 2 through 12. Lanes 2 and 3 are the products from an extract of 50 μL of hole blood, in which 1 μL of the DNA eluate of 150 μL, was diluted 1:19, and 1 μL of that dilution was added to the PCR as the template source. Lanes 4 and 5 are the product from an extract of 5 μL of whole blood, in which 1 μL of the DNA eluate of 50 μL, was diluted 1:5, and 1 μL of that dilution was added to the PCR as the template source. Lanes 6 and 7 are the products from an extract of 0.5 μL of whole blood, in which 1 μL of the DNA eluate of 25 μL was added to the PCR as the template source. Lanes 8 and 9 are the products from an extract of 0.05 μL of whole blood, in which 8 μL of the DNA eluate of 25 μL was added to the PCR as the template source. Lanes 10, 11 and 12 are the product from an extract of 1 uL of whole blood, in which 1 μL of the DNA eluate of 25 L, was diluted 1:1, and 1 μL of that dilution was added to the PCR as the template source.

In FIG. 6, each lane represents one fifth of the PCR product, 5 μL from 25 μL PCR reaction. Lane 1 is 1 ug of the 1 kb dsDNA molecular size ladder. For all samples except extracts used for lanes 10 and 11, the DNA adsorption process was to use 1 volume of ethanol and to wash the particle in 50% ethanol with 100 mM NaCl. For the extract analyzed in lane 10, the process differed in the particle alcohol wash step, in which the solution was 66% ethanol with 100 mM NaCl. For the extract analyzed in lane 11, the process differed in which adsorption was with 1 volume of isopropanol the wash step was like the majority of the samples, 50% ethanol with 100 mM NaCl. The gel was 2% SFR agarose in TBE run at 150 volts for 45 minutes.

EXAMPLE 49

DNA Adsorption using Borate Treated Metal Oxides, of Zirconium, Titanium, or Tungsten and Phosphate/Fluoride Treated Kaolin Electrophoretic analysis of DNA adsorption using borate treated metal oxides, of zirconium, titanium, or tungsten and phosphate/fluoride treated kaolin and the RNA adsorption to inosine monophosphate coated zirconium oxide. Half of each of the 1 ug DNA samples of Lambda phage DNA fragments (HinD III restriction endonuclease digests) concentrated by the nanoparticle adsorption are displayed in lanes 1 through 5 in FIG. 8. Different nanoparticles were tested using the DNA adsorption process described in Example 26. For the DNA eluate displayed in lane 5 the process of Example 26 was performed (as stated) with phosphate treated kaolin and the borate treated metal oxide nanoparticles (See (Examples "11", "20", "21", "22", "23"). The samples displayed in lanes 1 through 4 used borate treated metal oxides as the adsorption platform; in lane 1, the DNA was eluted from borate treated aluminum oxide, in lane 2, the DNA was eluted from borate treated titanium oxide, in lane 3, the DNA was eluted from borate treated tungsten oxide, in lane 4, the DNA was eluted from borate treated zirconium oxide. Under the conditions used for this alcohol adsorption, the borate treated aluminum oxide did not perform as well as the other particles.

EXAMPLE 50

*E.coli* rRNA Adsorption to Inosine Monophosphate Coated Zirconium Oxide

These inosine monophosphate (IMP) coated zirconium oxide nanoparticles were made according to Example 24. The adsorption process used for this example was to add 5 μL, of a 2 ug solution of rRNA (*E.coli*) to 50 μL solution containing 0.1% sodium lauroyl sarcosine, 1.0 M LiCl, 20 mM Tris-OH/Tris-HCl (pH 8), 2 mM EDTA for sample displayed in lane 7 in FIG. 8, for the sample displayed in lane 8 the same as 7sample only with the 20% formamide, for the sample displayed in lane 9 the same as in lane 7 only with the addition of guanidine hydrochloride (Gu-HCl) to 600 mM, all in FIG. 8. To this was added 20 μL of IMP-$ZrO_2$ suspension (~1 mg). The suspension was incubated for 30 min, then centrifuged for 4 min at 2000 G, the supernatants were removed from the pelleted particles. These particles were resuspended in 200 μL of 1 × binding solution (0.1% sodium lauroyl sarcosine, 0.5M LiCl, 10 mM Tris-OH/Tris-HCl (pH 8), 1 mM EDTA. These suspension were then subjected of centrifugation for 2 min at 2000 G, the pellet was retained the supernatant were discarded. The pellets were then resuspended in elution buffer that was 50% formamide, 10 mM Borate buffer (pH~9.2), 10 mM Tris, 4 mM acetic acid, 20 mM NaCl, 2 mM phosphate buffer and were incubated in this for 30 min. Half of the eluates were analyzed by 1% agarose TBE gel.

EXAMPLE 51

DNA Isolated from Buccal Cells Collected by Swab Sampling

Figure 9:
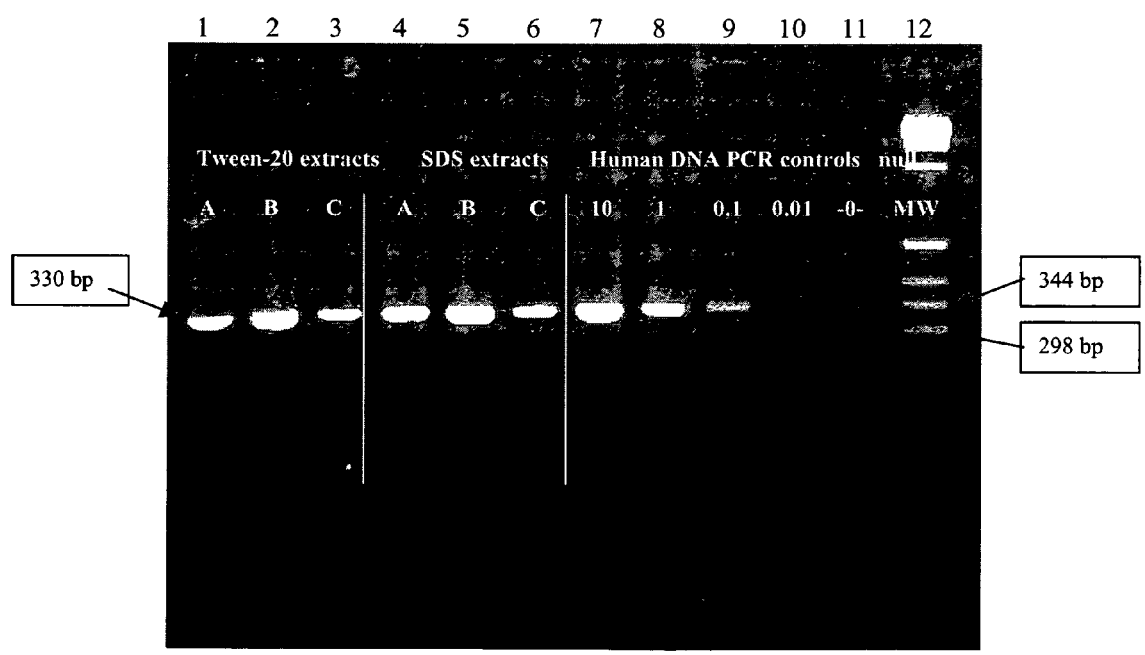
FIG. 9:
Electrophoretic Gel analysis of DNA, isolated from a buccal cell sample collected by swabs, with 2% SFR agarose gel of PCR products generated from the DNA extracted from buccal cells collected by swab with SDS or Tween 20 using phosphate/fluoride treated kaolin (Example 11). The PCR amplicon is a 558 by fragment from human amylogenin gene. (See Example 51).

DNA was isolated from buccal cell sample using Fitzco swab collection. Three subjects were harvested, A through C, one sample of each subject was extracted using Tween-20 as the detergent and the second set used SDS as the detergent. The two extraction processes were as describe in Example 47 with proteinase K with one exception for three of the samples Tween-20 was used instead of SDS. The nanoparticle adsorption process was as described in Example 26 with the DNA eluted in a total volume of 25 μL. The PCR process analysed 0.5 μL of the DNA eluate from each sample using primers against the chromosomal allele GSTpi which yields a PCR amplicon product of 330 by length. For the TBE, 2% SFR agarose gel, 5 uL of the PCR reaction was analysed per well. As depicted in FIG. 9, the products analyzed in lanes 1 through 3 were extracted with Tween-20 detergent, and for lanes 4 through 6 were extracted with SDS. Lanes 7 though 10 were the PCR products from the human DNA controls; lane 7 product from a PCR reaction started with 10 nanograms of DNA, lane 8 product from a PCR reaction started with 1 nanograms of DNA lane 9 product from a PCR reaction started with 0.1 nanograms of DNA, lane 10 product from a PCR reaction started with 0.01 nanograms of DNA PCR products analysed in lane 11 are the DNA null control, or reaction in which no DNA was added. Lane 12 is the molecular weight DNA ladder of 1 kb and smaller fragments. For this analysis only one quarter of the buccal sample was processed, the estimation, based on the human DNA controls was that the yield per sample (¼) was between 100 to 500 ng, or 400 to 2000 ng per total sample, a range typical for buccal cheek swabs.

EXAMPLE 52

Figure 10:
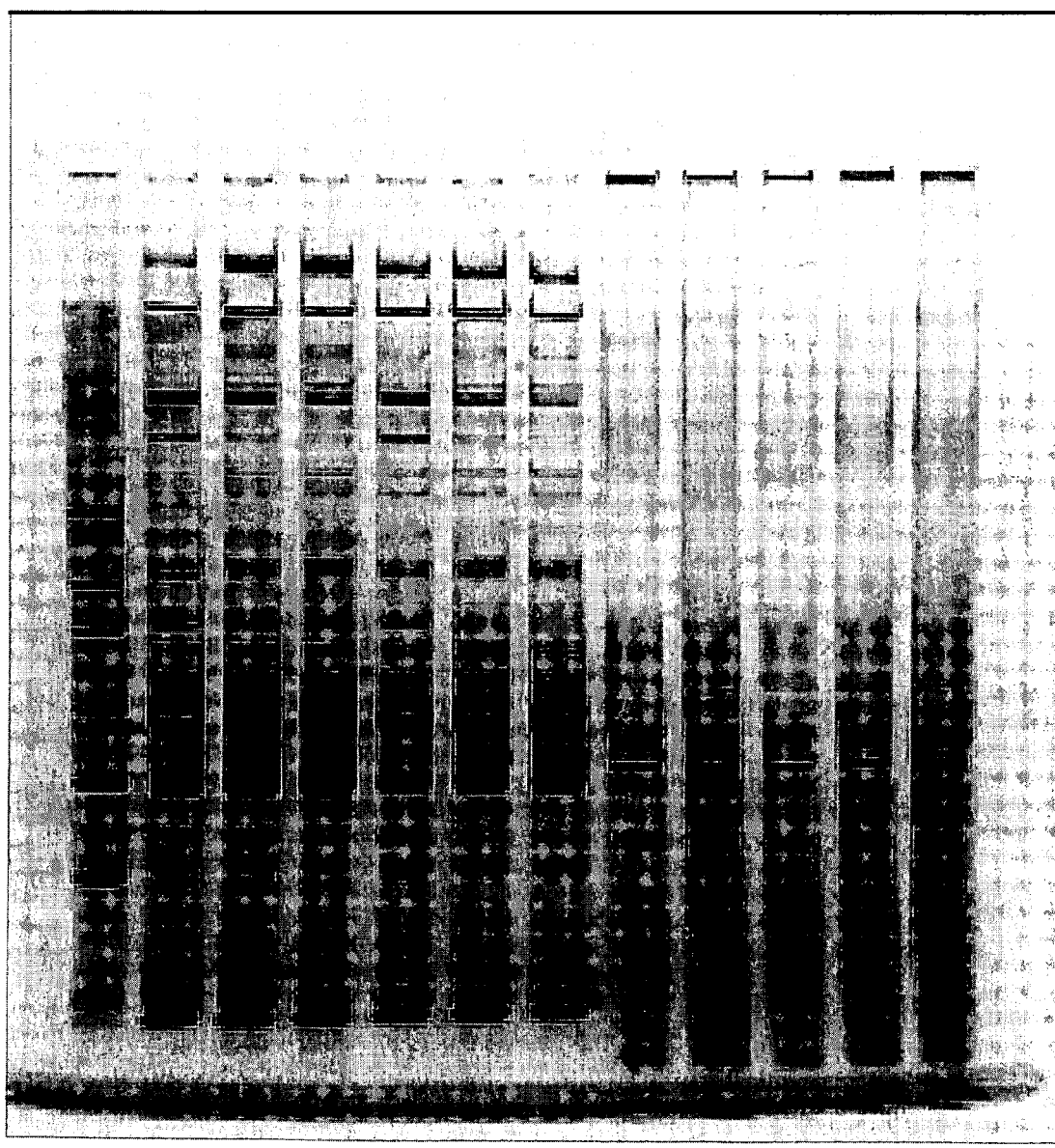
FIG. 10:
Silver stain 3-8% Tris-acetate gel polyacrylamide gel of proteins that bound to kaolin nanoparticle with the epoxy-silane-DTT-DVS thiophilic ligand. Two types of particles were tested, M-type and P-type on two sources of immunoglobulin, serum or saliva. (See Example 52).

Silver Stain 3-8% Tris-Acetate Gel Polyacrylamide Gel of Proteins that Bound to Kaolin Nanoparticle with the Epoxy-Silane-DTT-DVS Thiophilic Ligand Two types of particles were tested, M-type and P-type on two sources of immunoglobulin, serum or saliva. The "M-type" particles were the epoxy-silane-DTT-DVS ligand terminated with mercaptoethanol and the "P-type" particles were the epoxy-silane-DTT-DVS ligand terminated with propylene glycol sample represents 1/60$^{th}$ of the eluate from these thiophilic ligand coated particles (See Example 15). The process was that described in Example 43 for serum samples and Example 45 for saliva samples. Three concentrations of particles were used for the serum samples, 5 uL vs 10 uL or 20 uL of 50 mg/mL suspension of the nanoparticle suspension, added to 500 uL of diluted sample. For the salivary samples 20 uL of thiophilic ligand coated nanoparticle suspension was used per 0.5 mL mouth rinse of saline wash. FIG. 10 depicts the results of the testing. The samples were "lane MW", the protein molecular weight standards, with size indicated with the arrows. For "lane 1", serum sample of 1 uL of serum in 0.5 mL of PBS and 5 ul of P-type particle slurry was used, for "lane 2", serum sample of 1 uL of serum in 0.5 mL of PBS and 10 ul of P-type particle slurry was used, and for "lane 3", serum sample of 1 uL of serum in 0.5 mL of PBS and 20 ul of P-type particle slurry was used. For "lane 4", serum sample of 1 uL of serum in 0.5 mL of PBS and 5 ul of M-type particle slurry was used, for "lane 5", serum sample of 1 uL of serum in 0.5 mL of PBS and 10 ul of M-type particle slurry was used, and for "lane 6", serum sample of 1 uL of serum in 0.5 mL of PBS and 20 ul of M-type particle slurry was used. For lanes 7 through 11, the sample was saliva with the process as describe in Example 45, for "lane 7", 0.5 mL of mouth-saline rinse-ate subject #1 and 20 ul of P-type particle were used., for "lane 8", 0.5 mL of mouth-saline rinse-ate subject #2 and 20 ul of P-type particle were used., and for "lane 9", 0.5 mL of mouth-saline rinse-ate from subject #3 and 20 ul of P-type particle were used. For "lane 10", 0.5 mL of mouth-saline rinse-ate subject #1 and 20 ul of M-type particle were used and for "lane 11", 0.5 mL of mouth-saline rinse-ate subject #2 and 20 ul of M-type particle were used.

EXAMPLE 53

Figure 11:
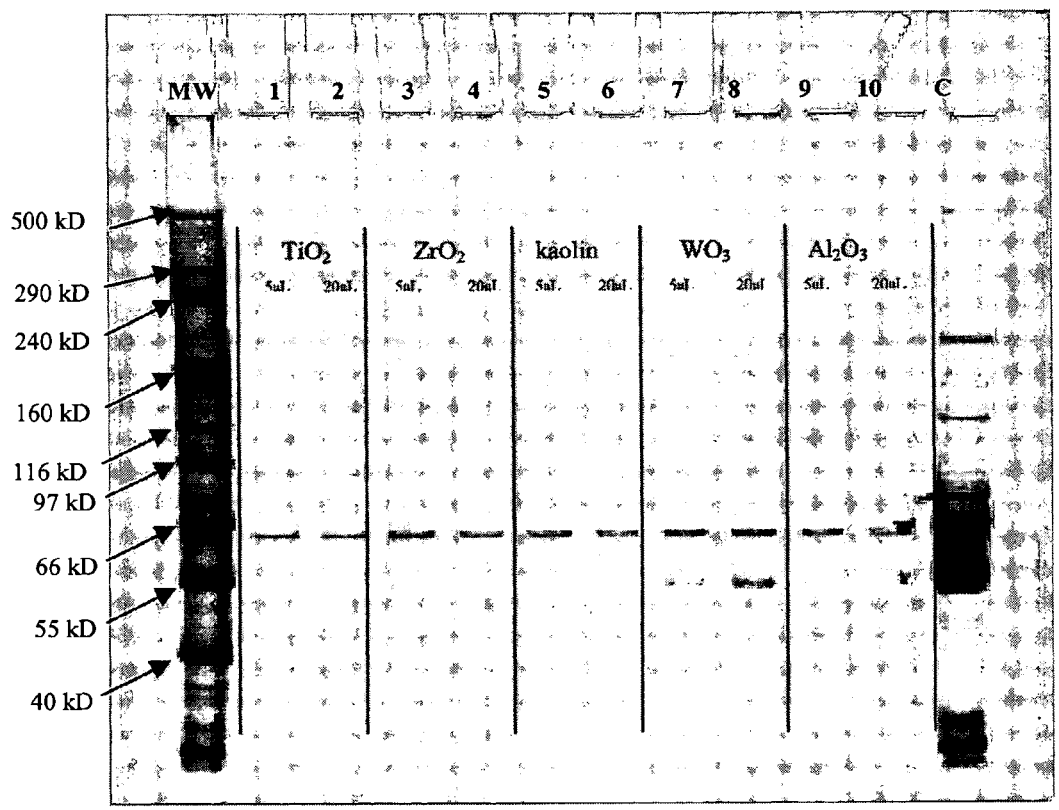
FIG. 11:
Chromatography of Serum Proteins with Cibacron blue-amino-silane coated nanoparticles. The analysis of the results is displayed in the silver stain 3-8% Tris-acetate gel polyacrylamide gel. (See Example 53).

Chromatography of Serum Proteins with Cibacron Blue-Amino-Silane Coated Nanoparticles The serum proteins were fractionated with Cibacron Blue, amino-silane coated nanoparticles in PBS. The protein chromatography with nanoparticles described in Example 18 using the chromatographic process described in Example 36. The results are displayed in FIG. 11, a silver stain 3-8% Tris-acetate gel polyacrylamide gel. The nanoparticles were used at two concentrations, for samples displayed in lanes 1 through 5, 5 uL of nanoparticle slurry was used for the protein chromatography and for lanes 6 through 10, 20 uL of nanoparticle slurry was used for the protein chromatography. All the particles were first coated with amino-silane, Example 16 and Example 17. The Cibacron blue was bound to this amino-silane surface by the process in Example 18. The samples were isolated using the following coated nanoparticles; ~50 nm diameter titanium oxide (lanes 1 and 6), ~25 nm diameter zirconium oxide (lanes 2 and 7), ~200 nm diameter kaolin (lanes 3 and 8), ~35 nm diameter tungsten oxide (lanes 4 and 9), and ~45 nm diameter aluminum oxide (lanes 5 and 10). The sample displayed in lane "C" is unfractionated serum at the same concentration as the incoming material.

While the present invention has been described with reference to its preferred embodiments and the foregoing non-limiting examples, those skilled in the art will understand and appreciate that the scope of the present invention is intended to be limited only the claims appended hereto.

What is claimed:

1. A method of manipulating biomolecules in a sample comprising the steps of:
   a. providing solid-phase, non-porous particles having a surface area to volume ratio greater than 10, and a density greater than 2;
   b. selecting a subset of the solid-phase, non-porous particles having sedimentation rates in water where the sedimentation velocity is between about 0.1 cm/min at 10,000 G (Vmin) and about 2 cm/min at 500 G (Vmax) at standard temperature and pressure, and wherein the particles form a colloidal suspension in aqueous solution;
   c. surface-modifying the subset of the solid-phase, non-porous particles to alter their affinity for one or more classes of biomolecules, wherein the step of surface-modifying the subset of solid-phase, non-porous particles further comprises activating the subset of solid-phase, non-porous particles, passivating the subset of solid-phase, non-porous particles, or combinations thereof;
   d. incubating the sample with the surface-modified particles, thereby forming a plurality of surface-modified particle-biomolecule complexes; wherein the formation of the plurality of surface-modified particle-biomolecule complexes is reversible; and
   e. separating the plurality of surface-modified particle-biomolecule complexes from the sample.

2. The method of claim 1 further comprising the steps of:
   f. disassociating the plurality of surface-modified particle-biomolecule complexes thereby releasing the biomolecules from the surface-modified particles; and
   g. isolating the biomolecules.

3. The method of claim 1 wherein the method of manipulating biomolecules further comprises a step of isolating the biomolecules from the sample.

4. The method of claim 1 wherein the solid-phase, non-porous particles have a density between about 2 and about 2.5, and effective spherical diameters as determined by two times Stokes radius in the range of about 60 nm to about 1000 nm.

5. The method of claim 1 wherein the solid-phase, non-porous particles have a density between about 2.5 and about 3, and effective spherical diameters as determined by two times Stokes radius in the range of about 40 nm to about 800 m.

6. The method of claim 1 wherein the solid-phase, non-porous particles have a density between about 3 and about 3.5, and effective spherical diameters as determined by two times Stokes radius in the range of about 35 nm to about 400 nm.

7. The method of claim 1 wherein the solid-phase, non-porous particles have a density between about 3.5 and about 4, and effective spherical diameters as determined by two times Stokes radius in the range of about 20 nm to about 700 nm.

8. The method of claim 1 wherein the solid-phase, non-porous particles have a density between about 4 and about 4.5, and effective spherical diameters as determined by two times Stokes radius in the range of about 30 nm to about 600 nm.

9. The method of claim 1 wherein the solid-phase, non-porous particles have a density between about 4.5 and about 5, and effective spherical diameters as determined by two times Stokes radius in the range of about 25 nm to about 550 nm.

10. The method of claim 1 wherein the solid-phase, non-porous particles have a density between about 5 and about 5.5, and effective spherical diameters as determined by two times Stokes radius in the range of about 25 nm to about 500 nm.

11. The method of claim 1 wherein the solid-phase, non-porous particles have a density between about 5.5 and about 6, and effective spherical diameters as determined by two times Stokes radius in the range of about 25 nm to about 450 nm.

12. The method of claim 1 wherein solid-phase, non-porous particles have a density between about 6 and about 6.5, and effective spherical diameters as determined by two times Stokes radius in the range of about 20 nm to about 450 nm.

13. The method of claim 1 wherein the solid-phase, non-porous particles have a density between about 6.5 and about 7, and effective spherical diameters as determined by two times Stokes radius in the range of about 20 nm to about 400 nm.

14. The method of claim 1 wherein the solid-phase, non-porous particles have a density between about 7 and about 7.5, and effective spherical diameters as determined by two times Stokes radius in the range of about 20 nm to about 400 nm.

15. The method of claim 1 wherein the solid-phase, non-porous particles have a density between about 7.5 and about 14, and effective spherical diameters as determined by two times Stokes radius in the range of about 15 nm to about 300 nm.

16. The method of claim 1 wherein the solid-phase, non-porous particles have a density between about 14 and about 20, and effective spherical diameters as determined by two times Stokes radius in the range of about 12 nm to about 240 nm.

17. The method of claim 1 wherein the solid-phase, non-porous particles further comprise a material selected from the group consisting of oxides, carbides, hydroxides, nitrides, phosphates, alloys, ceramics, clays, glasses, crystals, and mixtures thereof.

18. The method of claim 1 wherein the solid-phase, non-porous particles further comprise of metals or semi-metals.

19. The method of claim 18 wherein the metals are selected from the group consisting of Al, Ca, Co, Cu, Fe, Ga, Mg, Mn, In, Ni, Ti, and Zn.

20. The method of claim 17 wherein the step of surface modifying the subset of solid-phase, non-porous particles further comprises passivating the subset of solid-phase, non-porous particles.

21. The method of claim 20 wherein the step of passivating the subset of solid-phase, non-porous particles further comprises passivating with at least one anion selected from the group consisting of borate, phosphate, fluoride, and combinations thereof.

22. The method of claim 1 wherein the step of activating the subset of solid-phase, non-porous particles further comprises coating the subset of solid-phase, non-porous particles with organosilane, alkyl amine, polyethylenimine (PEI), or combinations thereof.

23. The method of claim 22 wherein the organosilane further comprises an amino silane, an epoxy silane, an alkyl silane, a mercaptosilane, a styrene silane, an acrylamide silane, a vinyl silane or combinations thereof.

24. The method of claim 23 wherein the alkyl silane is selected from the group consisting of trimethoxysilane, triethoxysilane, and mixtures thereof.

25. The method of claim 23 wherein the amino silane is selected from the group consisting of 3-aminopropyl-triethoxysilane, 3-aminopropyl-trimethoxysilane, and combinations thereof.

26. The method of claim 23 wherein the epoxy silane is selected from the group consisting of 3-glycidyloxypropyl-triethoxysilane, glycidyloxypropyltrimthoxysilane, and combinations thereof.

27. The method of claim 1 wherein the step of activating the subset of solid-phase, non-porous particles further comprises coating the subset of solid-phase, non-porous particles with one or more biopolymer binding agents specific for one or more classes of biomolecules.

28. The method of claim 27 wherein the step of coating the subset of solid-phase, non-porous particles with the one or more biopolymer binding agents further comprises a step of applying more than one coating of the one or more biopolymer binding agents to the subset of solid-phase, non-porous particles, thereby forming multiple layers of biopolymer binding agents on the surface of subset of solid-phase, non-porous the particles.

29. The method of claim 28 wherein the step of applying more than one coating of the one or more biopolymer binding agents further comprises a step of applying a first layer comprising an aminosilane.

30. The method of claim 28 wherein the step of applying more than one coating of the one or more biopolymer binding agents further comprises a step of applying a second layer comprising a polyamine.

31. The method of claim 30 wherein the polyamine further comprises linear or branched polymers of polyethylenimine, polylysine, proteins, polypeptides, chitins, chitosins, diaminoethane, diaminodipropylamine, spermidine, lysine, or combinations thereof.

32. The method of claim 28 wherein the one or more biopolymer binding agents further comprise reactive molecules selected from the group consisting of anhydrides, divinyl sulfones, hydrazides, triazines, carboxylates, aldehydes, haloalkyles, haloacetates, hydroxyls, and combinations thereof.

33. The method of claim 28 wherein the multiple layers of biopolymer binding agents comprise at least one layer further comprising of steroids or dyes.

34. The method of claim 28 wherein the multiple layers of biopolymer binding agents comprise at least one layer further comprising of amino mercaptans, polypeptides, proteins, modified nucleic acids, oligonucleotides, or combinations thereof.

35. The method of claim 1 wherein the step of separating the plurality of surface-modified particle-biomolecule complexes from the sample further comprises a step of separation by centrifugation.

36. The method of claim 35 wherein the centrifugation is carried out by applying a centrifugal field strength of 10,000 G or less applied for one hour or less.

37. The method of claim 1 wherein the solid-phase, non-porous particles further comprise kaolin.

38. The method of claim 37 wherein the step of surface-modifying the subset of solid-phase, non-porous particles comprises a step of surface passivating the subset of solid-phase, non-porous particles with borate, phosphate, fluoride, or combinations thereof.

39. The method of claim 37 wherein the step of surface-modifying the subset of solid-phase, non-porous particles comprises a step of coating the subset of solid-phase, non-porous particles with one or more biopolymer binding agents.

40. The method of claim 39 wherein the one or more biopolymer binding agents further comprise organosilane, alkyl amine, polyethylenimine (PEI), or combinations thereof.

41. The method of claim 1 further comprising purification of the biomolecules.

42. The method of claim 1 further comprising a step of storing the biomolecules.

43. The method of claim 2 wherein the surface-modified particles further comprise polyethylenimine-epoxysilane coated kaolin.

44. The method of claim 2 wherein the surface-modified particles further comprise phosphate treated kaolin.

45. The method of claim 2 wherein the surface-modified particles further comprise epoxy-dithiothreitol-divinylsulfone coated particles.

46. The method of claim 2 wherein the surface-modified particles further comprise amino-silane coated kaolin.

47. The method of claim 2 wherein the surface-modified particles further comprise metal oxide particles.

48. The method of claim 2 wherein the surface-modified particles further comprise amino-silane coated metal oxide particles.

49. The method of claim 47 wherein the metal oxide particles are selected from the group consisting of aluminum oxide, titanium oxide, tungsten oxide, and zirconium oxide.

50. The method of claim 47 wherein the metal oxide particles are coated with borate.

51. The method of claim 47 wherein the metal oxide particles are coated with phosphate.

52. The method of claim 47 wherein the metal oxide particles are coated with inosine monophosphate.

53. The method of claim 2 wherein the surface-modified particles further comprise borate treated kaolin.

54. The method of claim 2 wherein the step of surface-modifying the subset of solid-phase, non-porous particles further comprises coating the subset of solid-phase, non-porous particles with a thiophilic epoxy-silane-dithiothreitol-divinylsulfone ligand.

55. A method of storing biomolecules comprising the steps of:
  a. providing a sample containing biomolecules;
  b. providing solid-phase, non-porous particles having a surface area to volume ratio greater than 10, and a density greater than 2;
  c. selecting a subset of the solid-phase, non-porous particles having sedimentation rates in water where the sedimentation velocity is between about 0.1 cm/min at 10,000 G (Vmin) and about 2 cm/min at 500 G (Vmax) at standard temperature and pressure, and wherein the particles form a colloidal suspension in aqueous solution;
  d. surface-modifying the subset of the solid-phase, non-porous particles to alter their affinity for one or more classes of biomolecules, wherein the step of surface-modifying the subset of solid-phase, non-porous particles further comprises activating the subset of solid-phase, non-porous particles, passivating the subset of solid-phase, non-porous particles, or combinations thereof;
  e. incubating the sample with the surface-modified particles, thereby forming a plurality of surface-modified particle-biomolecule complexes; wherein the formation of the plurality of surface-modified particle-biomolecule complexes is reversible;
  f. isolating the plurality of surface-modified particle-biomolecule complexes from the sample; and
  g. storing the plurality of surface-modified particle-biomolecule complexes.

56. The method of claim 55 further comprising the steps of:
  h. disassociating the stored plurality of surface-modified particle-biomolecule complexes thereby releasing the biomolecules from the surface-modified particles; and
  i. isolating the biomolecules.

57. The method of claim 20 wherein the step of passivating the subset of solid-phase, non-porous particles comprises passivating with one or more compounds selected from the group consisting of silicate, borate, phosphate, sulfate, carbonate, arsenate, vanadate, permanganate, molybdate, tungstenate, chromate, fluoride, EDTA, EGTA, citrate, oxalate, acetate, formate, and combinations thereof.

* * * * *

SEQUENCE LISTING

<160> NUMBER OF SEQ ID NOS: 2

<210> SEQ ID NO 1
<211> LENGTH: 27
<212> TYPE: DNA

-continued

```
<213> ORGANISM: Unknown
<220> FEATURE:
<223> OTHER INFORMATION: a nuclear chromosome encoded gene, amylogenin,
      encoded on both the X and Y chromosome

<400> SEQUENCE: 1
agatgaagaa tgtgtgtgat ggatgta                                              27

<210> SEQ ID NO 2
<211> LENGTH: 24
<212> TYPE: DNA
<213> ORGANISM: Unknown
<220> FEATURE:
<223> OTHER INFORMATION: a nuclear chromosome encoded gene, amylogenin,
      encoded on both the X and Y chromosome

<400> SEQUENCE: 2
gggctcgtaa ccataggaag ggta                                                 24
```